(12) United States Patent
Ezura et al.

(10) Patent No.: US 10,349,611 B2
(45) Date of Patent: Jul. 16, 2019

(54) HEAT-TOLERANT TOMATO MUTANT AND METHOD FOR PRODUCING THE SAME

(71) Applicant: UNIVERSITY OF TSUKUBA, Tsukuba-shi, Ibaraki (JP)

(72) Inventors: Hiroshi Ezura, Tsukuba (JP); Ken Hoshikawa, Tsukuba (JP); Shoma Fukumoto, Tsukuba (JP); Sayaka Ooshima, Aichi (JP); Mina Aiba, Aichi (JP)

(73) Assignee: UNIVERSITY OF TSUKUBA, Tsukuba-Shi, Ibaraki (JP)

(*) Notice: Subject to any disclaimer, the term of this patent is extended or adjusted under 35 U.S.C. 154(b) by 27 days.

(21) Appl. No.: 15/514,183

(22) PCT Filed: Sep. 25, 2015

(86) PCT No.: PCT/JP2015/077186
§ 371 (c)(1),
(2) Date: Mar. 24, 2017

(87) PCT Pub. No.: WO2016/047778
PCT Pub. Date: Mar. 31, 2016

(65) Prior Publication Data
US 2017/0292130 A1    Oct. 12, 2017

(30) Foreign Application Priority Data
Sep. 25, 2014   (JP) ................. 2014-195891

(51) Int. Cl.
| | |
|---|---|
| *A01H 5/08* | (2018.01) |
| *C12N 15/82* | (2006.01) |
| *A01H 6/82* | (2018.01) |
| *A01H 1/06* | (2006.01) |
| *C12N 15/01* | (2006.01) |

(52) U.S. Cl.
CPC .............. *A01H 6/825* (2018.05); *A01H 1/06* (2013.01); *A01H 5/08* (2013.01); *C12N 15/01* (2013.01); *C12N 15/8249* (2013.01); *C12N 15/8261* (2013.01); *C12N 15/8273* (2013.01); *Y02A 40/138* (2018.01)

(58) Field of Classification Search
None
See application file for complete search history.

(56) References Cited

FOREIGN PATENT DOCUMENTS

| | | |
|---|---|---|
| JP | H11-199419 A | 7/1999 |
| JP | 2002-95370 A | 4/2002 |
| WO | WO 2007-058347 A1 | 5/2007 |

OTHER PUBLICATIONS

Scott et al. Use of hybrids to develop heat tolerant tomato cultivars. Proc. Fla. State. Hort. Soc. 1986. 99: 311-314.*
Abdul-Baki. Tolerance of tomato cultivars and selected germplasm to heat stress. Journal of the American Society for Horticultural Science. 1991. 6: 1113-1116.*
Firon et al. Pollen grains of heat tolerant tomato cultivars retain higher carbohydrate concentration under heat stress conditions. Scientia Horticulturae. 2006. 109: 212-217.*
Watanabe et al. Ethylmethylsulfonate (EMS) mutagenesis of *Solanum lycopersicum* cv. Micro-Tom for large-scale mutant screens. Plant Biotechnology. 2007. 24: 33-38.*
Tomatoma. Tomato Mutants Archive. Wild Type Strain List. 2012. Retrieved from http://tomatoma.nbrp.jp/strainListAction.do?strainTypeId=3. pp. 1-5.*
Dave's Garden. Currant Tomato, Wild Tomato 'Texas Wild'. 2004. Retrieved from https://davesgarden.conn/guides/pf/go/50554/. pp. 5-6.*
Fukumoto, S. et al., "Isolation and Gene Identification of Heat Tolerant Mutant Lines from Micro-Tom Mutant Collections", *Horticultural Research*, vol. 14, No. 1, Mar. 2015, 3 pages. (English language translation only).
Fukumoto, S., et al., "Isolation and Characterization of Heat Tolerant Mutant Lines from Micro-Tom Mutant Collections", *Breeding Research*, vol. 16, No. 2, Sep. 2014, 5 pages (with English language translation).
Jones, P.D., et al., "Surface Air Temperature and Its Changes Over the Past 150 Years", *Reviews of Geophysics*, vol. 37, No. 2, May 1999, pp. 173-199.
Nkansah, G. et al., "Relationship Between Some Physiological Characters and Yield of Heat-Tolerant, Non-Tolerant, and Tropical Tomato Cultivars Grown at High Temperature", *J. Japan Soc. Hort. Sci.*, vol. 62, No. 4, 1994, pp. 781-788.
Porter, J., "Rising Temperatures are Likely to Reduce Crop Yields", *Nature*, vol. 436, Jul. 2005, pp. 174.
Rahman, S.M. et al., "Effects of Temperature and Water Stress on Growth, Yield and Physiological Characteristics of Heat-Tolerant Tomato", *Jpn. J. Trop. Agr.*, vol. 42, No. 1, 1998, pp. 46-53.
Willits, D.H. et al., "The Effect of Night Temperature on Greenhouse Grown Tomato Yields in Warm Climates", *Agriculture and Forest Meteorology*, vol. 92, 1998, pp. 191-202.
International Search Report in corresponding International Application No. PCT/JP2015/077186, dated Nov. 10, 2015, 7 pages.
Fukumoto, S. et al., "Isolation and Gene Identification of Heat Tolerant Mutant Lines from Micro-Tom Mutant Collections", *Horticultural Research*, vol. 14, No. 1, Mar. 2015, 5 pages. (with English language translation).
Willits, D.H. et al., "The Effect of Night Temperature on Greenhouse Grown Tomato Yields in Warm Climates", *Agricultural and Forest Meteorology*, vol. 92, 1998, pp. 191-202.
Xiong L., et al., "Growth-stimulatory monoclonal antibodies against human insulin-like growth factor 1 receptor," *Proc. Natl. Acad. Sci. USA*, 89:5356-5360 (Jun. 1992).

* cited by examiner

*Primary Examiner* — Ashley K Buran
(74) *Attorney, Agent, or Firm* — Brinks Gilson & Lione

(57) ABSTRACT

A heat-tolerant tomato plant exhibiting a high capacity for developing seed-containing fruits under high temperature conditions is provided. The present invention relates to a method for producing a heat-tolerant tomato plant comprising introducing a genetic mutation into a tomato plant, wherein the mutation improves the pollen viability and the capacity for developing seed-containing fruits under high temperature conditions compared with wild-type plant; and a heat-tolerant tomato plant into which the mutation has been introduced.

6 Claims, 14 Drawing Sheets

Specification includes a Sequence Listing.

HEAT-TOLERANT TOMATO MUTANT AND METHOD FOR PRODUCING THE SAME

This application is a 371 application of PCT/JP2015/077186 having an international filing date of Sep. 25, 2015, which claims priority to JP2014-195891 filed Sep. 25, 2014, the entire contents of which are incorporated herein by reference.

TECHNICAL FIELD

The present invention relates to a heat-tolerant tomato mutant and a method for producing the same.

BACKGROUND ART

Higher plants are exposed to various types of environmental stress, such as high temperature, low temperature, dryness, salt, and metal. Among various types of environmental stress, heat stress due to high temperature imposes a serious damage on plant growth, and it accordingly significantly affects agricultural production in the world (Peet, M. M., Willits, D. H., 1998, Agric. Forest Meteorol., 92, pp. 191-202; Hall, A. E., 2001, Crop Responses to Environment, CRC Press LLC, Boca Raton, Fla.). According to the report made by the Intergovernmental Panel on Climatic Change, the world mean temperature increases by 0.3° C. every century due to global warming. It is predicted that the mean temperature becomes 3° C. higher than the current level on 2100 and such problem becomes more serious in the future (Jones, P. D., et al., 1999, Rev. Geophys., 37, pp. 173-199; Porter, J. R., 2005, Nature 436, p. 174).

As year-round cultivation of tomatoes becomes popular, various barriers to the growth, such as fruit set failure caused by lowered pollen fertility, decreased size, and deteriorated quality of tomatoes due to high temperature in summer, have been reported. Pollen development failure and lowered pollen fertility are major causes of fruit set failure in high temperature season. In order to overcome such problems, heat tolerance has been imparted to plants via various techniques. As a chemical spraying-based technique, a method for reducing high-temperature stress under high-temperature conditions and promoting healthy growth of plants by spraying an agent for imparting high-temperature-stress tolerance for agricultural/horticultural use to plants has been known (Japanese patent publication No. H11-199419 A (1999)). As a genetic engineering-based technique, a method for imparting heat tolerance to transgenic tobacco plants by causing the overexpression of tomato-derived mitochondrial small heat-shock proteins has been known (Japanese patent publication No. 2002-95370 A). As ingenuity in facilities and methods for cultivation, in addition, a developed apparatus for effectively cooling only buds under development stage including stamens that are most sensitive to high temperature to an optimal temperature for plant growth and a method for promoting fruit set and growth of plants using it are known (International Publication No. WO 2007/058347). However, such conventional techniques for imparting heat tolerance to plants are problematic in terms of economic efficiency, environmental load, and/or workability. Accordingly, breeding a heat-tolerant variety that exhibits stable fruit set even in high temperature season is urgently required. In addition, a variety capable of efficiently developing a normal fruit with seeds even under high temperature conditions is required as a parent for breeding a heat-tolerant variety. However, no techniques for efficiently breeding such heat-tolerant variety have yet been established.

CITATION LIST

Patent Documents

Patent Document 1: Japanese Patent Publication No. H11-199419 A (1999)
Patent Document 2: Japanese Patent Publication No. 2002-95370 A
Patent Document 3: International Publication WO 2007/058347

Non-Patent Documents

Non-Patent Document 1: Peet, M. M., Willits, D. H., (1998) Agric. Forest Meteorol., 92, p. 191-202
Non-Patent Document 2: Hall, A. E., (2001) Crop Responses to Environment, CRC Press LLC, Boca Raton, Fla.
Non-Patent Document 3: Jones, P. D., et al., (1999) Rev. Geophys., 37, p. 173-199
Non-Patent Document 4: Porter, J. R., (2005) Nature 436, p. 174

SUMMARY OF THE INVENTION

Problem to Be Solved by the Invention

An object of the present invention is to provide a heat-tolerant tomato plant that has a high capacity of developing seed-containing fruits under high temperature conditions.

Means for Solving the Problem

The present inventors have conducted concentrated studies in order to solve the above problem. As a result, they discovered the presence of a genetic mutation that improves the pollen viability and the capacity for developing seed-containing fruits. This has led to the completion of the present invention.

Specifically, the present invention includes the following.

[1] A method for producing a heat-tolerant tomato plant comprising introducing a genetic mutation that improves the capacity for developing seed-containing fruits under high temperature conditions compared with wild-type plant, into a tomato plant.

The genetic mutation is preferably from the JHT06 strain of Accession number FERM BP-22278.

The genetic mutation preferably improves the pollen viability, the rate of developing seed-containing fruits and the yield of seed-containing fruits, under high temperature conditions.

The genetic mutation may increase leaf chlorophyll content compared with wild-type plant.

The genetic mutation is, for example, a non-synonymous mutation or gene deficiency in at least one gene shown in Table 3 below. The non-synonymous mutation may be a nucleotide mutation that causes an amino acid mutation shown in Table 3 corresponding to the gene mentioned above, or it may be a SNP mutation shown in Table 3 corresponding to the gene mentioned above.

This method preferably comprises exposing the tomato plant into which the mutation has been introduced to temperature of 35° C. to 40° C.

[2] The heat-tolerant tomato plant into which the mutation has been introduced, which is produced by the method according to [1] above.

Examples of such heat-tolerant tomato plant include the JHT06 strain of Accession number FERM BP-22278 and a derivative thereof carrying the mutation.

[3] A method for breeding a heat-tolerant tomato plant comprising crossing the heat-tolerant tomato plant according to [2] above as a breeding parent with another tomato plant and obtaining a progeny tomato plant having the mutation.

This description includes the disclosure in Japanese Patent Application No. 2014-195891 of which the present application claims the priority.

Effects of the Invention

According to the present invention, a tomato plant that has an excellent capacity for developing seed-containing fruits under high temperature conditions can be produced with high efficiency.

DETAILED DESCRIPTION OF THE PREFERRED EMBODIMENTS

Figure 1:
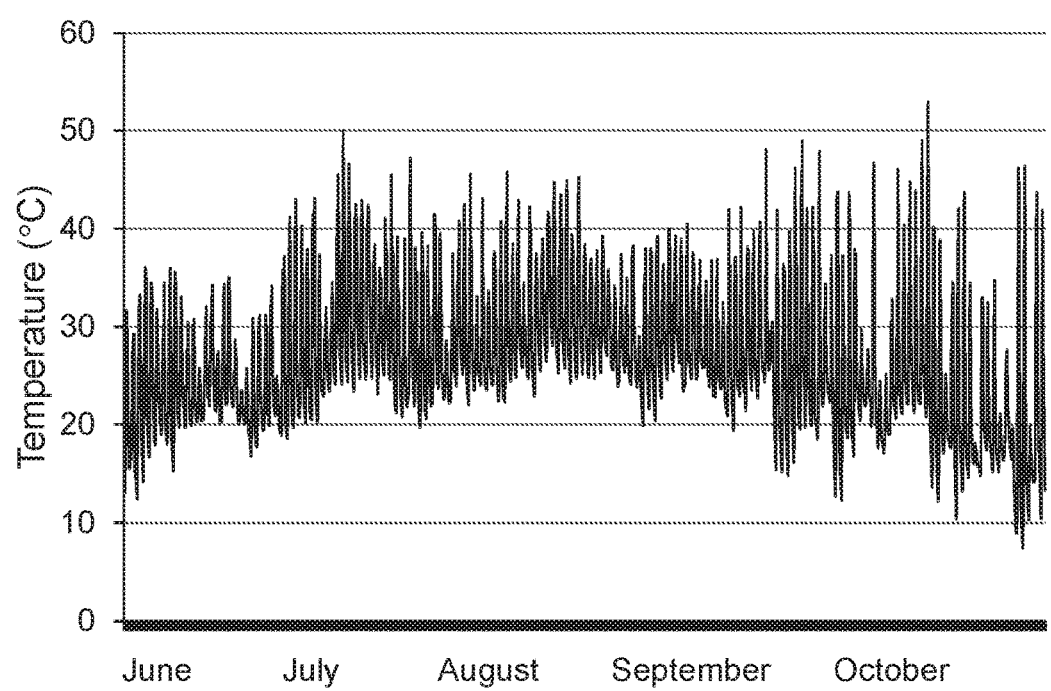
FIG. 1 shows changes in temperature in a greenhouse (Jun. 1 to Nov. 1, 2013).

Hereafter, the present invention is described in detail.

The present invention relates to a method for producing a heat-tolerant tomato plant that has improvement of fruit set failure in summer with the use of a genetic mutation that provides an increased fruit set efficiency of tomatoes under high temperature conditions in summer.

According to the present invention, more specifically, a heat-tolerant tomato plant can be produced with high efficiency by introducing a genetic mutation that improves the capacity for developing seed-containing fruits in, e.g., a mutant, compared with the wild-type tomato plant (a tomato plant before introduction of a mutation, e.g., Micro-Tom wild-type) into a tomato plant.

Typically, the present invention provides a method for producing a heat-tolerant tomato plant by introducing, as the genetic mutation that improves the capacity for developing seed-containing fruits, a genetic mutation that improves at least one, preferably all, selected from the pollen viability, the rate of developing seed-containing fruits and the yield of seed-containing fruits under high temperature conditions compared with a wild-type tomato plant (a tomato plant before introduction of a mutation, e.g., Micro-Tom wild-type) into a tomato plant.

In the present invention, the "pollen viability" refers to a proportion (%) of the number of living pollens relative to the total number of pollens collected from an individual. The "rate of developing seed-containing fruits" refers to a proportion (%) of the number of seed-containing fruits relative to the total number of fruits obtained from an individual plant. The "yield of seed-containing fruits" refers to the sum of weights of all seed-containing fruits (i.e., the total weight of seed-containing fruits) obtained from an individual plant.

When a plant is exposed to high temperature conditions, and more specifically, the temperature conditions of 30° C. or more and less than 45° C., e.g., 35° C. to 40° C. (e.g., as a temperature in a greenhouse) within a period from 2 weeks before blooming to the day of blooming during cultivation (e.g., cultivation in a greenhouse), the genetic mutation preferably provides an increase of leaf chlorophyll content compared with the wild-type plant exposed to the same high-temperature conditions, in addition to improvement of at least one, preferably all, selected from the pollen viability, the rate of developing seed-containing fruits and the yield of seed-containing fruits compared with the wild-type plant. Such genetic mutation preferably also increases the rate of fruit set, the total number of fruit set, and the stamen length (i.e., reduces suppression of stamen elongation) per individual plant compared with the wild-type plant, when exposed to the high temperature conditions as described above during cultivation.

Such genetic mutation is a mutation generated preferably in at least one gene shown in Table 2 below or preferably in at least one gene shown in Table 3 below. Such genetic mutation is more preferably a non-synonymous mutation in at least one gene shown in Table 2 or Table 3. In the present invention, the term "non-synonymous mutation" refers to a mutation that alters an amino acid sequence among nucleotide mutations occurring in a coding sequence of a gene. Examples thereof include substitution of nucleotides causing amino acid substitution (it is also referred to as a non-synonymous substitution or missense mutation), a nonsense mutation generating a stop codon that stops protein translation, and insertion or deletion mutation of nucleotides causing amino acid insertion or deletion or reading frame changes (i.e., frameshift). A non-synonymous mutation occurring in the genes shown in Table 2 or 3 is a mutation that alters functional levels of such genes.

Such non-synonymous mutation is preferably a nucleotide mutation causing an amino acid mutation as shown in Table 3. For example, such non-synonymous mutation may be a mutation such as an SNP mutation as shown in Table 3 or 4.

More specifically, the genetic mutation of the present invention may be a mutation in a gene shown in Table 3 (Gene Nos. Solyc04g076040.2.1, Solyc06g005540.1.1, Solyc06g005930.1.1, or Solyc06g071730.2.1), for example, a gene comprising at least one nucleotide sequence selected from the group consisting of SEQ ID NOs: 63, 65, 67, and 69, or the group consisting of SEQ ID NOs: 85, 73, 77, and 81; or a functional mutant thereof that comprises a nucleotide sequence typically having 80% or more, preferably 90% or more, more preferably 95% or more, and particularly preferably 99% or more sequence identity to the aforementioned nucleotide sequence selected. The genetic mutation of the present invention may be a mutation in, for example, a gene encoding an amino acid sequence selected from the group consisting of SEQ ID NOs: 64, 66, 68, and 70 or the group consisting of SEQ ID NOs: 86, 74, 78, and 82, or a functional mutant thereof that encodes a functional protein comprising an amino acid sequence typically having 90% or more, preferably 95% or more, and more preferably 99% or more, e.g., 99.5% or more sequence identity to the aforementioned amino acid sequence selected.

Alternatively, the genetic mutation of the present invention may be a mutation that causes a loss of functions (that is, a gene deficiency) of at least one gene shown in Table 2, and preferably a gene shown in Table 3, for example, a gene comprising at least one nucleotide sequence selected from the group consisting of SEQ ID NOs: 63, 65, 67, and 69 or the group consisting of SEQ ID NOs: 85, 73, 77, and 81, or a functional mutant thereof that comprises a nucleotide sequence typically having 80% or higher, preferably 90% or higher, more preferably 95% or higher, and particularly preferably 99% or higher sequence identity to the aforementioned nucleotide sequence selected. Alternatively, the genetic mutation of the present invention may be a deficiency of a gene encoding an amino acid sequence selected from the group consisting of SEQ ID NOs: 64, 66, 68, and 70 or the group consisting of SEQ ID NOs: 86, 74, 78, and 82, or a functional mutant thereof that encodes a functional protein comprising an amino acid sequence having typically 90% or more, preferably 95% or more, and more preferably 99% or more, e.g., 99.5% or more sequence identity to the aforementioned amino acid sequence selected. Such deficiency of a gene may be a deletion of a part of the gene or the entire gene on the genome. Alternatively, a deficiency of a gene may be a mutation into a gene that is untranslated into a protein due to lack of an initiation codon, frameshift, and/or generation of a stop codon; or into a gene that encodes a protein that had lost its functions.

According to one embodiment, the genetic mutation of the present invention can be an SNP mutation in the nucleotide sequence as shown in SEQ ID NO: 59 shown in Table 3; or a nucleotide mutation G181T as defined on the basis of the reference nucleotide sequence as shown in SEQ ID NO: 63 or a nucleotide mutation causing an amino acid mutation D61Y as defined on the basis of the reference amino acid sequence as shown in SEQ ID NO: 64 corresponding to the SNP mutation.

Alternatively, the genetic mutation of the present invention may be an SNP mutation in the nucleotide sequence as shown in SEQ ID NO: 60 shown in Table 3; or a nucleotide mutation T2C defined on the basis of the reference nucleotide sequence as shown in SEQ ID NO: 65 or a nucleotide mutation causing an amino acid mutation M1T defined on the basis of the reference amino acid sequence as shown in SEQ ID NO: 66 corresponding to the SNP mutation. The genetic mutation of the present invention may be a substitution of T at position 2 defined on the basis of the reference nucleotide sequence as shown in SEQ ID NO: 65 or 73 (causing lack of an initiation codon), a deletion of the nucleotide sequence from positions 51 to 63, and/or a nucleotide mutation causing the amino acid mutation Y39* (* indicates the generation of a stop codon) defined on the basis of the reference amino acid sequence as shown in SEQ ID NO: 66 or 74; for example, nucleotide mutation T115A.

Alternatively, the genetic mutation of the present invention may be an SNP mutation in the nucleotide sequence as shown in SEQ ID NO: 61 shown in Table 3; or a nucleotide mutation C334T defined on the basis of the reference nucleotide sequence as shown in SEQ ID NO: 67 or a nucleotide mutation causing an amino acid mutation Q112* (* indicates the generation of a stop codon) defined on the basis of the reference amino acid sequence as shown in SEQ ID NO: 68 corresponding to the SNP mutation.

Alternatively, the genetic mutation of the present invention may be an SNP mutation in the nucleotide sequence as shown in SEQ ID NO: 61 shown in Table 3; or a nucleotide mutation T350G defined on the basis of the nucleotide sequence as shown in SEQ ID NO: 67 or a nucleotide mutation causing an amino acid mutation L117* (* indicates the generation of a stop codon) defined on the basis of the reference amino acid sequence as shown in SEQ ID NO: 68.

Alternatively, the genetic mutation of the present invention may be an insertion of a nucleotide (e.g., glycine) at position 158 defined on the basis of the reference nucleotide sequence as shown in SEQ ID NO: 67 or 77, which causes a frameshift and the generation of a stop codon. Alternatively, the genetic mutation of the present invention may be the generation of a stop codon in the nucleotide sequence as shown in SEQ ID NO: 75.

Alternatively, the genetic mutation of the present invention may be an SNP mutation in the nucleotide sequence as shown in SEQ ID NO: 62 shown in Table 3; or a nucleotide mutation A306T defined on the basis of the reference nucleotide sequence as shown in SEQ ID NO: 69 or 81 or a nucleotide mutation causing an amino acid mutation *102C (* indicates the generation of a stop codon) defined on the basis of the reference amino acid sequence as shown in SEQ ID NO: 70 or 82.

The genetic mutation is preferably from the tomato JHT06 strain of Accession Number FERM BP-22278. That is, it is preferably a genetic mutation carried by the JHT06 strain or a genetic mutation seen in the JHT06 strain.

A single or a combination of the genetic mutation described above may be introduced into a plant. Such genetic mutation may be a combination of a mutation in the Solyc06g005540.1.1 gene and a mutation in the Solyc06g005930.1.1 gene, e.g., deficiency of both such genes.

In the present invention, the expression "(mutation) defined on the basis of the reference sequence as shown in SEQ ID NO: 'X'" indicates that the mutation is identified by the type of mutated nucleotide or amino acid and its position based on the sequence as shown in SEQ ID NO: 'X' as a reference. More specifically, this expression refers to an indicated mutation in the sequence as shown in SEQ ID NO: 'X' or a mutation of a nucleotide or amino acid in a sequence having a high sequence identity to the sequence as shown in SEQ ID NO: 'X' which corresponds to (or is aligned with) the indicated mutation. In the present invention, a nucleotide mutation is optionally denoted by a nucleotide before mutation designated by A (adenine), T (thymine), G (guanine), or C (cytosine), followed by a position of the mutation and a nucleotide after mutation. For example, C334T defined on the basis of the reference nucleotide sequence as shown in SEQ ID NO: 67 indicates a mutation in which a nucleotide (cytosine) corresponding to cytosine at position 334 in the nucleotide sequence as shown in SEQ ID NO: 67 is substituted with thymine. Herein, the nucleotide "corresponding to" cytosine at position 334 in the nucleotide sequence as shown in SEQ ID NO: 67 refers to a cytosine that is aligned to the cytosine at position 334 in the nucleotide sequence as shown in SEQ ID NO: 67, in a nucleotide sequence having a high sequence identity (e.g., 80% or more, preferably 90% or more, more preferably 95% or more, and particularly preferably 99% or more) to the nucleotide sequence as shown in SEQ ID NO: 67, when the nucleotide sequence is aligned with the nucleotide sequence as shown in SEQ ID NO: 67. According to the present invention, similarly and optionally, an amino acid mutation is denoted by an amino acid before mutation (or an asterisk indicating stop codon), which is designated by one-letter code that is generally used in the art, followed by a position of the mutation, and an amino acid after mutation (or an asterisk indicating stop codon). For example, amino acid mutation Q112* defined on the basis of the reference amino acid sequence as shown in SEQ ID NO: 68 refers to a mutation in which an amino acid (glutamine) corresponding to Q (glutamine) at position 112 in the amino acid sequence as shown in SEQ ID NO: 68 is changed into a stop codon. Herein, the amino acid "corresponding to" glutamine at position 112 in the amino acid sequence as shown in SEQ ID NO: 68 refers to a glutamine that is aligned to the glutamine at position 112 in the nucleotide sequence as shown in SEQ ID NO: 68, in an amino acid sequence having a high sequence identity (typically 90% or more, preferably 95% or more, and more preferably 99% or more, e.g., 99.5% or more) to the amino acid sequence as shown in SEQ ID NO: 68, when the amino acid sequence is aligned with the amino acid sequence as shown in SEQ ID NO: 68. In the present invention, notations of other mutations can be understood in the same manner as described above.

In the present invention, the "nucleotide mutation causing an amino acid mutation" refers to a change in a nucleotide sequence (e.g., substitution, insertion, or deletion of one or more nucleotides) that causes the indicated amino acid mutation.

The genetic mutation described above can be introduced into the genome of a tomato plant in accordance with a conventional technique. For example, a tomato plant into which the genetic mutation of the present invention has been introduced may be obtained by producing a mutant by mutagen treatment of a tomato plant (e.g., treatment with a mutagen-inducing agent such as ethylmethane sulfonate (EMS), ethyleneimine (MI), propanesultone, or N-methyl-N-nitrosourethane (MNU) or radiation of X-rays, gamma rays, ion beams, ultraviolet rays or the like) and screening the produced mutant population for an individual having the mutation. Alternatively, the genetic mutation of the present invention may be introduced into the genome of a tomato plant via, for example, site-directed mutagenesis. The genetic mutation may be introduced into a tomato plant by homologous recombination via transformation using a vector containing a gene or fragment thereof comprising the genetic mutation. The genetic mutation may be introduced into a tomato plant by crossing a tomato mutant into which the mutation has been introduced or a progeny plant thereof having the mutation with another tomato plant, and screening the resulting progeny plants for an individual having the mutation. Screening for the individual having the genetic mutation can be carried out by any method of detecting a genetic mutation (e.g., a method using nucleic acid amplification and/or Southern hybridization). For example, the screening can be carried out by amplifying a region into which the mutation has been introduced via PCR, determining the nucleotide sequence of the amplified product, and comparing the determined nucleotide sequence with the genome sequence of a tomato plant into which no mutation has been introduced to examine the presence or absence of the mutation. Primers to be used for the PCR method can be designed on the basis of a tomato genome sequence, e.g., a known genome sequence of the Micro-Tom wild-type. For example, forward primers and/or reverse primers shown in Table 1 below can be used.

Alternatively, the screening for an individual having the genetic mutation as described above may be carried out by hybridizing an amplified product of a region into which the mutation has been introduced to an amplified product of the same region into which no mutation has been introduced, to form heterologous duplexes, specifically detecting a mismatched site that would be generated upon introduction of a mutation (e.g., by detection via specific cleavage of a mismatched site with a nuclease), and determining the presence or absence of the mutation. Also, for example, an F-PHFA method comprising competitive hybridization in combination with fluorescence resonance energy transfer (FRET), a method using hybridization with a probe that specifically binds to a region into which the mutation has been introduced, or a method comprising such hybridization in combination with real-time PCR, can be employed. Such various techniques for detecting genetic mutation can be performed using commercially available products, such as sequencers, PCR machines, and various genetic mutation detection kits.

A gene in the tomato plant into which the genetic mutation is to be introduced may be at least one of the genes shown in Table 2 or 3 or homologs thereof (e.g., 1 to 4 genes selected from 4 genes shown in Table 3). The gene may be the gene described above, such as a gene (coding sequence) of a tomato plant into which the genetic mutation is to be introduced, having a high sequence identity (e.g., 80% or more, preferably 90% or more, more preferably 95% or more, and particularly preferably 99% or more) to the nucleotide sequence as shown in any of SEQ ID NOs shown in Table 2 or 3 (a coding sequence).

A tomato plant into which the genetic mutation is to be introduced may be any tomato plant of *Solanum lycopersicum*, and preferably be a non-heat-tolerant tomato plant. In one embodiment, a tomato plant may be a Micro-Tom wild-type or a derivative thereof. The Micro-Tom wild-type is known as a tomato variety Micro-Tom (*Solanum lycopersicum*, cv. Micro-Tom) (Scott J W, Harbaugh BK, 1989, Micro-Tom, A miniature dwarf tomato, Florida Agr. Expt.

Sta. Circ., 370, pp. 1-6) and commercially available. Micro-Tom can be available from the Tomato Genetics Resource Center (TGRC, U.S.A.) under Accession No. LA3911. The tomato variety Micro-Tom is a dwarf cultivar (about 10 to 20 cm) with small leaves and small fruits, and it can be crossed with a conventional variety. The whole genome sequence of the tomato variety Micro-Tom has been determined (Kobayashi, M., et al., 2014, Plant Cell Physiol., February, 2014, 55 (2): 445-454).

In the present invention, the term "derivative" refers to a progeny plant of an original plant, which is produced through at least one crossing with another plant strain or variety, or mutagenesis or introduction of mutation.

It is preferred that the tomato plant into which the genetic mutation has been introduced be placed under high temperature conditions during cultivation and examined for heat tolerance. Specifically, the tomato plant into which the genetic mutation has been introduced is exposed to a temperature of 30° C. or more and less than 45° C., e.g., 35° C. to 40° C. (e.g., as a temperature in a greenhouse). Exposure to such high temperature stress is preferably carried out during daytime over a period from 2 weeks before blooming 2 to the day of blooming for at least 6 hours per day. While a plant may not be exposed to high temperature stress every day, a plant is more preferably exposed to high temperature stress for, e.g., 50% or more, and preferably 80% or more of days of the exposure period. After the exposure to high temperature stress, the rate of fruit set, the fruit yield, and other properties of the tomato plant into which the genetic mutation has been introduced can be examined to confirm whether the plant has a good efficiency for fruit set and good development of seed-containing fruits even under high temperature conditions; that is, the plant has heat tolerance. The heat-tolerant tomato plant into which the genetic mutation has been introduced is preferably subjected to detection of the mutation in its genome sequence to confirm that the plant genome has the mutation. The detection of the mutation can be performed in the same manner as described above.

According to the method of the present invention, a tomato plant that has improved heat tolerance as a result of the introduction of the genetic mutation can be produced. The resulting heat-tolerant tomato plant exhibits improvement in the pollen viability, the rate of developing seed-containing fruits, and the yield of seed-containing fruits under high temperature conditions. The heat-tolerant tomato plant according to the present invention exhibits the pollen viability under high temperature conditions, which is improved by, for example 1.3 times or greater, preferably 1.5 times or greater, more preferably 2 times or greater, and further preferably 5 times or greater than a plant into which no mutation has been introduced. Accordingly, the heat-tolerant tomato plant of the present invention can maintain a high pollen fertility even under high temperature conditions. Also, the heat-tolerant tomato plant of the present invention preferably exhibits the increased total number of pollens, compared with the plant into which no mutation has been introduced, under high temperature conditions. The heat-tolerant tomato plant of the present invention may have the total number of pollens, which is increased by, for example 1.3 times or greater, and preferably 1.5 times or greater than the plant into which no mutation has been introduced. In the present invention, the term "high temperature conditions" refers to the conditions in which a tomato plant is exposed to a temperature of 30° C. or more and less than 45° C., e.g., as 35° C. to 40° C., during a period from 2 weeks before blooming to the day of blooming for at least several hours, and preferably at least several tens of hours, in total.

The heat-tolerant tomato plant of the present invention exhibits the rate of developing seed-containing fruits (i.e., the proportion of the number of seed-containing fruits relative to the total number of fruits) under high temperature conditions, which is improved by, for example, 1.3 times or more, preferably 1.5 times or more, and more preferably 2 times or more, compared with a plant into which no mutation has been introduced. The heat-tolerant tomato plant of the present invention exhibits the yield of seed-containing fruits (i.e., the total weight of seed-containing fruits) under high temperature conditions, which is improved by, for example, 1.3 times or more, preferably 1.5 times or more, and more preferably 2 times or more, compared with a plant into which no mutation has been introduced.

In the heat-tolerant tomato plant of the present invention, the total number of fruits (i.e., the total number of fruit set) including both seed-containing and seedless fruits under high temperature conditions is preferably also increased, in comparison with a plant into which no mutation has been introduced. The heat-tolerant tomato plant of the present invention can exhibit the total number of fruit set, which is increased by, for example, 1.3 times or more, and preferably 1.5 times or more, compared with a plant into which no mutation has been introduced. In the heat-tolerant tomato plant of the present invention, the rate of fruit set including both seed-containing and seedless fruits (i.e., the proportion of the total number of fruit set relative to the total number of blooming) under high temperature conditions is preferably also increased, in comparison with a plant into which no mutation has been introduced. The heat-tolerant tomato plant of the present invention can exhibit the rate of fruit set, which is increased by, for example, 1.3 times or more, compared with a plant into which no mutation has been introduced.

In the heat-tolerant tomato plant of the present invention, in addition, the total number of pollens is preferably increased under high temperature conditions, compared with a plant into which no mutation has been introduced. The heat-tolerant tomato plant of the present invention can exhibit the total number of pollens, which is increased by, for example, 1.3 times or more, and preferably 1.5 times or more, compared with a plant into which no mutation has been introduced. In the heat-tolerant tomato plant of the present invention, the rate of fruit set including both seed-containing and seedless fruits (i.e., the proportion of the total number of fruit set relative to the total number of blooming) under the high temperature conditions is preferably also increased in comparison with a plant into which no mutation has been introduced. The heat-tolerant tomato plant of the present invention can exhibit the rate of fruit set, which is increased by, for example, 1.3 times or more, compared with a plant into which no mutation has been introduced.

In one preferred embodiment, as the heat-tolerant tomato plant of the present invention grows, the plant has deeper green leaves thereof than a plant into which no mutation has been introduced, regardless of whether it has grown under high temperature conditions as described above or normal temperature conditions below 30° C. Leaf chlorophyll content of such heat-tolerant tomato plant of the present invention is increased by, for example, 5% or more, and preferably 10% or more, compared with a plant into which no mutation has been introduced at the same number of days after seeding. Chlorophyll content may be determined using, for example, a chlorophyll optical density (SPAD) level as an indicator. An SPAD level can be determined in accordance with a conventional technique on the basis of an optical density difference for a sample between a red region that is selectively absorbed by chlorophyll and an infrared region that is not substantially absorbed by a pigment. An SPAD level can be measured by a non-destructive assay with a commercially available apparatus for SPAD measurement (i.e., a chlorophyll meter).

In one preferred embodiment, the heat-tolerant tomato plant according to the present invention is less likely to experience suppression of stamen elongation under the high temperature conditions. The stamen length of such heat-tolerant tomato plant of the present invention becomes longer by, for example, 5% or more, and preferably 10% or more, compared with a plant into which no mutation has been introduced. As a result of reduction of suppression of stamen elongation, a plant becomes less likely to cause pollination inhibition, and the capacity for pollination becomes improved.

The heat-tolerant tomato plant of the present invention may be homozygous or heterozygous for the genetic mutation, preferably homozygous for the genetic mutation.

In one preferred embodiment, the heat-tolerant tomato plant according to the present invention is the JHT06 strain being a mutant of the tomato variety Micro-Tom (*Solanum lycopersicum*, cv. Micro-Tom), or a derivative thereof. The JHT06 strain and a derivative thereof carry the genetic mutation described above. A minimum number of 2500 seeds of the JHT06 strain were deposited on Sep. 17, 2014 at the International Patent Organism Depositary of the National Institute of Technology and Evaluation (NITE-IPOD, #120, 2-5-8 Kazusakamatari, Kisarazu-shi, Chiba, Japan) under Accession Number FERM BP-22278 under the Budapest Treaty as an international deposit. All restrictions upon availability to the public will be irrevocably removed upon issuance for the enforceable life of the patent. The heat-tolerant tomato plant according to the present invention can also be preferably used not only for the production of tomatoes, but also preferably as a breeding parent.

In the present invention, the term "tomato plant" basically includes stem, leaf, root, flower, bud, fruit (pulp and fruit skin), seed, cell, callus and the like as well as whole plant of tomato, although it varies depending on the context.

In addition, the present invention provides a method for breeding a heat-tolerant tomato plant comprising crossing the heat-tolerant tomato plant of the present invention as a breeding parent with another tomato plant and obtaining a progeny tomato plant having the mutation described above. By repeating such crossing and/or self-crossing of the resulting progenies by a conventional technique, the genetic mutation and a trait resulting therefrom (e.g., heat tolerance) can be fixed in the tomato plant of interest. The resulting progenies are preferably verified to have the mutation of interest. The verification of the mutation may be performed by any method capable of detecting the genetic mutation as described above.

EXAMPLES

Hereafter, the present invention is described in greater detail with reference to the Examples, although the technical scope of the present invention is not limited to these Examples.

Example 1

Selection of Heat-Tolerant Mutants (1) Cultivation Method

In this Example and subsequent Examples, tomatoes were cultivated in a greenhouse in the following manner. Culture soil was added to connected pots (Sinwa Co., Ltd.). For sowing, seeds were placed on the culture soil and then covered thinly with culture soil. In order to prevent soil from drying, water was applied thereto every day, and fertilizer was applied once a week simultaneously with watering. Flowers were vibrated with a vibrator to assist pollination.

(2) Selection of Candidate Heat-Tolerant Strain

Mutagenized tomato population produced by treating the tomato variety Micro-Tom (*Solanum lycopersicum*, cv. Micro-Tom) with ethylmethane sulfonate (EMS) at University of Tsukuba (Japan) was cultivated in a glass greenhouse at high temperatures in summer, and candidate heat-tolerant strains were selected. 91 strains exhibiting excellent fruit set were selected and seeds were collected therefrom. On the following year, 12 seeds per each of the selected 91 strains were seeded, cultivated in a greenhouse at high temperatures in summer in the same manner, for reevaluating in terms of heat tolerance. As a result, 16 strains exhibiting excellent fruit set at high temperatures were selected. In the both selection tests conducted, the maximal temperature during blooming exceeded 35° C. at which tomato fruit set would be significantly affected. Accordingly, it was considered that a sufficient level of high temperature stress was applied.

On the next year, the selected strains were quantitatively examined for the rate of fruit set and the yield at high temperatures in summer. On June 1, at the outset, 16 candidate heat-tolerant strains selected in the previous year were seeded. Thereafter, individual plants that had germinated and normally developed flowers were subjected to subsequent evaluation. At the initial stage of cultivation, windows of the glass greenhouse were kept fully open to suppress the temperature rise. From June 26 when development of a bud was observed, temperature in the greenhouse was controlled by opening and closing windows. From 2 weeks before blooming, daytime temperature in the greenhouse was allowed to exceed 35° C. to cultivate the strains under the high-temperature stress conditions (high-temperature conditions), and all the plants were then transferred to pots on July 19. Thereafter, cultivation was continued in the same greenhouse under high-temperature stress conditions, and cultivation was terminated after fruit set was observed and fruits were harvested.

Figure 2:
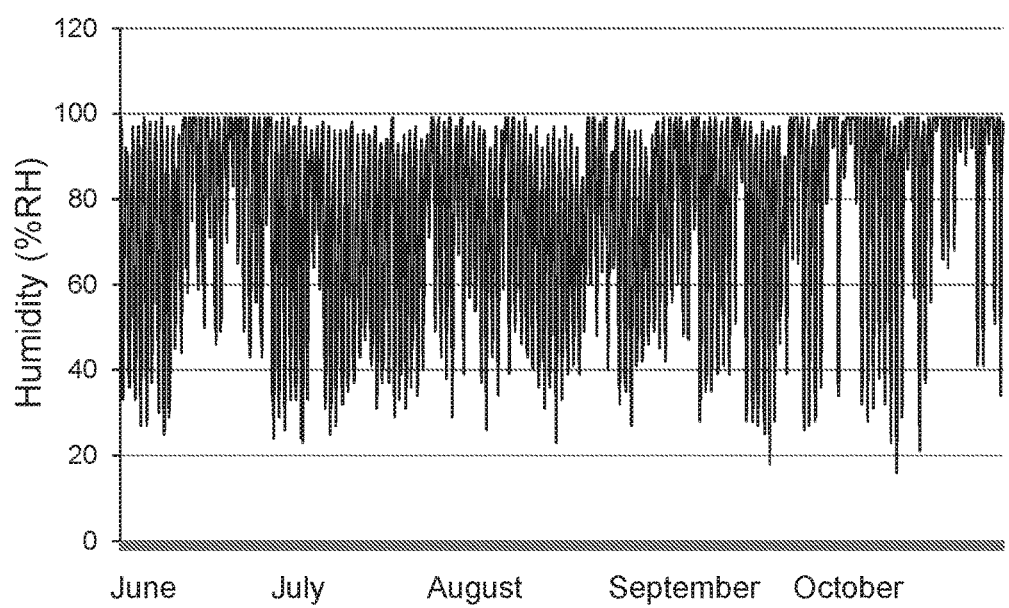
FIG. 2 shows changes in humidity in a greenhouse (Jun. 1 to Nov. 1, 2013).
Figure 3:
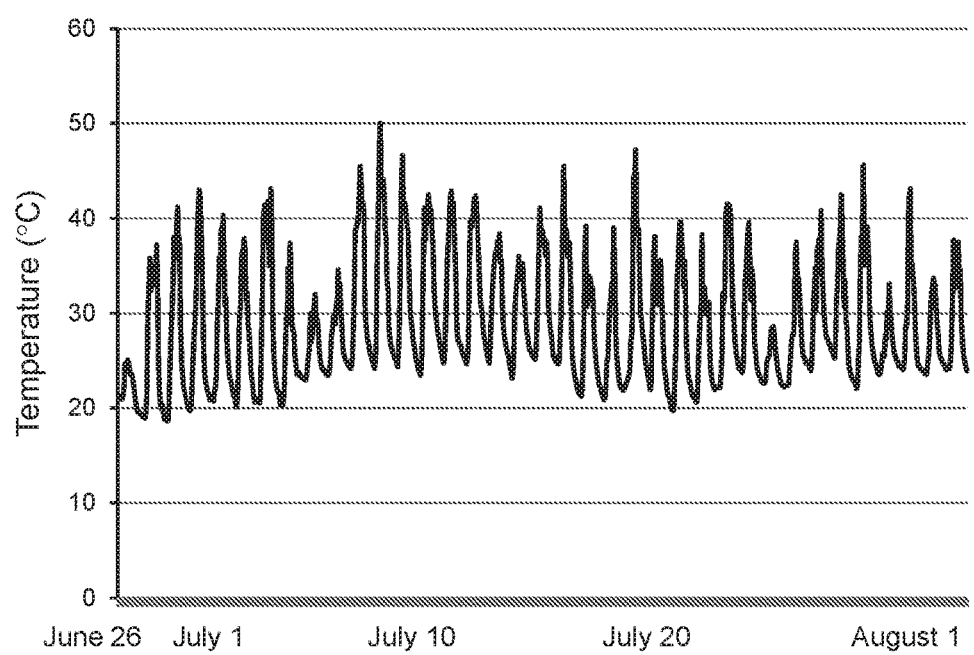
FIG. 3 shows changes in temperature in a greenhouse (Jun. 26 to Aug. 1, 2013).

FIGS. 1 and 2 show changes in temperature and humidity in the glass greenhouse from the initiation to termination of cultivation, respectively. FIG. 3 shows changes in temperature in the glass greenhouse over a period of about 1 month from June 26 when development of bud was observed.

(3) Examination of Properties of Candidate Heat-Tolerant Strains (Heat Tolerance Test)

(i) Examination of the rate of fruit set, the fruit yield, and the weight per fruit under high temperature conditions The tomato strains cultivated under high temperature conditions as described in (2) above were examined for the number of bloomed flower, the total number of fruit set, the rate of fruit set, the fruit yield, and the weight per fruit. Next, fruits were separated into groups depending on the presence or absence of seeds, and the rate of fruit set, the fruit yield, and the weight per fruit of each group were calculated.

The number of bloomed flower was determined by counting the number of flowers bloomed after the initiation of cultivation to October 3.

The total number of fruit set and the rate of fruit set were determined from October 1 to October 3. Specifically, the number of flowers that had achieved fruit set (i.e., the number of fruit set) among the flowers that had bloomed up to the day of examination was counted, and the rate of fruit set was calculated in accordance with the following formula:

Rate of fruit set (%)=number of fruit set/number of bloomed flower×100

Regarding the fruit yield, all the colored fruits that had completed enlargement were examined to determine the number and weights of the fruits, and the fruit yield (in total weight) per individual plant was determined on the basis of the number and weights of all fruits set per individual plant, and the mean yield of each strain (i.e., a mean fruit yield per individual plant) was determined.

In addition, the mean weight of fruit obtained in each individual plant was determined, the mean weight within each strain was determined, and the determined value was designated as the mean weight per fruit of each strain.

Upon completion of the fruit investigation conducted from October 13 to October 15, fruits were separated into groups depending on the presence or absence of seeds, and the total fruit weight and the number of fruits of the group of fruits containing one or more seeds and those of the group of seedless fruits were determined. In addition, the proportion (%) of the number of seed-containing fruits relative to the total number of fruits was determined. Further, the total weight was divided by the number of fruits, so that the mean weight per fruit of the group of seed-containing fruits and that of the group of seedless fruits were determined.

The same heat tolerance test under high temperature conditions as described above was also performed on the Micro-Tom wild-type (i.e., the tomato plant Micro-Tom that has not subjected to mutagenesis treatment).

As a result, a plurality of strains exhibiting the rate of fruit set superior to that of the wild-type plant were found. However, most of such strains exhibited a low yield of seed-containing fruits and these strains were considered to be parthenocarpic mutant strains. Only one strain exhibiting a high yield of seed-containing fruits was selected from among the strains exhibiting the excellent rate of fruit set. The selected one strain (i.e., JHT06 strain) had a particularly high level of heat tolerance.

The seeds of the obtained JHT06 strain from the tomato variety Micro-Tom (i.e., *Solanum lycopersicum*, cv. Micro-Tom) are deposited on Sep. 17, 2014 at the International Patent Organism Depositary of the National Institute of Technology and Evaluation (NITE-IPOD, #120, 2-5-8 Kazusakamatari, Kisarazu-shi, Chiba, Japan) under Accession Number FERM BP-22278 under the Budapest Treaty as an international deposit.

FIGS. 4 to 10 show the results of the heat tolerance tests of the JHT06 strain and the wild-type plant.

Figure 4:
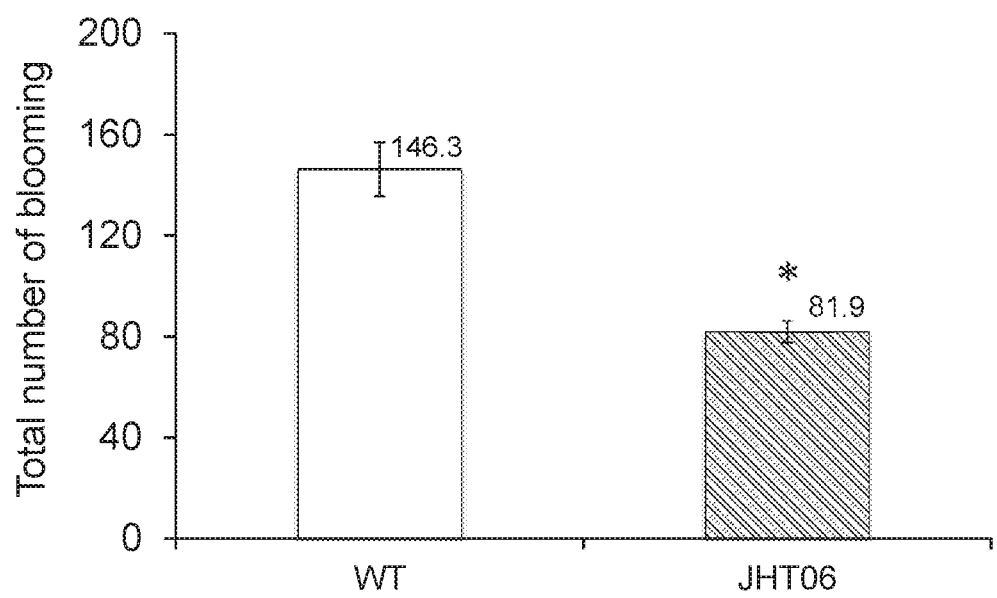
FIG. 4 shows the number of flowers bloomed after the initiation of cultivation up to Oct. 3, 2013. "*" indicates a statistically significant difference by t-test (P<0.05). "WT" indicates Micro-Tom wild-type and "JHT06" indicates JHT06 strain (the same applies herein below).
Figure 5A:
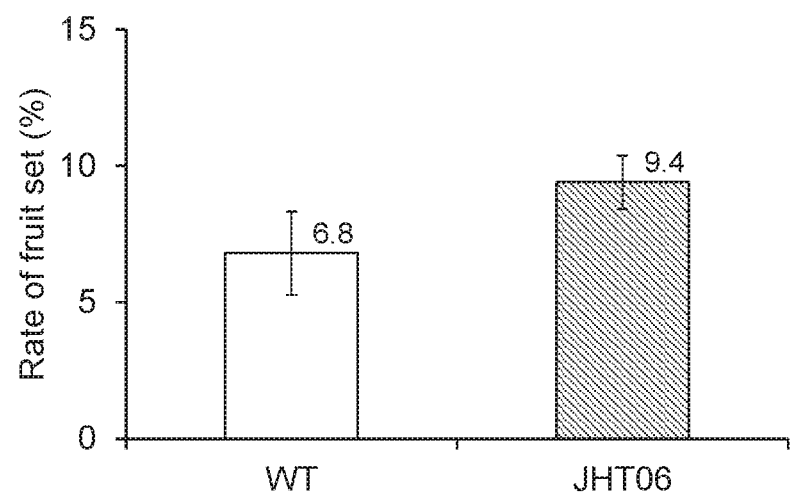
FIG. 5 shows a graph showing the rate of fruit set (FIG. 5A) and the total number of fruit set (FIG. 5B) of the Micro-Tom wild-type (WT) and the JHT06 strain (JHT06).
Figure 5B:
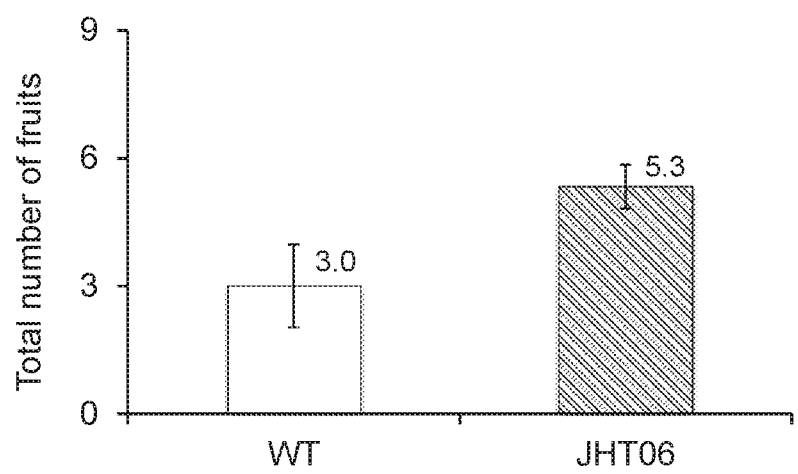

As shown in FIG. 4, the number of flowers of the JHT06 strain bloomed after the initiation of cultivation up to Oct. 3, 2013 was smaller than that of the wild-type plant. However, the JHT06 strain exhibited a higher rate of fruit set and the total number of fruit set than those of the wild-type plant (FIGS. 5A and 5B). The results demonstrate that the number of blooming flowers of the JHT06 strain is small, but the bloomed flowers develop fruits at a high rate.

Figure 6:
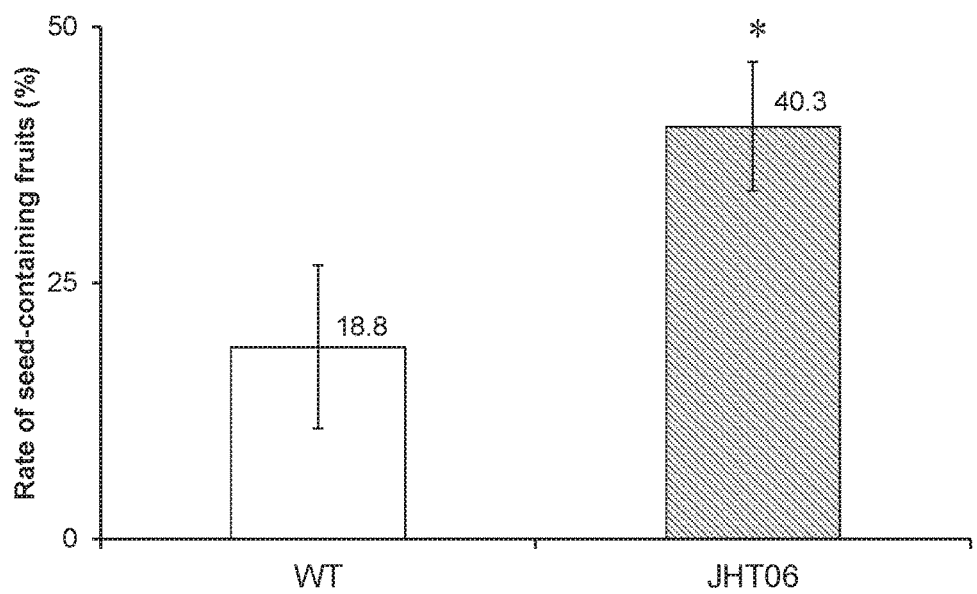
FIG. 6 shows the rate (%) of seed-containing fruits relative to the total number of fruits of WT and JHT06.
Figure 7A:
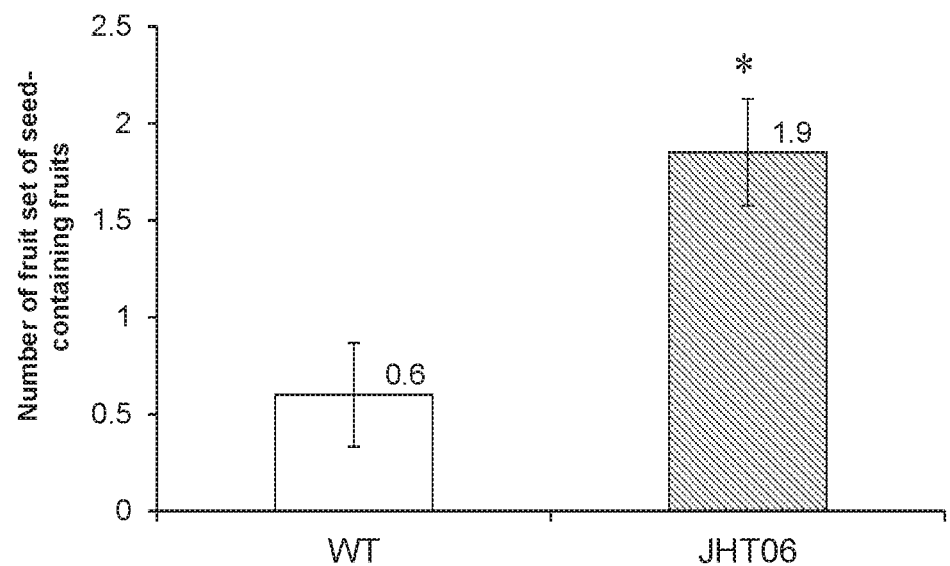
FIG. 7 shows the number of fruit set (FIG. 7A) and fruit yield (total weight.
FIG. 7B) of seed-containing fruits of WT and JHT06. "*" indicates a statistically significant difference by a t-test (P<0.05).
Figure 8:
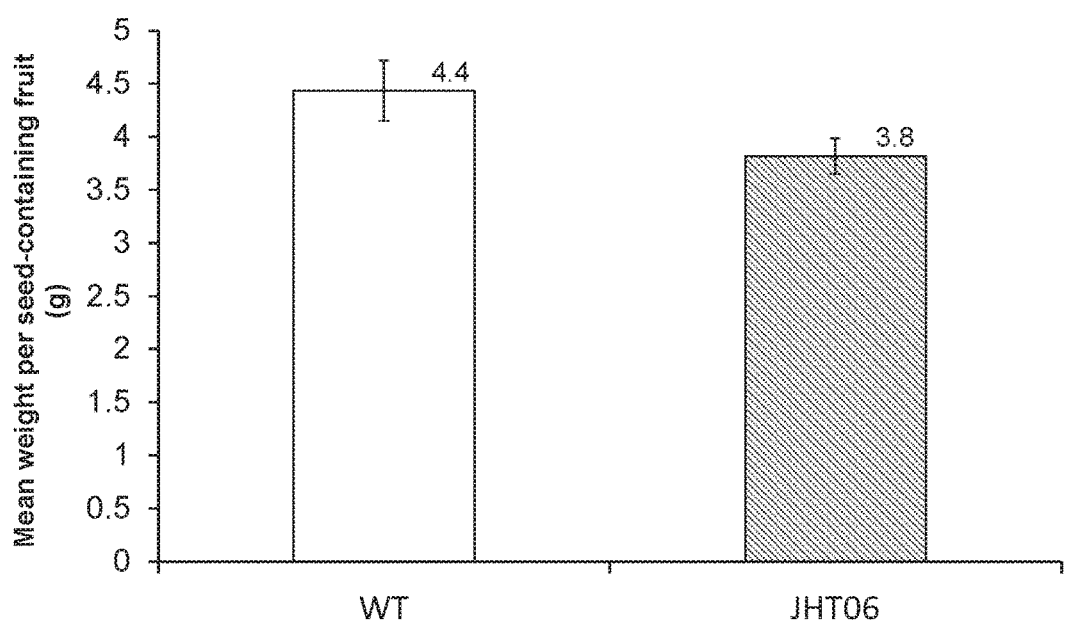
FIG. 8 shows the mean weight per fruit of seed-containing fruits of WT and JHT06.
Figure 9A:
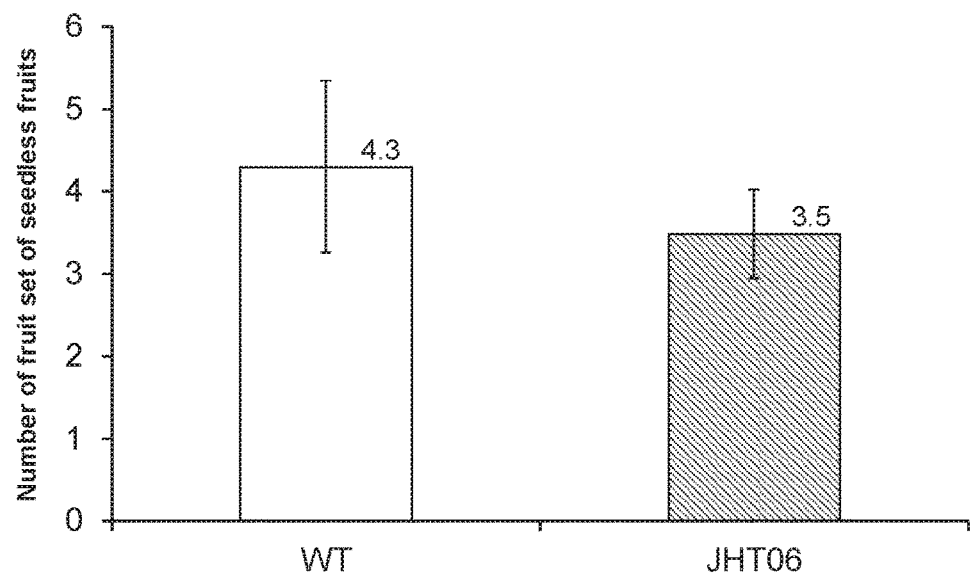
FIG. 9 shows the number of fruit set of seedless fruits (FIG. 9A) and the fruit yield (total weight.
FIG. 9B) of WT and JHT06.
Figure 9B:
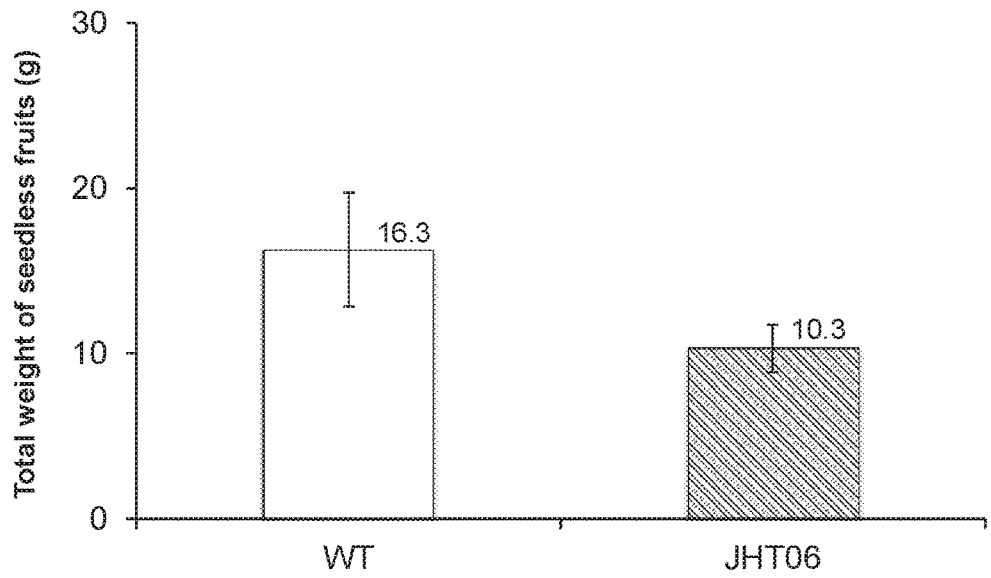
Figure 10:
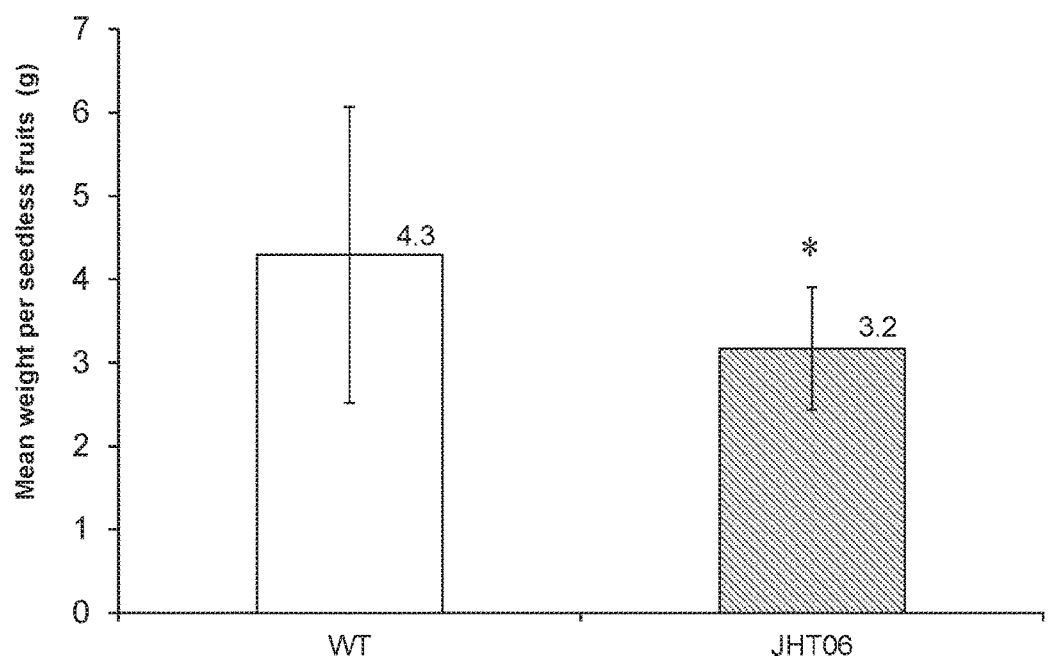
FIG. 10 shows the mean weight per fruit of seedless fruits of WT and JHT06. "*" indicates a statistically significant difference by t-test (P<0.05).

The JHT06 strain exhibited a significantly higher rate (proportion) of seed-containing fruits relative to the total number of fruits than the wild-type plant (FIG. 6). In addition, the JHT06 strain exhibited a greater number of fruit set of seed-containing fruits and a significantly greater yield of seed-containing fruits compared with the wild-type plant (FIGS. 7A and B). The mean weight per fruit of the seed-containing fruits of the JHT06 strain was approximately equivalent to that of the wild-type plant (FIG. 8). In contrast, the number of fruit set and the fruit yield of seedless fruits of the JHT06 strain were smaller than those of the wild-type plant (FIGS. 9A and 9B), and the mean weight per fruit of seedless fruits was approximately equivalent to that of the wild-type plant (FIG. 10). The results demonstrate that the JHT06 strain has a higher capacity for developing normal, seed-containing fruits than the wild-type plant under high temperature conditions.

Example 2

Pollen Fertility Test (1) Pollen Fertility Test Under High Temperature Conditions The high capacity of the JHT06 strain for developing seed-containing fruits under high temperature conditions is considered to result from the development of pollens maintaining high fertility even under high temperature conditions. Pollens of the JHT06 strain and the wild-type strain grown under high temperature conditions were stained with 2,3,5-triphenyltetrazolium chloride (TTC) which is used for assays of cellular respiration or metabolism activity, thereby determining the pollen viability. TTC staining is an indicator for cellular survival activity on the basis of mitochondrial reduction reactions, and living cells (living pollens herein) are stained red with TTC, while non-living cells are not stained.

The bloomed flowers were sampled from the JHT06 strain and the Micro-Tom wild-type grown under the conditions shown in FIGS. 1 to 3 in Example 1, and the pollens were examined on each day of blooming.

Anthers were removed from the flowers bloomed on the same day, soaked in a TTC solution (1% TTC (Wako Pure Chemical Industries, Ltd.) and 50% sucrose (Wako Pure Chemical Industries, Ltd.)), and shaken so as to disperse the pollens in the solution. Thereafter, the TTC solution containing pollens was allowed to stand in a dark room at 38° C. for 3 hours to stain the pollens. The TTC solution containing pollens was injected into a cell counter OneCell Counter (Biomedical Science). With the use of the System Microscope BX53 (Olympus Corporation), a field was designed to cover the total number of pollens of at least 200, the total number of pollens and the number of stained pollens among the total pollens were determined, and the pollen viability was determined using the following formula:

Pollen viability (%)=number of stained pollens/total number of pollens×100

As a result, for all strains, there were no living pollens developed in individuals that had been exposed to ultra-high-temperature conditions in which the maximal temperature in a greenhouse exceeded 45° C., for several hours or longer within a period from 2 weeks before blooming to the day of blooming. In the case of pollens developed in individuals that had been frequently exposed to high-temperature conditions in which the temperature in a greenhouse was 35° C. to 40° C., within a period from 2 weeks before blooming to the day of blooming, however, remarkable differences were observed in the pollen viability between the wild-type plant and the JHT06 strain, and a significant improvement in the pollen viability of the JHT06 strain was shown (FIG. 11).

Figure 7B:
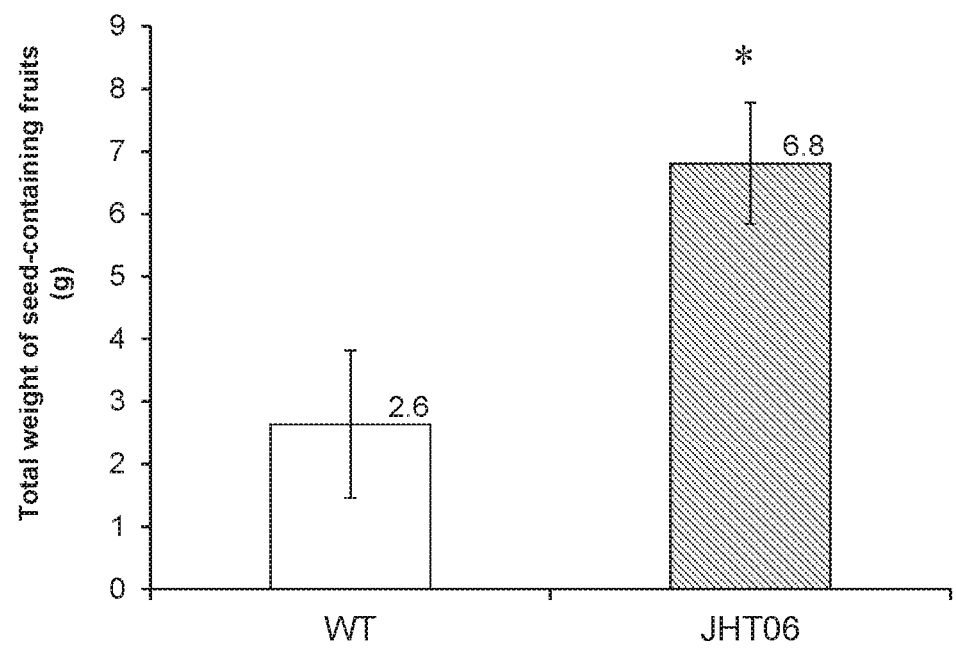
Figure 11:
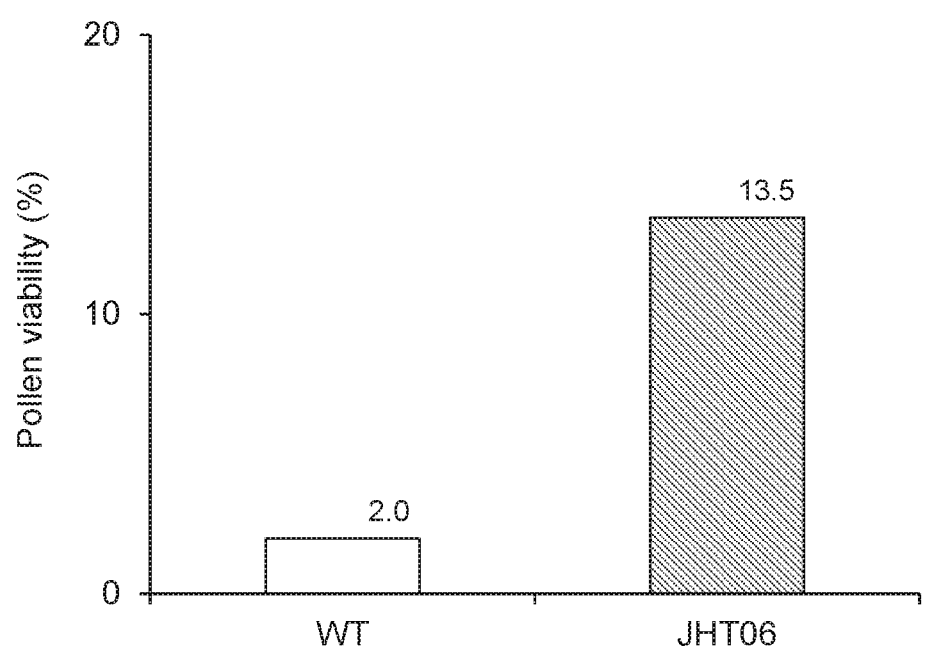
FIG. 11 shows the pollen viability of WT and JHT06 cultivated in a greenhouse.

The above results demonstrate that the JHT06 strain is a mutant that maintains a high pollen fertility even under high temperature conditions (FIGS. 6, 7, and 11). In the field of tomato production, cultivation is carried out while keeping greenhouse windows open and therefore temperature in a greenhouse is approximately 40° C. at a maximum. When cultivation is carried out under such environmental conditions, the JHT06 strain having a high pollen fertility is considered to exhibit a higher rate of fruit set and higher fruit yield than those of the wild-type plant.

(2) Pollen Fertility Test at Temperature Conditions of 35° C.

Subsequently, the influence of temperature conditions on the pollen fertility of the JHT06 strain and the Micro-Tom wild-type was examined under temperature-controlled conditions with the use of a containment plant cultivation room in which the temperature could be adjusted to 35° C.

A filter paper impregnated with distilled water was placed in a petri dish, and seeds were sown thereon. After 1 week of germination, normally germinated seedlings were transferred to hydroculture media Rockwool cubes (Grodan). High temperature conditions were set at the temperatures of 35° C. in the light and 25° C. in the dark and day-length conditions of 16 hours of daylight (60.0 µmol $m^{-2}s^{-1}$). Plants were grown via hydroculture. As with the case of cultivation in a greenhouse, flowers were vibrated with a vibrator to assist pollination. As a control, cultivation was carried out under the same conditions as described above, except that the conditions of temperature 25° C. and 16 hours of daylight (60.0 µmol $m^{-2}s^{-1}$) were used.

Subsequently, pollen fertilities of the wild-type and the JHT06 strain grown in the containment plant cultivation room were evaluated with the use of a TTC solution, in the same manner as in the pollen fertility test for the candidate heat-tolerant strain cultivated in the greenhouse described in (1) above.

At least 8 flowers that had bloomed on the same day were excised and pollens were collected therefrom. Only the living pollens were stained with the TTC solution, and the pollen viability and the total number of pollens were determined using the OneCell Counter, in the same manner as in the case of the pollen fertility test in a greenhouse. A field of the System Microscope BX53 is 1.05 mm×1.4 mm, and a thickness of the solution injection site of the OneCell Counter is designed to be 0.1 mm. The number of living pollens and the total number of pollens in 4 different fields were counted, the means thereof were determined, and the pollen density in liquid of the pollen suspension was then determined. The pollen density in liquid was multiplied by the amount (100 µl) of the TTC solution used for suspension per one flower to determine the number of stained pollens and the total number of pollens contained per flower, and the pollen viability was determined in the same manner as described above.

Figure 12A:
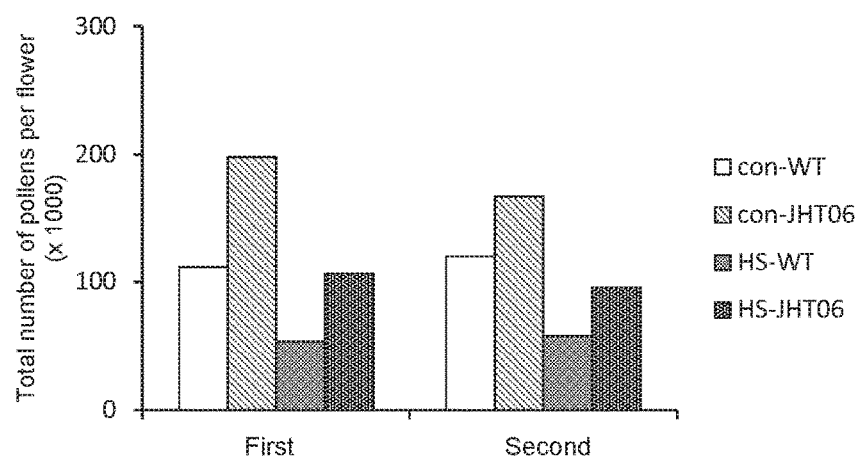
FIG. 12 shows the total number of pollens (FIG. 12A) and the pollen viability (the proportion of pollens maintaining fertility.
FIG. 12B) per flower of WT and JHT06 cultivated in the containment plant cultivation room. "con-WT" and "con-JHT06" indicate WT and JHT06 cultivated under the control, non-high temperature conditions (25° C. in the light, 16 hours of daylight, 60.0 μmol m$^{-2}$s$^{-1}$). "HS-WT" and "HS-JHT06" indicate WT and JHT06 cultivated under high temperature conditions (35° C. in the light/25° C. in the dark). The results of the first and the second experiments are shown.
Figure 12B:
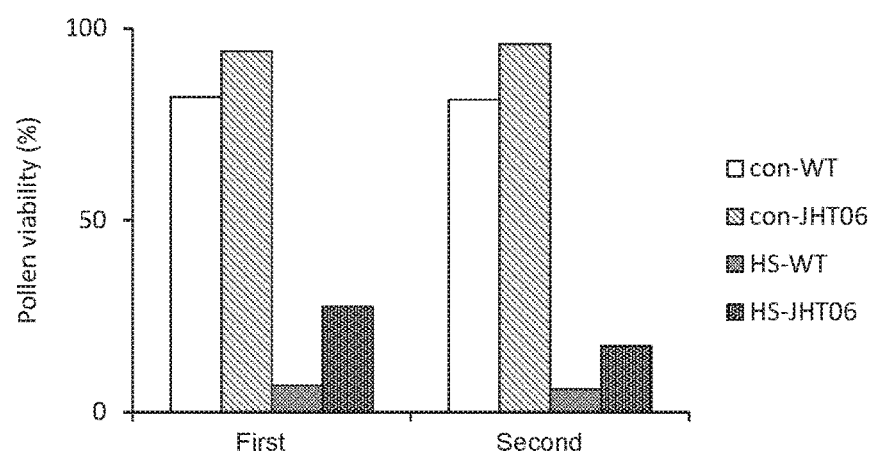

As a result, the total number of pollens of the wild-type plant under the high temperature conditions was remarkably reduced compared with the control under the non-high temperature conditions (FIG. 12A). The total number of pollens of the JHT06 strain under the high temperature conditions was also reduced compared with the control under the non-high temperature conditions, but larger than that of the wild-type plant (FIG. 12A). The pollen viability also shows a similar tendency to that in the total number of pollens; that is, the pollen viability of the JHT06 strain was higher than that of the wild-type plant (FIG. 12B).

It is known that stamen elongation is suppressed under high temperature conditions, the stamen becomes shorter, and normal pollination is inhibited. Accordingly, the stamen length was further examined. One stamen was excised from each of flowers bloomed on the same day, the length thereof was measured, and the mean among the flowers was determined.

Figure 13:
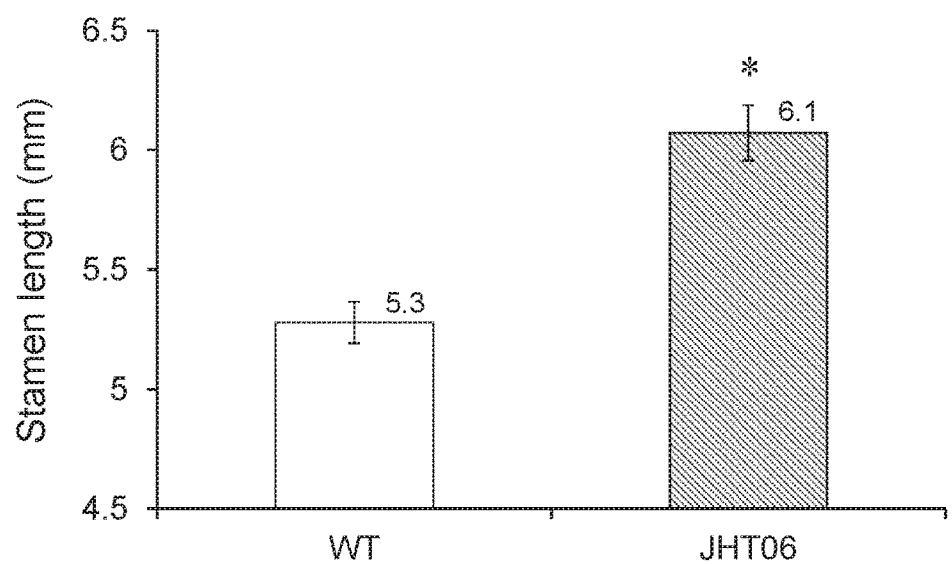
FIG. 13 shows the stamen length of WT and JHT06 cultivated in a containment plant cultivation room. "*" indicates a statistically significant difference (P<0.05) found by a t-test.

As a result, the stamen length of the JHT06 strain was shown to be significantly longer than that of the wile-type (FIG. 13). Accordingly, the JHT06 strain was shown to be less likely to exhibit pollination inhibition by suppression of stamen elongation under high-temperature conditions.

The results demonstrate that the JHT06 strain exhibits a large total number of pollens and a high pollen viability, which shows that the JHT06 strain has a high capacity for developing normal, seed-containing fruits even under high temperature conditions.

Example 3

Measurement of SPAD Level

The JHT06 strain was also characterized by its deeper green color of leaves. Thus, the wild-type and the JHT06 strain were evaluated by measuring the SPAD level as a chlorophyll content index.

The Micro-Tom wild-type and the JHT06 strain that had grown under the conditions shown in FIGS. 1 to 3 in Example 1 were subjected to measurement of leaf SPAD levels using a chlorophyll counter SPAD-502Plus (Konica Minolta Inc.) after 30, 40, 50, 60, 70, and 80 days of seeding. The leaf SPAD levels of all leaves except for cotyledons were measured after 30, 40, 50, 60, and 70 days of seeding. The leaf SPAD levels of randomly selected 20 leaves were measured after 80 days of seeding.

Figure 14:
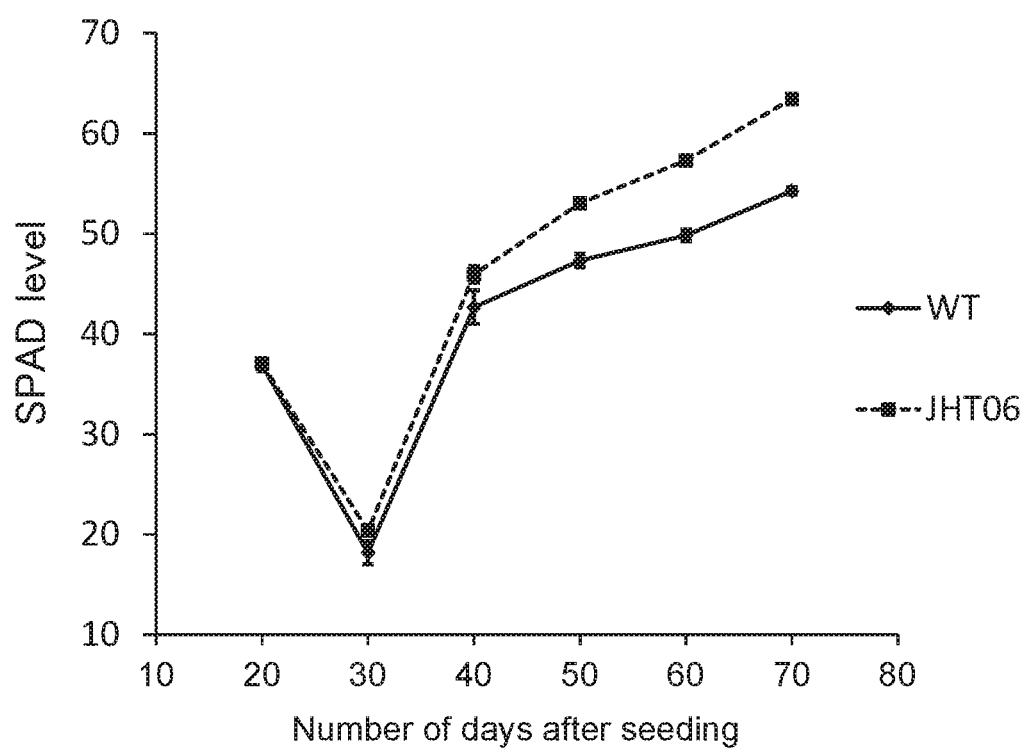
FIG. 14 shows a transition in SPAD levels of WT and JHT06. A solid line indicates WT and a dotted line indicates JHT06.

Nine individual plants per strain were subjected to the measurement of the SPAD levels, and the mean SPAD levels per individual plant were determined on the basis of the measured SPAD levels. As a result, a clear difference was observed between the wild-type and the JHT06 strain at the late stage of development (FIG. 14). The results confirmed the phenotype of the JHT06 strain such that the strain has leaves of deeper green. The results also indicate that substances having antioxidant activity, such as flavonoid, may accumulate in leaves of the JHT06 strain and impart a tolerance against high-temperature stress to the plant bodies.

Example 4

Whole Genome Analysis of JHT06 Strain Using Next-Generation Sequencer

The whole genome sequence of the JHT06 strain was determined and the mutant genes were analyzed. Genomic DNA of the JHT06 strain was extracted using the DNA purification kit (Maxwell® 16 DNA Purification Kits; Promega). Approximately 6 young leaves were excised from the JHT06 strain and placed in a 1.5-ml tube, followed by freezing with liquid nitrogen. The frozen leaves were thoroughly grounded with a micropestle, and the grounded leaves were placed in a cartridge containing a lysis buffer in the kit. The cartridge was set in the nucleic acid/protein automatic purifier Maxwell® 16 to extract genomic DNA. The extracted genomic DNA was dissolved in 400 µl of sterilized water, the total amount of genomic DNA was adjusted to 1 µg in terms of bulk, and the whole genome sequence of the JHT06 strain was then determined with a next-generation sequencer (HiSeq™ Sequence System, Illumina).

The determined sequence was compared with the reference whole genome sequence of the Micro-Tom wild-type for analysis. As a result, 186 mutation sites were found. Some mutation sites were found within a single gene, and, the number of genes having observed mutation(s) was 159. Among mutations (SNPs) observed in exons, 31 mutations would cause amino acid mutation and 26 sites among them were in genes of which functions would be deduced, and other 5 sites were in genes having unknown function.

In addition, 28 SNPs among the 31 SNPs found in the exon regions in the analysis with the next-generation sequencer described above were examined to determine the presence or absence of the SNPs in the genome of the JHT06 strain.

Genomic DNA of the JHT06 strain was extracted from the leaves in the same manner as described above. PCR amplification was carried out with the extracted genomic DNA as a template and primers designed to sandwich regions of approximately 500 bp before and after each of the 28 SNPs (Table 1). The PCR reaction solution (50 μl in total) contained 5.0 μl of 10×PCR buffer, 5 μl of 2 mM dNTPs, 2 μl of 25 mM MgSO$_4$, 2 μl of template DNA, 1 μl of DNA polymerase KOD-plus-, 1.5 μl each of primers, and 32 μl of ultrapure water. The PCR reaction was carried out at 94° C. for 2 minutes for initial thermal denaturation, followed by 35 cycles of 94° C. for 2 minutes, 55° C. for 30 seconds, and 68° C. for 1 minute per cycle. The amplified DNA was subjected to electrophoresis on 1.5% agarose gel to verify DNA amplification.

TABLE 1

|    | Primer name      | Primer sequence                         |    | Primer name      | Primer sequence                         |
|----|------------------|-----------------------------------------|----|------------------|-----------------------------------------|
| 1  | So04g071540 FW   | GGCTTTTCACAAGGATTGGA (SEQ ID NO: 1)     | 30 | So07g009010 RV   | TTGTATCAACAGCCCAGGGT (SEQ ID NO: 30)    |
| 2  | So04g071540 RV   | TCTCTGCAAAGCGATCATTG (SEQ ID NO: 2)     | 31 | So07g009190 FW   | ACGGAATTTGCTGCAGTTCT (SEQ ID NO: 31)    |
| 3  | So04g076040 FW   | CGTATCGGATCCTCCAAAAA (SEQ ID NO: 3)     | 32 | So07g009190 RV   | AGCTGCAAAACTTGGAAGGA (SEQ ID NO: 32)    |
| 4  | So04g076040 RV   | CAATGAGGACGATGATGTCG (SEQ ID NO: 4)     | 33 | So07g009210 FW   | GCTGCTTGGCCAACTAAGTC (SEQ ID NO: 33)    |
| 5  | So05g047650 FW   | TTTCCCTTGGATTTGCTTTG (SEQ ID NO: 5)     | 34 | So07g009210 RV   | TCAACTCCTTTGGGTGGAAC (SEQ ID NO: 34)    |
| 6  | So05g047650 RV   | TGGTAGGCCACCAACTTCTT (SEQ ID NO: 6)     | 35 | So07g043500 FW   | AGGTTGATGGTCGAAAATGG (SEQ ID NO: 35)    |
| 7  | So06g005540 FW   | GAAGAGACGGCAACCAAAAG (SEQ ID NO: 7)     | 36 | So07g043500 RV   | TCCCCAGATGATATTCAGCC (SEQ ID NO: 36)    |
| 8  | So06g005540 RV   | AAGAGAAGAGGGGCGAGAAG (SEQ ID NO: 8)     | 37 | So07g044720 FW   | GGTGGAGAGGAAAATATGAAAA A (SEQ ID NO: 37) |
| 9  | So06g005640 FW   | TGAGGGTCGAGCAACTAACA (SEQ ID NO: 9)     | 38 | So07g044720 RV   | TCCATAATTAAAAGACCCACTT GA (SEQ ID NO: 38) |
| 10 | So06g005640 RV   | ACCAACACCGACAACATTGA (SEQ ID NO: 10)    | 39 | So07g044940 FW   | AAAGACAAGGAAACAGGCGA (SEQ ID NO: 39)    |
| 11 | So06g005740 FW   | AATACATGCCCATTGCCTTC (SEQ ID NO: 11)    | 40 | So07g044940 RV   | TCAACCAATGCATCTTCTGC (SEQ ID NO: 40)    |
| 12 | So06g005740 RV   | AGACTGACCCATTCGGTGAC (SEQ ID NO: 12)    | 41 | So07g044940 FW   | AAAGACAAGGAAACAGGCGA (SEQ ID NO: 41)    |
| 13 | So6g05930-1 FW   | TGGTGAGACTTTGGAGAATGG (SEQ ID NO: 13)   | 42 | So07g044940 RV   | TCAACCAATGCATCTTCTGC (SEQ ID NO: 42)    |
| 14 | So6g05930-1 RV   | TTGGTCTTTGGGCTTTCATC (SEQ ID NO: 14)    | 43 | So07g044950 FW   | CCCACAGTTCATTGTTGCAT (SEQ ID NO: 43)    |
| 15 | So6g05930-2 FW   | TATTTCGGCCATTGCTTAGG (SEQ ID NO: 15)    | 44 | So07g044950 RV   | TCGATGGAGCAGGTATGACA (SEQ ID NO: 44)    |
| 16 | So6g05930-2 RV   | TTGGTCTTTGGGCTTTCATC (SEQ ID NO: 16)    | 45 | So07g061860 FW   | TTTGTGATAGGCTCGATTCAGA (SEQ ID NO: 45)  |
| 17 | So06g071730 FW   | TGTAAACCATTCATTTGCCTT T (SEQ ID NO: 17) | 46 | So07g061860 RV   | AGTCAACCACCTCCACATCC (SEQ ID NO: 46)    |
| 18 | So06g071730 RV   | GCGTTCCACGAGGTAAACAT (SEQ ID NO: 18)    | 47 | So08g078800 FW   | TGATTATGAAACCGCAACGA (SEQ ID NO: 47)    |
| 19 | So07g008460 FW   | TGTAGCTGAGACGTGGATCG (SEQ ID NO: 19)    | 48 | So08g078800 RV   | CCAGCCTAGCATTGAGAACA (SEQ ID NO: 48)    |
| 20 | So07g008460 RV   | TGGCTATGTGAACACCCAGA (SEQ ID NO: 20)    | 49 | So09g008110 FW   | GTTGACATGGTATGCCCCTC (SEQ ID NO: 49)    |
| 21 | So7g08640-1 FW   | TTGCCGAAAGGTCCAGTATC (SEQ ID NO: 21)    | 50 | So09g008110 RV   | TTTGTGAGGACTTGTTGCATT (SEQ ID NO: 50)   |
| 22 | So7g08640-1 RV   | GGGCCTTTACCACTAGTCCC (SEQ ID NO: 22)    | 51 | So11g051190 FW   | CTGGCTCAGGTATGCTCACA (SEQ ID NO: 51)    |

TABLE 1-continued

| | Primer name | Primer sequence | | Primer name | Primer sequence |
|---|---|---|---|---|---|
| 23 | So7g08640-2 FW | GATTCTGGAACCATATCGGAA (SEQ ID NO: 23) | 52 | So11g051190 RV | TGCTTGAAATTATCGGGAGG (SEQ ID NO: 52) |
| 24 | So7g08640-2 RV | TGTTCGTAGAGACATCGTTTG G (SEQ ID NO: 24) | 53 | So12g005420 FW | GAGGATAGGGCTTTGCTGTG (SEQ ID NO: 53) |
| 25 | So07g008790 FW | AAATGGATGGCTTCCAAGAA (SEQ ID NO: 25) | 54 | So12g005420 RV | GCGCGTAACAGAAGCATACA (SEQ ID NO: 54) |
| 26 | So07g008790 RV | TGACAACCCAAAATCTGCAA (SEQ ID NO: 26) | 55 | So12g040520 FW | TGGGGGCTGAATATTTATGG (SEQ ID NO: 55) |
| 27 | So07g008960 FW | AGGACTTGCATTTCGAGGTC (SEQ ID NO: 27) | 56 | So12g040520 RV | TCCAATTCGAAAACATCATCTC (SEQ ID NO: 56) |
| 28 | So07g008960 RV | TCACCTTGCATATTGCTTGC (SEQ ID NO: 28) | 57 | So12g044970 FW | GTCCTTGAGCAGCAGTGTGA (SEQ ID NO: 57) |
| 29 | So07g009010 FW | ATTTCGTACCCGAGAAGCCT (SEQ ID NO: 29) | 58 | So12g044970 RV | TGTTTAAAGACATACGGAAGTT GA (SEQ ID NO: 58) |

Each primer name corresponds to a relevant annotation shown in Table 2.
FW: a forward primer; RV: a reverse primer The amplified DNA was purified with the purification system (Wizard SV Gel and PCR Clean-Up System, Promega) and subjected to sequencing reaction, and the DNA sequence was determined and analyzed with the DNA sequencer (the 3500 Genetic Analyzer, Applied Biosystems), and the presence or absence of the above-mentioned SNPs in the genome of the JHT06 strain was examined.

As a result, 5 SNPs out of the 28 SNPs were verified to be present in the genome of the JHT06 strain (Table 2).

These 5 SNPs (Table 3) were considered to include a mutation that imparts the JHT06 strain with high heat tolerance, in particular, the high pollen viability, tolerance against stamen elongation suppression, and a high capacity for developing seed-containing fruits under high temperature conditions. In other words, a mutation in at least one gene from among the genes shown in Table 3 was considered to provide the JHT06 strain with a high degree of heat tolerance.

TABLE 2

| SNP No. | Chromosome No. | Mutation site in whole genome sequence | Gene No. | Annotation (gene name) | Presence of SNP sequence |
|---|---|---|---|---|---|
| 1 | 4 | 56,126,579 | Solyc04g071540.2.1 | Sterol 3-beta-glucosyltransferase | Absent |
| 2 | 4 | 58,599,784 | Solyc04g076040.2.1 | Cyclin d2 | Present |
| 3 | 5 | 58,282,365 | Solyc05g047650.1.1 | Unknown Protein | Absent |
| 4 | 6 | 580,426 | Solyc06g005540.1.1 | Unknown Protein | Present |
| 5 | 6 | 707,136 | Solyc06g005640.1.1 | Unknown Protein | — |
| 6 | 6 | 776,491 | Solyc06g005740.1.1 | Pumilio-like | Absent |
| 7 | 6 | 917,694 | Solyc06g005930.1.1 | Sensitivity to red light reduced protein 1 | Present |
| 8 | 6 | 917,710 | Solyc06g005930.1.1 | Sensitivity to red light reduced protein 1 | Present |
| 9 | 6 | 40,577,203 | Solyc06g071730.2.1 | Unknown Protein | Present |
| 10 | 7 | 3,374,471 | Solyc07g008460.2.1 | Histone-lysine N-methyltransferase | Absent |
| 11 | 7 | 3,579,611 | Solyc07g008640.1.1 | LRR receptor-like serine/threonine-protein kinase, RLP | Absent |
| 12 | 7 | 3,581,653 | Solyc07g008640.1.1 | LRR receptor-like serine/threonine-protein kinase, RLP | Absent |
| 13 | 7 | 3,766,809 | Solyc07g008790.1.1 | Cell division protein kinase 2 | Absent |
| 14 | 7 | 3,989,098 | Solyc07g008960.1.1 | Zinc finger MYM-type protein 1 | Absent |
| 15 | 7 | 4,009,065 | Solyc07g009010.1.1 | Unknown Protein | Absent |
| 16 | 7 | 4,243,488 | Solyc07g009190.1.1 | Nbs-lrr, resistance protein | Absent |
| 17 | 7 | 54,662,524 | Solyc07g043500.1.1 | UDP-glucosyltransferase | Absent |
| 18 | 7 | 55,076,777 | Solyc07g044720.1.1 | 3-hydroxyisobutyryl-CoA hydrolase | Absent |
| 19 | 7 | 55,319,044 | Solyc07g044940.1.1 | Ulp1 protease family C-terminal catalytic domain containing protein | — |
| 20 | 7 | 55,319,106 | Solyc07g044940.1.1 | Ulp1 protease family C-terminal catalytic domain containing protein | — |
| 21 | 7 | 55,321,489 | Solyc07g044950.1.1 | Mutator-like transposase IPR018289 MULE transposase, conserved domain | Absent |
| 22 | 7 | 61,988,144 | Solyc07g061860.1.1 | Lactoylglutathione lyase-like | Absent |
| 23 | 8 | 59,683,243 | Solyc08g078800.1.1 | GRAS family transcription factor domain(s) IPR005202 GRAS transcription factor | Absent |
| 24 | 9 | 1,587,419 | Solyc09g008110.1.1 | Mutator-like transposase | Absent |
| 25 | 11 | 42,903,825 | Solyc11g051190.1.1 | Unknown Protein | Absent |
| 26 | 12 | 252,432 | Solyc12g005420.1.1 | Zinc finger protein CONSTANS-LIKE 3 | Absent |

TABLE 2-continued

| SNP No. | Chromosome No. | Mutation site in whole genome sequence | Gene No. | Annotation (gene name) | Presence of SNP sequence |
|---|---|---|---|---|---|
| 27 | 12 | 39,623,755 | Solyc12g040520.1.1 | Katanin p60 ATPase-containing subunit | Absent |
| 28 | 12 | 45,785,966 | Solyc12g044970.1.1 | Ulp1 protease family C-terminal catalytic domain containing protein | — |

"—" indicates that accurate determination could not be made.

Table 3 shows information of 5 SNPs that were verified to exist in the genome of the JHT06 strain. SNP numbers in Table 3 correspond to SNP numbers in Table 2. Table 3 also shows SEQ ID NOs of the SNPs-containing DNA sequences determined and analyzed above from the JHT06 strain, which is a mutant of the tomato variety Micro-Tom (i.e., the Micro-Tom mutant sequences). In Table 3, each SNP and amino acid mutation are indicated on the basis of the positions in the relevant reference sequences that are the full-length sequences of the corresponding genes and the amino acid sequences of the tomato variety Heinz1706 (wild-type) (SEQ ID NOs thereof are shown in Table 3), respectively. The wild-type (before mutation) nucleotides and amino acids at those mutation sites were conserved compared to the genome sequence of the tomato variety Heinz 1706 (*Solanum lycopersicum* cv. Heinz 1706). Gene numbers shown in Tables 2 and 3 can be retrieved from the database Sol genomics network (http://solgenomics.net).

gene of Solyc06g005930.1.1 and the amino acid sequence encoded thereby are shown by SEQ ID NOs: 75 and 76, respectively, and the CDS sequence of the corresponding wild-type gene and the amino acid sequence encoded thereby are set forth in SEQ ID NOs: 77 and 78, respectively. The CDS sequence determined for the mutant gene of Solyc06g071730.2.1 and the amino acid sequence encoded thereby are set forth in SEQ ID NOs: 79 and 80, respectively, and the CDS sequence of the corresponding wild-type gene and the amino acid sequence encoded thereby are set forth in SEQ ID NOs: 81 and 82, respectively. The CDS sequence determined for the mutant gene of Solyc04g076040.2.1 and the amino acid sequence encoded thereby are set forth in SEQ ID NOs: 83 and 84, respectively, and the CDS sequence of the corresponding wild-type gene and the amino acid sequence encoded thereby are shown in SEQ ID NOs: 85 and 86, respectively.

TABLE 3

| SNP No. | Gene No. | Gene name | Micro-Tom mutant sequence (SEQ ID NO:) | SNP | Amino acid mutation | Heinz1706 corresponding gene/ amino acid sequence (SEQ ID NO:) |
|---|---|---|---|---|---|---|
| 2 | Solyc04g076040.2.1 | Cyclin d2 | 59 | G181T | D61Y | 63/64 |
| 4 | Solyc06g005540.1.1 | Unknown Protein | 60 | T2C | M1T | 65/66 |
| 7 | Solyc06g005930.1.1 | Sensitivity to red light reduced protein 1; SSR1 | 61 | C334T | Q112* | 67/68 |
| 8 | Solyc06g005930.1.1 | Sensitivity to red light reduced protein 1; SSR1 | 61 | T350G | L117* | 67/68 |
| 9 | Solyc06g071730.2.1 | Unknown Protein | 62 | A306T | *102C | 69/70 |

*for amino acid mutation indicates the generation of a stop codon.

In Table 3, for example, Solyc06g005930.1.1 gene (sensitivity to red light reduced protein 1 gene) can be a responsible gene for high heat tolerance of the JHT06 strain. The gene is an ortholog of the *Arabidopsis thaliana* SSR1 (sensitivity to red light reduced protein 1) gene, which has been researched in *Arabidopsis thaliana*. *Arabidopsis thaliana* SSR1 is known to be associated with the circadian rhythm and photosynthesis (Staiger D., 2003, Gene & Development 17: pp. 256-268).

Example 5

The 4 genes shown in Table 3 in which the presence of SNPs had been confirmed in Example 4 (the mutant genes of the JHT06 strain) were subjected to sequence determination and mutation analysis again in the same manner as in Example 4. In addition, the nucleotide sequences of the corresponding wild-type genes (from the Micro-Tom wild-type) were determined. The CDS sequence determined for the mutant gene of Solyc06g005540.1.1 and the amino acid sequence encoded thereby are shown by SEQ ID NOs: 71 and 72, respectively, and the CDS sequence of the corresponding wild-type gene and the amino acid sequence encoded thereby are set forth in SEQ ID NOs: 73 and 74, respectively. The CDS sequence determined for the mutant As a result, all the SNPs shown in Table 3 (Example 4) were detected and reproducibility of these SNPs was confirmed.

In the analysis, in addition, many novel mutations were found in Solyc06g005540.1.1 and Solyc06g005930.1.1 genes, and the reproducibility thereof was also confirmed.

Table 4 shows the identified important mutations.

TABLE 4

| Gene No. | Nucleotide mutation | Amino acid mutation | Nucleotide sequence/ amino acid sequence (SEQ ID NOs) of full-length gene of JHT06 strain determined in this Examples |
|---|---|---|---|
| Solyc06g005540.1.1 | T2C | Lack of initiation codon | 71/72 |
| Solyc06g005540.1.1 | Deletion of positions 51-63 | Frameshift | |
| Solyc06g005540.1.1 | T115A102 | Y39*34 | |

TABLE 4-continued

| Gene No. | Nucleotide mutation | Amino acid mutation | Nucleotide sequence/ amino acid sequence (SEQ ID NOs) of full-length gene of JHT06 strain determined in this Examples |
|---|---|---|---|
| Solyc06g005930.1.1 | Insertion of glycine at position 158 | Frameshift and generation of stop codon | 75/76 |

*for amino acid mutation indicates the generation of a stop codon.

In the mutant gene of Solyc06g005540.1.1 (SEQ ID NO: 71), as shown in Table 4, thymine at position 2 in the corresponding wild-type gene sequence (SEQ ID NO: 73) had been substituted with cytosine (C). Due to this nucleotide substitution, the initiation codon ATG had been mutated into ACG in the mutant gene sequence. It was considered that the genetic mutation causes a mutation from methionine at position 1 in the wild-type amino acid sequence into threonine at position 1 in the mutant amino acid sequence, and thus the mutated gene is not translated because of the lack of the initiation methionine (initiation codon), and the Solyc06g005540.1.1 gene had lost its functions. Further, deletion of a 13-bp (positions 51 to 63) and nucleotide substitution T115A102 were detected in the mutant gene sequence of Solyc06g005540.1.1. The positions of the deletion site of the 13-bp (positions 51 to 63) are based on the nucleotide sequence of the wild-type gene (SEQ ID NO: 73). T115A102 means that thymine at position 115 on the nucleotide sequence of the wild-type gene was substituted with alanine at position 102 on the nucleotide sequence of the gene (mutant gene) of the JHT06 strain. The difference between the positions of the mutation sites results from the deletion of the 13-bp as described above. The deletion of the 13-bp causes a frameshift, and the nucleotide substitution T115A102 generates a stop codon to stop translation of the subsequent amino acid sequence. Accordingly, the Solyc06g005540.1.1 gene of the JHT06 strain was considered to have lost its functions also in view of the presence of these mutations.

In the mutant gene of Solyc06g005930.1.1 (SSR1 gene), glycine (G) was inserted at position 158 (in the second exon) on the nucleotide sequence of the wild-type gene (SEQ ID NO: 77). The insert causes a frameshift in the subsequent nucleotide sequence, and generates a stop codon TGA at a position corresponding to position 56 in the amino acid sequence to stop translation of the subsequent amino acid sequence. Accordingly, the Solyc06g005930.1.1 gene (SSR1 gene) of the JHT06 strain was considered to have lost its functions. In the mutant SSR1 gene, many nucleotide substitutions causing amino acid substitutions were observed in a region from positions 149 to 163 in the wild-type nucleotide sequence (SEQ ID NO: 77). In addition, many stop codons were generated after the stop codon at position 56. Also from this, the Solyc06g005930.1.1 gene (SSR1 gene) of the JHT06 strain is considered to have lost its functions.

The Solyc06g005930.1.1 gene (SSR1 gene) encodes a sensitivity to red light reduced protein. Accordingly, it is considered that deletion of such gene would change the circadian rhythm of a plant, thereby imparting the plant with heat tolerance.

INDUSTRIAL APPLICABILITY

Using the present invention, a tomato plant that is excellent in heat tolerance can be produced. For example, the use of the heat-tolerant tomato mutant of the present invention as a breeding material enables efficient production of tomato varieties capable of producing stable fruit quality and yield in summer tomato cultivation.

All publications, patents, and patent applications cited herein are incorporated herein by reference in their entirety.
Sequence Listing Free Text
SEQ ID NOs: 1 to 58: primers

What is claimed is:

1. A heat-tolerant tomato plant of species *Solanum lycopersicum* comprising genetic mutations of (i) to (iv):
   (i) a nucleotide mutation causing amino acid mutation D61Y as defined on the basis of the reference amino acid sequence as shown in SEQ ID NO: 64:
   (ii) a nucleotide mutation causing a loss-of-function of the gene comprising the nucleotide sequence of SEQ ID NO: 65;
   (iii) a nucleotide mutation causing a loss-of-function of the gene comprising the nucleotide sequence of SEQ ID NO: 67; and
   (iv) a nucleotide mutation causing amino acid mutation *102C, wherein * indicates the generation of a stop codon, as defined on the basis of the reference amino acid sequence as shown in SEQ ID NO: 70.

2. The heat-tolerant tomato plant according to claim 1, wherein the heat-tolerant plant is JHT06, a sample of seed having been deposited under Accession number FERM BP-22278.

3. A method for producing a heat-tolerant tomato plant, the method comprising crossing the heat-tolerant tomato plant according to claim 1 with itself or with another tomato plant and obtaining a progeny tomato plant having the mutations.

4. A method for producing a heat-tolerant tomato plant, the method comprising crossing the heat-tolerant tomato plant according to claim 2 with itself or with another tomato plant and obtaining a progeny tomato plant having the mutations.

5. A progeny plant produced by the method of claim 4, wherein the plant comprises the mutations.

6. The heat-tolerant tomato plant according to claim 1, wherein:
   a) the nucleotide mutation of (i) is G181T as defined on the basis of the reference nucleotide sequence as shown in SEQ ID NO: 63;
   b) the nucleotide mutation of (ii) is T2C as defined on the basis of the reference nucleotide sequence as shown in SEQ ID NO: 65;
   c) the nucleotide mutation of (iii) generates a premature stop codon; and
   d) the nucleotide sequence of (iv) is A306T as defined on the basis of the reference nucleotide sequence as shown in SEQ ID NO: 69.

* * * * *

SEQUENCE LISTING

```
<160> NUMBER OF SEQ ID NOS: 86

<210> SEQ ID NO 1
<211> LENGTH: 20
<212> TYPE: DNA
<213> ORGANISM: Artificial
<220> FEATURE:
<223> OTHER INFORMATION: primer

<400> SEQUENCE: 1
ggcttttcac aaggattgga                                                   20

<210> SEQ ID NO 2
<211> LENGTH: 20
<212> TYPE: DNA
<213> ORGANISM: Artificial
<220> FEATURE:
<223> OTHER INFORMATION: primer

<400> SEQUENCE: 2
tctctgcaaa gcgatcattg                                                   20

<210> SEQ ID NO 3
<211> LENGTH: 20
<212> TYPE: DNA
<213> ORGANISM: Artificial
```

<220> FEATURE:
<223> OTHER INFORMATION: primer

<400> SEQUENCE: 3
cgtatcggat cctccaaaaa                                              20

<210> SEQ ID NO 4
<211> LENGTH: 20
<212> TYPE: DNA
<213> ORGANISM: Artificial
<220> FEATURE:
<223> OTHER INFORMATION: primer

<400> SEQUENCE: 4
caatgaggac gatgatgtcg                                              20

<210> SEQ ID NO 5
<211> LENGTH: 20
<212> TYPE: DNA
<213> ORGANISM: Artificial
<220> FEATURE:
<223> OTHER INFORMATION: primer

<400> SEQUENCE: 5
tttcccttgg atttgctttg                                              20

<210> SEQ ID NO 6
<211> LENGTH: 20
<212> TYPE: DNA
<213> ORGANISM: Artificial
<220> FEATURE:
<223> OTHER INFORMATION: primer

<400> SEQUENCE: 6
tggtaggcca ccaacttctt                                              20

<210> SEQ ID NO 7
<211> LENGTH: 20
<212> TYPE: DNA
<213> ORGANISM: Artificial
<220> FEATURE:
<223> OTHER INFORMATION: primer

<400> SEQUENCE: 7
gaagagacgg caaccaaaag                                              20

<210> SEQ ID NO 8
<211> LENGTH: 20
<212> TYPE: DNA
<213> ORGANISM: Artificial
<220> FEATURE:
<223> OTHER INFORMATION: primer

<400> SEQUENCE: 8
aagagaagag gggcgagaag                                              20

<210> SEQ ID NO 9
<211> LENGTH: 20
<212> TYPE: DNA
<213> ORGANISM: Artificial
<220> FEATURE:
<223> OTHER INFORMATION: primer

<400> SEQUENCE: 9
tgagggtcga gcaactaaca                                              20

```
<210> SEQ ID NO 10
<211> LENGTH: 20
<212> TYPE: DNA
<213> ORGANISM: Artificial
<220> FEATURE:
<223> OTHER INFORMATION: primer

<400> SEQUENCE: 10
accaacaccg acaacattga                                              20

<210> SEQ ID NO 11
<211> LENGTH: 20
<212> TYPE: DNA
<213> ORGANISM: Artificial
<220> FEATURE:
<223> OTHER INFORMATION: primer

<400> SEQUENCE: 11
aatacatgcc cattgccttc                                              20

<210> SEQ ID NO 12
<211> LENGTH: 20
<212> TYPE: DNA
<213> ORGANISM: Artificial
<220> FEATURE:
<223> OTHER INFORMATION: primer

<400> SEQUENCE: 12
agactgaccc attcggtgac                                              20

<210> SEQ ID NO 13
<211> LENGTH: 21
<212> TYPE: DNA
<213> ORGANISM: Artificial
<220> FEATURE:
<223> OTHER INFORMATION: primer

<400> SEQUENCE: 13
tggtgagact ttggagaatg g                                            21

<210> SEQ ID NO 14
<211> LENGTH: 20
<212> TYPE: DNA
<213> ORGANISM: Artificial
<220> FEATURE:
<223> OTHER INFORMATION: primer

<400> SEQUENCE: 14
ttggtctttg ggctttcatc                                              20

<210> SEQ ID NO 15
<211> LENGTH: 20
<212> TYPE: DNA
<213> ORGANISM: Artificial
<220> FEATURE:
<223> OTHER INFORMATION: primer

<400> SEQUENCE: 15
tatttcggcc attgcttagg                                              20

<210> SEQ ID NO 16
<211> LENGTH: 20
<212> TYPE: DNA
<213> ORGANISM: Artificial
<220> FEATURE:
<223> OTHER INFORMATION: primer
```

```
<400> SEQUENCE: 16
ttggtctttg ggctttcatc                                               20

<210> SEQ ID NO 17
<211> LENGTH: 23
<212> TYPE: DNA
<213> ORGANISM: Artificial
<220> FEATURE:
<223> OTHER INFORMATION: primer

<400> SEQUENCE: 17
tgtaaaccat tcattttgcc ttt                                           23

<210> SEQ ID NO 18
<211> LENGTH: 20
<212> TYPE: DNA
<213> ORGANISM: Artificial
<220> FEATURE:
<223> OTHER INFORMATION: primer

<400> SEQUENCE: 18
gcgttccacg aggtaaacat                                               20

<210> SEQ ID NO 19
<211> LENGTH: 20
<212> TYPE: DNA
<213> ORGANISM: Artificial
<220> FEATURE:
<223> OTHER INFORMATION: primer

<400> SEQUENCE: 19
tgtagctgag acgtggatcg                                               20

<210> SEQ ID NO 20
<211> LENGTH: 20
<212> TYPE: DNA
<213> ORGANISM: Artificial
<220> FEATURE:
<223> OTHER INFORMATION: primer

<400> SEQUENCE: 20
tggctatgtg aacacccaga                                               20

<210> SEQ ID NO 21
<211> LENGTH: 20
<212> TYPE: DNA
<213> ORGANISM: Artificial
<220> FEATURE:
<223> OTHER INFORMATION: primer

<400> SEQUENCE: 21
ttgccgaaag gtccagtatc                                               20

<210> SEQ ID NO 22
<211> LENGTH: 20
<212> TYPE: DNA
<213> ORGANISM: Artificial
<220> FEATURE:
<223> OTHER INFORMATION: primer

<400> SEQUENCE: 22
gggcctttac cactagtccc                                               20
```

```
<210> SEQ ID NO 23
<211> LENGTH: 21
<212> TYPE: DNA
<213> ORGANISM: Artificial
<220> FEATURE:
<223> OTHER INFORMATION: primer

<400> SEQUENCE: 23
gattctggaa ccatatcgga a                                              21

<210> SEQ ID NO 24
<211> LENGTH: 22
<212> TYPE: DNA
<213> ORGANISM: Artificial
<220> FEATURE:
<223> OTHER INFORMATION: primer

<400> SEQUENCE: 24
tgttcgtaga gacatcgttt gg                                             22

<210> SEQ ID NO 25
<211> LENGTH: 20
<212> TYPE: DNA
<213> ORGANISM: Artificial
<220> FEATURE:
<223> OTHER INFORMATION: primer

<400> SEQUENCE: 25
aaatggatgg cttccaagaa                                                20

<210> SEQ ID NO 26
<211> LENGTH: 20
<212> TYPE: DNA
<213> ORGANISM: Artificial
<220> FEATURE:
<223> OTHER INFORMATION: primer

<400> SEQUENCE: 26
tgacaaccca aaatctgcaa                                                20

<210> SEQ ID NO 27
<211> LENGTH: 20
<212> TYPE: DNA
<213> ORGANISM: Artificial
<220> FEATURE:
<223> OTHER INFORMATION: primer

<400> SEQUENCE: 27
aggacttgca tttcgaggtc                                                20

<210> SEQ ID NO 28
<211> LENGTH: 20
<212> TYPE: DNA
<213> ORGANISM: Artificial
<220> FEATURE:
<223> OTHER INFORMATION: primer

<400> SEQUENCE: 28
tcaccttgca tattgcttgc                                                20

<210> SEQ ID NO 29
<211> LENGTH: 20
<212> TYPE: DNA
<213> ORGANISM: Artificial
<220> FEATURE:
<223> OTHER INFORMATION: primer
```

<400> SEQUENCE: 29
atttcgtacc cgagaagcct                                                    20

<210> SEQ ID NO 30
<211> LENGTH: 20
<212> TYPE: DNA
<213> ORGANISM: Artificial
<220> FEATURE:
<223> OTHER INFORMATION: primer

<400> SEQUENCE: 30
ttgtatcaac agcccagggt                                                    20

<210> SEQ ID NO 31
<211> LENGTH: 20
<212> TYPE: DNA
<213> ORGANISM: Artificial
<220> FEATURE:
<223> OTHER INFORMATION: primer

<400> SEQUENCE: 31
acggaatttg ctgcagttct                                                    20

<210> SEQ ID NO 32
<211> LENGTH: 20
<212> TYPE: DNA
<213> ORGANISM: Artificial
<220> FEATURE:
<223> OTHER INFORMATION: primer

<400> SEQUENCE: 32
agctgcaaaa cttggaagga                                                    20

<210> SEQ ID NO 33
<211> LENGTH: 20
<212> TYPE: DNA
<213> ORGANISM: Artificial
<220> FEATURE:
<223> OTHER INFORMATION: primer

<400> SEQUENCE: 33
gctgcttggc caactaagtc                                                    20

<210> SEQ ID NO 34
<211> LENGTH: 20
<212> TYPE: DNA
<213> ORGANISM: Artificial
<220> FEATURE:
<223> OTHER INFORMATION: primer

<400> SEQUENCE: 34
tcaactcctt tgggtggaac                                                    20

<210> SEQ ID NO 35
<211> LENGTH: 20
<212> TYPE: DNA
<213> ORGANISM: Artificial
<220> FEATURE:
<223> OTHER INFORMATION: primer

<400> SEQUENCE: 35
aggttgatgg tcgaaaatgg                                                    20

```
<210> SEQ ID NO 36
<211> LENGTH: 20
<212> TYPE: DNA
<213> ORGANISM: Artificial
<220> FEATURE:
<223> OTHER INFORMATION: primer

<400> SEQUENCE: 36
tccccagatg atattcagcc                                               20

<210> SEQ ID NO 37
<211> LENGTH: 23
<212> TYPE: DNA
<213> ORGANISM: Artificial
<220> FEATURE:
<223> OTHER INFORMATION: primer

<400> SEQUENCE: 37
ggtggagagg aaaatatgaa aaa                                           23

<210> SEQ ID NO 38
<211> LENGTH: 24
<212> TYPE: DNA
<213> ORGANISM: Artificial
<220> FEATURE:
<223> OTHER INFORMATION: primer

<400> SEQUENCE: 38
tccataatta aaagacccac ttga                                          24

<210> SEQ ID NO 39
<211> LENGTH: 20
<212> TYPE: DNA
<213> ORGANISM: Artificial
<220> FEATURE:
<223> OTHER INFORMATION: primer

<400> SEQUENCE: 39
aaagacaagg aaacaggcga                                               20

<210> SEQ ID NO 40
<211> LENGTH: 20
<212> TYPE: DNA
<213> ORGANISM: Artificial
<220> FEATURE:
<223> OTHER INFORMATION: primer

<400> SEQUENCE: 40
tcaaccaatg catcttctgc                                               20

<210> SEQ ID NO 41
<211> LENGTH: 20
<212> TYPE: DNA
<213> ORGANISM: Artificial
<220> FEATURE:
<223> OTHER INFORMATION: primer

<400> SEQUENCE: 41
aaagacaagg aaacaggcga                                               20

<210> SEQ ID NO 42
<211> LENGTH: 20
<212> TYPE: DNA
<213> ORGANISM: Artificial
<220> FEATURE:
<223> OTHER INFORMATION: primer
```

```
<400> SEQUENCE: 42
tcaaccaatg catcttctgc                                          20

<210> SEQ ID NO 43
<211> LENGTH: 20
<212> TYPE: DNA
<213> ORGANISM: Artificial
<220> FEATURE:
<223> OTHER INFORMATION: primer

<400> SEQUENCE: 43
cccacagttc attgttgcat                                          20

<210> SEQ ID NO 44
<211> LENGTH: 20
<212> TYPE: DNA
<213> ORGANISM: Artificial
<220> FEATURE:
<223> OTHER INFORMATION: primer

<400> SEQUENCE: 44
tcgatggagc aggtatgaca                                          20

<210> SEQ ID NO 45
<211> LENGTH: 22
<212> TYPE: DNA
<213> ORGANISM: Artificial
<220> FEATURE:
<223> OTHER INFORMATION: primer

<400> SEQUENCE: 45
tttgtgatag gctcgattca ga                                       22

<210> SEQ ID NO 46
<211> LENGTH: 20
<212> TYPE: DNA
<213> ORGANISM: Artificial
<220> FEATURE:
<223> OTHER INFORMATION: primer

<400> SEQUENCE: 46
agtcaaccac ctccacatcc                                          20

<210> SEQ ID NO 47
<211> LENGTH: 20
<212> TYPE: DNA
<213> ORGANISM: Artificial
<220> FEATURE:
<223> OTHER INFORMATION: primer

<400> SEQUENCE: 47
tgattatgaa accgcaacga                                          20

<210> SEQ ID NO 48
<211> LENGTH: 20
<212> TYPE: DNA
<213> ORGANISM: Artificial
<220> FEATURE:
<223> OTHER INFORMATION: primer

<400> SEQUENCE: 48
ccagcctagc attgagaaca                                          20
```

```
<210> SEQ ID NO 49
<211> LENGTH: 20
<212> TYPE: DNA
<213> ORGANISM: Artificial
<220> FEATURE:
<223> OTHER INFORMATION: primer

<400> SEQUENCE: 49
gttgacatgg tatgcccctc                                                   20

<210> SEQ ID NO 50
<211> LENGTH: 21
<212> TYPE: DNA
<213> ORGANISM: Artificial
<220> FEATURE:
<223> OTHER INFORMATION: primer

<400> SEQUENCE: 50
tttgtgagga cttgttgcat t                                                 21

<210> SEQ ID NO 51
<211> LENGTH: 20
<212> TYPE: DNA
<213> ORGANISM: Artificial
<220> FEATURE:
<223> OTHER INFORMATION: primer

<400> SEQUENCE: 51
ctggctcagg tatgctcaca                                                   20

<210> SEQ ID NO 52
<211> LENGTH: 20
<212> TYPE: DNA
<213> ORGANISM: Artificial
<220> FEATURE:
<223> OTHER INFORMATION: primer

<400> SEQUENCE: 52
tgcttgaaat tatcgggagg                                                   20

<210> SEQ ID NO 53
<211> LENGTH: 20
<212> TYPE: DNA
<213> ORGANISM: Artificial
<220> FEATURE:
<223> OTHER INFORMATION: primer

<400> SEQUENCE: 53
gaggataggg ctttgctgtg                                                   20

<210> SEQ ID NO 54
<211> LENGTH: 20
<212> TYPE: DNA
<213> ORGANISM: Artificial
<220> FEATURE:
<223> OTHER INFORMATION: primer

<400> SEQUENCE: 54
gcgcgtaaca gaagcataca                                                   20

<210> SEQ ID NO 55
<211> LENGTH: 20
<212> TYPE: DNA
<213> ORGANISM: Artificial
<220> FEATURE:
<223> OTHER INFORMATION: primer
```

```
<400> SEQUENCE: 55
tgggggctga atatttatgg                                                  20

<210> SEQ ID NO 56
<211> LENGTH: 22
<212> TYPE: DNA
<213> ORGANISM: Artificial
<220> FEATURE:
<223> OTHER INFORMATION: primer

<400> SEQUENCE: 56
tccaattcga aaacatcatc tc                                               22

<210> SEQ ID NO 57
<211> LENGTH: 20
<212> TYPE: DNA
<213> ORGANISM: Artificial
<220> FEATURE:
<223> OTHER INFORMATION: primer

<400> SEQUENCE: 57
gtccttgagc agcagtgtga                                                  20

<210> SEQ ID NO 58
<211> LENGTH: 24
<212> TYPE: DNA
<213> ORGANISM: Artificial
<220> FEATURE:
<223> OTHER INFORMATION: primer

<400> SEQUENCE: 58
tgtttaaaga catacggaag ttga                                             24

<210> SEQ ID NO 59
<211> LENGTH: 224
<212> TYPE: DNA
<213> ORGANISM: Solanum lycopersicum, cv. Micro-Tom, mutant

<400> SEQUENCE: 59
atatatggta tcctaggatt catcgaaatg gtcaagaaaa caggaagttg tttaatggat       60
atgagtttta tactggtgta ccattgcaga gtgatgagtg tttagttttg atgattgaaa      120
aagaatgtga acatatgcct gctgttgatt atcttgaaag attgagaaat ggggatttgg      180
atattggggc tagagatgag attcttgatt ggattgctaa ggtt                       224

<210> SEQ ID NO 60
<211> LENGTH: 80
<212> TYPE: DNA
<213> ORGANISM: Solanum lycopersicum, cv. Micro-Tom, mutant

<400> SEQUENCE: 60
gaggggagag gggtggcgac agaggaggaa acggagggag aaagaaggga agaagaggga       60
aagggagaga agggaggaga                                                  80

<210> SEQ ID NO 61
<211> LENGTH: 84
<212> TYPE: DNA
<213> ORGANISM: Solanum lycopersicum, cv. Micro-Tom, mutant

<400> SEQUENCE: 61
aattttgatt cacaatttta tctagctgta gttctccaac taagatagga ttttccccaa       60
tgaattggtg acattgaaat atgc                                             84
```

-continued

<210> SEQ ID NO 62
<211> LENGTH: 227
<212> TYPE: DNA
<213> ORGANISM: Solanum lycopersicum, cv. Micro-Tom, mutant

<400> SEQUENCE: 62

```
agatatagga gaatatgttc aaaaaaatgc accagagttc tgtcagcctg agattacaag      60
gaatttcctt gaatgcatat gcttttccag aaaattcgat tgagaaaaca atgtaacaag     120
ttttcttccc agtactttag cttactataa tagtaaaatat taagtttctg ttattaagtt    180
ctcttgcata taactcgacg atgtttactt cataaaggaa tcatttc                   227
```

<210> SEQ ID NO 63
<211> LENGTH: 1068
<212> TYPE: DNA
<213> ORGANISM: Solanum lycopersicum, cv. Heinz1706
<220> FEATURE:
<221> NAME/KEY: CDS
<222> LOCATION: (1)..(1068)

<400> SEQUENCE: 63

| | | | | | | | | | | | | | | | | |
|---|---|---|---|---|---|---|---|---|---|---|---|---|---|---|---|---|
| atg | gca | ccc | agt | atg | gat | tgt | gca | gtt | tcc | agc | ctt | ttg | tgt | gct | gaa | 48 |
| Met | Ala | Pro | Ser | Met | Asp | Cys | Ala | Val | Ser | Ser | Leu | Leu | Cys | Ala | Glu | |
| 1 | | | | 5 | | | | | 10 | | | | | 15 | | |

| gac | aac | agt | agc | att | ttt | tgc | aat | gag | gac | gat | gat | gtc | gga | ttt | ggg | 96 |
|---|---|---|---|---|---|---|---|---|---|---|---|---|---|---|---|---|
| Asp | Asn | Ser | Ser | Ile | Phe | Cys | Asn | Glu | Asp | Asp | Asp | Val | Gly | Phe | Gly | |
| | | 20 | | | | | 25 | | | | | 30 | | | | |

| ttt | gta | gag | gaa | gtt | gtg | ggg | gaa | gat | ata | tgg | tat | cct | agg | att | cat | 144 |
|---|---|---|---|---|---|---|---|---|---|---|---|---|---|---|---|---|
| Phe | Val | Glu | Glu | Val | Val | Gly | Glu | Asp | Ile | Trp | Tyr | Pro | Arg | Ile | His | |
| | | | 35 | | | | | 40 | | | | | 45 | | | |

| cga | aat | ggt | caa | gaa | aac | agg | aag | ttg | ttt | aat | gga | gat | gag | ttt | tat | 192 |
|---|---|---|---|---|---|---|---|---|---|---|---|---|---|---|---|---|
| Arg | Asn | Gly | Gln | Glu | Asn | Arg | Lys | Leu | Phe | Asn | Gly | Asp | Glu | Phe | Tyr | |
| 50 | | | | | 55 | | | | | 60 | | | | | | |

| act | ggt | gta | cca | ttg | cag | agt | gat | gag | tgt | tta | gtt | ttg | atg | att | gaa | 240 |
|---|---|---|---|---|---|---|---|---|---|---|---|---|---|---|---|---|
| Thr | Gly | Val | Pro | Leu | Gln | Ser | Asp | Glu | Cys | Leu | Val | Leu | Met | Ile | Glu | |
| 65 | | | | 70 | | | | | 75 | | | | | 80 | | |

| aaa | gaa | tgt | gaa | cat | atg | cct | gct | gtt | gat | tat | ctt | gaa | aga | ttg | aga | 288 |
|---|---|---|---|---|---|---|---|---|---|---|---|---|---|---|---|---|
| Lys | Glu | Cys | Glu | His | Met | Pro | Ala | Val | Asp | Tyr | Leu | Glu | Arg | Leu | Arg | |
| | | | | 85 | | | | | 90 | | | | | 95 | | |

| aat | ggg | gat | ttg | gat | att | ggg | gct | aga | gat | gag | att | ctt | gat | tgg | att | 336 |
|---|---|---|---|---|---|---|---|---|---|---|---|---|---|---|---|---|
| Asn | Gly | Asp | Leu | Asp | Ile | Gly | Ala | Arg | Asp | Glu | Ile | Leu | Asp | Trp | Ile | |
| | | | 100 | | | | | 105 | | | | | 110 | | | |

| gct | aag | gtt | cat | tcg | cag | ttc | aat | ttt | ggt | cca | atg | tgt | gca | tat | ttg | 384 |
|---|---|---|---|---|---|---|---|---|---|---|---|---|---|---|---|---|
| Ala | Lys | Val | His | Ser | Gln | Phe | Asn | Phe | Gly | Pro | Met | Cys | Ala | Tyr | Leu | |
| | | | | 115 | | | | | 120 | | | | | 125 | | |

| gct | gtg | aac | tat | ctt | gat | aga | ttc | ctt | tct | gct | tat | gac | ttg | cct | aag | 432 |
|---|---|---|---|---|---|---|---|---|---|---|---|---|---|---|---|---|
| Ala | Val | Asn | Tyr | Leu | Asp | Arg | Phe | Leu | Ser | Ala | Tyr | Asp | Leu | Pro | Lys | |
| | | 130 | | | | | 135 | | | | | 140 | | | | |

| gaa | aag | gct | tgg | atg | atg | cag | tta | ctc | ggc | gta | gct | tgt | ctg | tcg | att | 480 |
|---|---|---|---|---|---|---|---|---|---|---|---|---|---|---|---|---|
| Glu | Lys | Ala | Trp | Met | Met | Gln | Leu | Leu | Gly | Val | Ala | Cys | Leu | Ser | Ile | |
| 145 | | | | | 150 | | | | | 155 | | | | | 160 | |

| gct | gcc | aaa | atg | gag | gag | act | gat | gtt | cct | ctg | tct | cta | gat | tta | cag | 528 |
|---|---|---|---|---|---|---|---|---|---|---|---|---|---|---|---|---|
| Ala | Ala | Lys | Met | Glu | Glu | Thr | Asp | Val | Pro | Leu | Ser | Leu | Asp | Leu | Gln | |
| | | | | 165 | | | | | 170 | | | | | 175 | | |

| gga | ggg | gat | gca | aag | ttt | gta | ttt | gaa | gct | aaa | aca | ata | cag | aga | atg | 576 |
|---|---|---|---|---|---|---|---|---|---|---|---|---|---|---|---|---|
| Gly | Gly | Asp | Ala | Lys | Phe | Val | Phe | Glu | Ala | Lys | Thr | Ile | Gln | Arg | Met | |
| | | | 180 | | | | | 185 | | | | | 190 | | | |

| gag | cta | ctt | gtg | tta | acc | aca | ttg | aaa | tgg | aga | atg | cag | gct | atc | acc | 624 |
|---|---|---|---|---|---|---|---|---|---|---|---|---|---|---|---|---|
| Glu | Leu | Leu | Val | Leu | Thr | Thr | Leu | Lys | Trp | Arg | Met | Gln | Ala | Ile | Thr | |
| | | | | 195 | | | | | 200 | | | | | 205 | | |

```
cca ttc tct tac ata gat tat ttc atc aag aag ata aat aat agc gat    672
Pro Phe Ser Tyr Ile Asp Tyr Phe Ile Lys Lys Ile Asn Asn Ser Asp
    210             215                 220 caa ata tct tcg atc aat aaa tca gtt gaa ctc ata cta agc aca cta    720
Gln Ile Ser Ser Ile Asn Lys Ser Val Glu Leu Ile Leu Ser Thr Leu
225                 230                 235                 240 aaa ggt att aac ttc ttg gaa ttc aag cct tct gtg att gca gca gca    768
Lys Gly Ile Asn Phe Leu Glu Phe Lys Pro Ser Val Ile Ala Ala Ala
                245                 250                 255 gta gca atc tca ttt gca gta aaa act gag aca tta gac agt gag aaa    816
Val Ala Ile Ser Phe Ala Val Lys Thr Glu Thr Leu Asp Ser Glu Lys
            260                 265                 270 gca cta tct gct cta gtt cag cat gta caa aag gat aaa gtg atg aag    864
Ala Leu Ser Ala Leu Val Gln His Val Gln Lys Asp Lys Val Met Lys
        275                 280                 285 tgt gtt gaa ctg att caa gca ttg tca tta gca agt gac ttt gtt aaa    912
Cys Val Glu Leu Ile Gln Ala Leu Ser Leu Ala Ser Asp Phe Val Lys
    290                 295                 300 gtt cca att gct tct tca atc cca tct gtt cct cag agt cca att ggt    960
Val Pro Ile Ala Ser Ser Ile Pro Ser Val Pro Gln Ser Pro Ile Gly
305                 310                 315                 320 gtg ttg gat gca gca tgt tta agt tac aca agt gat ggc tca gga gtt   1008
Val Leu Asp Ala Ala Cys Leu Ser Tyr Thr Ser Asp Gly Ser Gly Val
                325                 330                 335 gag tcg cgg tct aat tca tcg cat aat agt cca gtg aag agg aga aag   1056
Glu Ser Arg Ser Asn Ser Ser His Asn Ser Pro Val Lys Arg Arg Lys
            340                 345                 350 cta aat act taa                                                   1068
Leu Asn Thr
        355

<210> SEQ ID NO 64
<211> LENGTH: 355
<212> TYPE: PRT
<213> ORGANISM: Solanum lycopersicum, cv. Heinz1706

<400> SEQUENCE: 64

Met Ala Pro Ser Met Asp Cys Ala Val Ser Ser Leu Leu Cys Ala Glu
1               5                   10                  15

Asp Asn Ser Ser Ile Phe Cys Asn Glu Asp Asp Val Gly Phe Gly
                20                  25                  30

Phe Val Glu Glu Val Val Gly Glu Asp Ile Trp Tyr Pro Arg Ile His
            35                  40                  45

Arg Asn Gly Gln Glu Asn Arg Lys Leu Phe Asn Gly Asp Glu Phe Tyr
        50                  55                  60

Thr Gly Val Pro Leu Gln Ser Asp Glu Cys Leu Val Leu Met Ile Glu
65                  70                  75                  80

Lys Glu Cys Glu His Met Pro Ala Val Asp Tyr Leu Glu Arg Leu Arg
                85                  90                  95

Asn Gly Asp Leu Asp Ile Gly Ala Arg Asp Glu Ile Leu Asp Trp Ile
            100                 105                 110

Ala Lys Val His Ser Gln Phe Asn Phe Gly Pro Met Cys Ala Tyr Leu
        115                 120                 125

Ala Val Asn Tyr Leu Asp Arg Phe Leu Ser Ala Tyr Asp Leu Pro Lys
    130                 135                 140
```

-continued

```
Glu Lys Ala Trp Met Met Gln Leu Leu Gly Val Ala Cys Leu Ser Ile
145                 150                 155                 160

Ala Ala Lys Met Glu Glu Thr Asp Val Pro Leu Ser Leu Asp Leu Gln
                165                 170                 175

Gly Gly Asp Ala Lys Phe Val Phe Glu Ala Lys Thr Ile Gln Arg Met
            180                 185                 190

Glu Leu Leu Val Leu Thr Thr Leu Lys Trp Arg Met Gln Ala Ile Thr
        195                 200                 205

Pro Phe Ser Tyr Ile Asp Tyr Phe Ile Lys Lys Ile Asn Asn Ser Asp
    210                 215                 220

Gln Ile Ser Ser Ile Asn Lys Ser Val Glu Leu Ile Leu Ser Thr Leu
225                 230                 235                 240

Lys Gly Ile Asn Phe Leu Glu Phe Lys Pro Ser Val Ile Ala Ala Ala
                245                 250                 255

Val Ala Ile Ser Phe Ala Val Lys Thr Glu Thr Leu Asp Ser Glu Lys
                260                 265                 270

Ala Leu Ser Ala Leu Val Gln His Val Gln Lys Asp Lys Val Met Lys
            275                 280                 285

Cys Val Glu Leu Ile Gln Ala Leu Ser Leu Ala Ser Asp Phe Val Lys
    290                 295                 300

Val Pro Ile Ala Ser Ser Ile Pro Ser Val Pro Gln Ser Pro Ile Gly
305                 310                 315                 320

Val Leu Asp Ala Ala Cys Leu Ser Tyr Thr Ser Asp Gly Ser Gly Val
                325                 330                 335

Glu Ser Arg Ser Asn Ser Ser His Asn Ser Pro Val Lys Arg Arg Lys
                340                 345                 350

Leu Asn Thr
        355

<210> SEQ ID NO 65
<211> LENGTH: 189
<212> TYPE: DNA
<213> ORGANISM: Solanum lycopersicum, cv. Heinz1706
<220> FEATURE:
<221> NAME/KEY: CDS
<222> LOCATION: (1)..(189)

<400> SEQUENCE: 65 atg gag gga gaa aga agg gaa gaa gag gga aag gga gag aag gga gga      48
Met Glu Gly Glu Arg Arg Glu Glu Glu Gly Lys Gly Glu Lys Gly Gly
1               5                   10                  15 gag gaa ggc agg aga aga gga gag aaa gag gaa gaa ggg ggc ggt ggc      96
Glu Glu Gly Arg Arg Arg Gly Glu Lys Glu Glu Glu Gly Gly Gly Gly
            20                  25                  30 acc tgg ttg ttg ccg gtg tac ttg cca ggc cgg aga gct ttt ggt tgc     144
Thr Trp Leu Leu Pro Val Tyr Leu Pro Gly Arg Arg Ala Phe Gly Cys
        35                  40                  45 cgt ctc ttc cgg cta gct tcg ccg gct gga gag aag ggc gaa tag         189
Arg Leu Phe Arg Leu Ala Ser Pro Ala Gly Glu Lys Gly Glu
    50                  55                  60

<210> SEQ ID NO 66
<211> LENGTH: 62
<212> TYPE: PRT
<213> ORGANISM: Solanum lycopersicum, cv. Heinz1706
```

<400> SEQUENCE: 66

```
Met Glu Gly Glu Arg Glu Glu Gly Lys Gly Glu Lys Gly Gly
1               5                   10                  15

Glu Glu Gly Arg Arg Gly Glu Lys Glu Glu Gly Gly Gly
            20                  25                  30

Thr Trp Leu Leu Pro Val Tyr Leu Pro Gly Arg Ala Phe Gly Cys
            35                  40                  45

Arg Leu Phe Arg Leu Ala Ser Pro Ala Gly Glu Lys Gly Glu
        50                  55                  60
```

<210> SEQ ID NO 67
<211> LENGTH: 2049
<212> TYPE: DNA
<213> ORGANISM: Solanum lycopersicum, cv. Heinz1706
<220> FEATURE:
<221> NAME/KEY: CDS
<222> LOCATION: (1)..(2049)

<400> SEQUENCE: 67

```
atg cat ggg tat acc gga aac aac ctc tgg ttt gtt gtt gct gct ggt    48
Met His Gly Tyr Thr Gly Asn Asn Leu Trp Phe Val Val Ala Ala Gly
1               5                   10                  15 gtt gta ggt tgt aaa act gaa tct gag ctc atg ata ttt ggt gag act    96
Val Val Gly Cys Lys Thr Glu Ser Glu Leu Met Ile Phe Gly Glu Thr
            20                  25                  30 ttg gag aat gga gtt aaa gat gag tct caa aaa aat ttt gac gag att   144
Leu Glu Asn Gly Val Lys Asp Glu Ser Gln Lys Asn Phe Asp Glu Ile
        35                  40                  45 acc tcg aca atg aat aat gtt gag agt tct aat ttc tac cac gta atg   192
Thr Ser Thr Met Asn Asn Val Glu Ser Ser Asn Phe Tyr His Val Met
    50                  55                  60 aaa aac agc ttc caa acg gag aag tat gtt aat cgc ttt tca cat tct   240
Lys Asn Ser Phe Gln Thr Glu Lys Tyr Val Asn Arg Phe Ser His Ser
65                  70                  75                  80 cct tta aag ttt cag gtg gac ata tat ggt ttg gac agt aca gaa tac   288
Pro Leu Lys Phe Gln Val Asp Ile Tyr Gly Leu Asp Ser Thr Glu Tyr
                85                  90                  95 aat ttt gat tca caa ttt tat cta gct gta gtt ctc caa cta aga cag   336
Asn Phe Asp Ser Gln Phe Tyr Leu Ala Val Val Leu Gln Leu Arg Gln
            100                 105                 110 gat ttt ccc caa tta att ggt gac att gaa ata tgc aac agt ctc att   384
Asp Phe Pro Gln Leu Ile Gly Asp Ile Glu Ile Cys Asn Ser Leu Ile
        115                 120                 125 tct tca gct gac att gca gct ttt gag aag cta aat ctc aag gtt ttt   432
Ser Ser Ala Asp Ile Ala Ala Phe Glu Lys Leu Asn Leu Lys Val Phe
    130                 135                 140 agc atg aat gac cat agt agg atg aaa gcc caa aga cca acg ata ttc   480
Ser Met Asn Asp His Ser Arg Met Lys Ala Gln Arg Pro Thr Ile Phe
145                 150                 155                 160 tac ata act gat ctt gat tat gat ttt att ggc aat ctt ttg aga gca   528
Tyr Ile Thr Asp Leu Asp Tyr Asp Phe Ile Gly Asn Leu Leu Arg Ala
                165                 170                 175 aac tgg tcc cct gct tgt cta aat gaa agt att tgg atg gca tac tca   576
Asn Trp Ser Pro Ala Cys Leu Asn Glu Ser Ile Trp Met Ala Tyr Ser
            180                 185                 190 tta gaa aaa aca ttc aat tat atg aaa ctt aca aat cgg aat aac ctt   624
Leu Glu Lys Thr Phe Asn Tyr Met Lys Leu Thr Asn Arg Asn Asn Leu
        195                 200                 205
```

-continued

| | | |
|---|---|---|
| gaa aca aag ata cgg tta gag aga att ctt aaa ttc aca aca gag gtt<br>Glu Thr Lys Ile Arg Leu Glu Arg Ile Leu Lys Phe Thr Thr Glu Val<br>210                      215                      220 | | 672 |
| aga ata aaa act tgg tct gag cag act agt gat tcg ttt aaa gga tat<br>Arg Ile Lys Thr Trp Ser Glu Gln Thr Ser Asp Ser Phe Lys Gly Tyr<br>225                      230                      235                      240 | | 720 |
| tcc tgg cat ttc ttt gag gtg gat acc atc act gac atc gac gtt gag<br>Ser Trp His Phe Phe Glu Val Asp Thr Ile Thr Asp Ile Asp Val Glu<br>                      245                      250                      255 | | 768 |
| aag ctg gaa cat tgt agt gat ctt agg aaa agg tat gag ctt gat act<br>Lys Leu Glu His Cys Ser Asp Leu Arg Lys Arg Tyr Glu Leu Asp Thr<br>                          260                      265                      270 | | 816 |
| cca acc gat gag att aat gag tca gca aat gga aat gta gga gca ctg<br>Pro Thr Asp Glu Ile Asn Glu Ser Ala Asn Gly Asn Val Gly Ala Leu<br>275                      280                      285 | | 864 |
| gtt gac agg atc aaa gag ctg aag cgg tat gtc aag atg tct cag ttt<br>Val Asp Arg Ile Lys Glu Leu Lys Arg Tyr Val Lys Met Ser Gln Phe<br>290                      295                      300 | | 912 |
| tac att aga atg cta tat gat ctc aat gag aat aag atc atg aag gaa<br>Tyr Ile Arg Met Leu Tyr Asp Leu Asn Glu Asn Lys Ile Met Lys Glu<br>305                      310                      315                      320 | | 960 |
| cga ttc gaa aaa gtt tta ggc tca gat acg caa gtt cca gtg gta ata<br>Arg Phe Glu Lys Val Leu Gly Ser Asp Thr Gln Val Pro Val Val Ile<br>                          325                      330                      335 | | 1008 |
| tac tgc ctg gga agt gtt gaa tat gat ttg agt cca aag att caa ctg<br>Tyr Cys Leu Gly Ser Val Glu Tyr Asp Leu Ser Pro Lys Ile Gln Leu<br>                      340                      345                      350 | | 1056 |
| gct cta att ctg cat ctg aaa gaa aac gtt gag tgg att ggc aat ctg<br>Ala Leu Ile Leu His Leu Lys Glu Asn Val Glu Trp Ile Gly Asn Leu<br>                        355                      360                      365 | | 1104 |
| gaa ata tat gat cca gtc atg tct gag ctt gat aaa tcg gct tgc tat<br>Glu Ile Tyr Asp Pro Val Met Ser Glu Leu Asp Lys Ser Ala Cys Tyr<br>370                      375                      380 | | 1152 |
| gaa cta ggt ctt acg gtt cta gag tat aac gaa gat tgt aag agg aaa<br>Glu Leu Gly Leu Thr Val Leu Glu Tyr Asn Glu Asp Cys Lys Arg Lys<br>385                      390                      395                      400 | | 1200 |
| gct cag aga cca act atg ttc tac atg ccg tat ccg tcc cat ttt ctt<br>Ala Gln Arg Pro Thr Met Phe Tyr Met Pro Tyr Pro Ser His Phe Leu<br>                          405                      410                      415 | | 1248 |
| att gga aat tta ttg gga gca aac tgg tct tcg ctt tgt ctt agc cat<br>Ile Gly Asn Leu Leu Gly Ala Asn Trp Ser Ser Leu Cys Leu Ser His<br>                      420                      425                      430 | | 1296 |
| atc ata ctg ttg aca tgc tca ctt cac gaa gaa ttc aaa caa gtg tcc<br>Ile Ile Leu Leu Thr Cys Ser Leu His Glu Glu Phe Lys Gln Val Ser<br>                      435                      440                      445 | | 1344 |
| cac gat ctg ttg aat aat cat gaa gca atg atc cga tta cag aag att<br>His Asp Leu Leu Asn Asn His Glu Ala Met Ile Arg Leu Gln Lys Ile<br>450                      455                      460 | | 1392 |
| tta agt ttc aca aca gaa ttc gac ata aaa att act caa gag gaa ata<br>Leu Ser Phe Thr Thr Glu Phe Asp Ile Lys Ile Thr Gln Glu Glu Ile<br>465                      470                      475                      480 | | 1440 |
| gat gag caa ttt cca caa gtt gcg tgg cat ttc ttt ggc gtg gat gca<br>Asp Glu Gln Phe Pro Gln Val Ala Trp His Phe Phe Gly Val Asp Ala<br>                      485                      490                      495 | | 1488 |
| aac ttt gat aca gaa att ggc cag ccg ggg tat tat tcc ttc gat atg<br>Asn Phe Asp Thr Glu Ile Gly Gln Pro Gly Tyr Tyr Ser Phe Asp Met<br>                      500                      505                      510 | | 1536 |
| caa agg tat gtt gaa acg aga ttg ttg agc tgc ggt atg gag aat gat<br>Gln Arg Tyr Val Glu Thr Arg Leu Leu Ser Cys Gly Met Glu Asn Asp<br>                      515                      520                      525 | | 1584 |

```
aag atc agt gat tgg gtt aaa gaa gtt gtg ggt cat tac cgc atg ccc    1632
Lys Ile Ser Asp Trp Val Lys Glu Val Val Gly His Tyr Arg Met Pro
        530                 535                 540 cat cac gtt agg tgt cat tct gtc gct cta tct tct ggt tgg att aaa    1680
His His Val Arg Cys His Ser Val Ala Leu Ser Ser Gly Trp Ile Lys
545                 550                 555                 560 ctt aac ata cac ggc act agc aga aag gag aag cag cca ggt aag ttt    1728
Leu Asn Ile His Gly Thr Ser Arg Lys Glu Lys Gln Pro Gly Lys Phe
                565                 570                 575 agc ggt gtc ttc cga gat gca gaa ggt ctt tgt tta ggc agt tac tca    1776
Ser Gly Val Phe Arg Asp Ala Glu Gly Leu Cys Leu Gly Ser Tyr Ser
            580                 585                 590 ggt gtt tct gat gtc caa gaa gat gac gtg ctt gtt gaa ctt gag gcg    1824
Gly Val Ser Asp Val Gln Glu Asp Asp Val Leu Val Glu Leu Glu Ala
        595                 600                 605 ttg tta cgt ggg ctg gga aaa tgc ata gaa gga gag ccg aaa gca aaa    1872
Leu Leu Arg Gly Leu Gly Lys Cys Ile Glu Gly Glu Pro Lys Ala Lys
    610                 615                 620 aga ttg att gtg gag tcg gac aaa acc atg ctt gtc cta tgt gtc aat    1920
Arg Leu Ile Val Glu Ser Asp Lys Thr Met Leu Val Leu Cys Val Asn
625                 630                 635                 640 ggt cgc ctt gag cca aat agt tca gat atg gag cac atg ttg gac gaa    1968
Gly Arg Leu Glu Pro Asn Ser Ser Asp Met Glu His Met Leu Asp Glu
                645                 650                 655 att ttg gag ttg cag aaa gtg atc aca tgc gta ctc tac cat gtc tcc    2016
Ile Leu Glu Leu Gln Lys Val Ile Thr Cys Val Leu Tyr His Val Ser
            660                 665                 670 gaa gaa gtc agt gaa gct gct gga gtg tgt tga                        2049
Glu Glu Val Ser Glu Ala Ala Gly Val Cys
        675                 680

<210> SEQ ID NO 68
<211> LENGTH: 682
<212> TYPE: PRT
<213> ORGANISM: Solanum lycopersicum, cv. Heinz1706

<400> SEQUENCE: 68

Met His Gly Tyr Thr Gly Asn Asn Leu Trp Phe Val Val Ala Ala Gly
1               5                   10                  15

Val Val Gly Cys Lys Thr Glu Ser Glu Leu Met Ile Phe Gly Glu Thr
            20                  25                  30

Leu Glu Asn Gly Val Lys Asp Glu Ser Gln Lys Asn Phe Asp Glu Ile
        35                  40                  45

Thr Ser Thr Met Asn Asn Val Glu Ser Ser Asn Phe Tyr His Val Met
    50                  55                  60

Lys Asn Ser Phe Gln Thr Glu Lys Tyr Val Asn Arg Phe Ser His Ser
65                  70                  75                  80

Pro Leu Lys Phe Gln Val Asp Ile Tyr Gly Leu Asp Ser Thr Glu Tyr
                85                  90                  95

Asn Phe Asp Ser Gln Phe Tyr Leu Ala Val Val Leu Gln Leu Arg Gln
            100                 105                 110

Asp Phe Pro Gln Leu Ile Gly Asp Ile Glu Ile Cys Asn Ser Leu Ile
        115                 120                 125

Ser Ser Ala Asp Ile Ala Ala Phe Glu Lys Leu Asn Leu Lys Val Phe
    130                 135                 140

Ser Met Asn Asp His Ser Arg Met Lys Ala Gln Arg Pro Thr Ile Phe
145                 150                 155                 160
```

```
Tyr Ile Thr Asp Leu Asp Tyr Asp Phe Ile Gly Asn Leu Leu Arg Ala
            165                 170                 175

Asn Trp Ser Pro Ala Cys Leu Asn Glu Ser Ile Trp Met Ala Tyr Ser
        180                 185                 190

Leu Glu Lys Thr Phe Asn Tyr Met Lys Leu Thr Asn Arg Asn Asn Leu
    195                 200                 205

Glu Thr Lys Ile Arg Leu Glu Arg Ile Leu Lys Phe Thr Thr Glu Val
210                 215                 220

Arg Ile Lys Thr Trp Ser Glu Gln Thr Ser Asp Ser Phe Lys Gly Tyr
225                 230                 235                 240

Ser Trp His Phe Phe Glu Val Asp Thr Ile Thr Asp Ile Asp Val Glu
                245                 250                 255

Lys Leu Glu His Cys Ser Asp Leu Arg Lys Arg Tyr Glu Leu Asp Thr
            260                 265                 270

Pro Thr Asp Glu Ile Asn Glu Ser Ala Asn Gly Asn Val Gly Ala Leu
        275                 280                 285

Val Asp Arg Ile Lys Glu Leu Lys Arg Tyr Val Lys Met Ser Gln Phe
    290                 295                 300

Tyr Ile Arg Met Leu Tyr Asp Leu Asn Glu Asn Lys Ile Met Lys Glu
305                 310                 315                 320

Arg Phe Glu Lys Val Leu Gly Ser Asp Thr Gln Val Pro Val Val Ile
                325                 330                 335

Tyr Cys Leu Gly Ser Val Glu Tyr Asp Leu Ser Pro Lys Ile Gln Leu
            340                 345                 350

Ala Leu Ile Leu His Leu Lys Glu Asn Val Glu Trp Ile Gly Asn Leu
        355                 360                 365

Glu Ile Tyr Asp Pro Val Met Ser Glu Leu Asp Lys Ser Ala Cys Tyr
    370                 375                 380

Glu Leu Gly Leu Thr Val Leu Glu Tyr Asn Glu Asp Cys Lys Arg Lys
385                 390                 395                 400

Ala Gln Arg Pro Thr Met Phe Tyr Met Pro Tyr Pro Ser His Phe Leu
                405                 410                 415

Ile Gly Asn Leu Leu Gly Ala Asn Trp Ser Ser Leu Cys Leu Ser His
            420                 425                 430

Ile Ile Leu Leu Thr Cys Ser Leu His Glu Glu Phe Lys Gln Val Ser
        435                 440                 445

His Asp Leu Leu Asn Asn His Glu Ala Met Ile Arg Leu Gln Lys Ile
    450                 455                 460

Leu Ser Phe Thr Thr Glu Phe Asp Ile Lys Ile Thr Gln Glu Ile
465                 470                 475                 480

Asp Glu Gln Phe Pro Gln Val Ala Trp His Phe Gly Val Asp Ala
                485                 490                 495

Asn Phe Asp Thr Glu Ile Gly Gln Pro Gly Tyr Tyr Ser Phe Asp Met
            500                 505                 510

Gln Arg Tyr Val Glu Thr Arg Leu Leu Ser Cys Gly Met Glu Asn Asp
        515                 520                 525

Lys Ile Ser Asp Trp Val Lys Glu Val Val Gly His Tyr Arg Met Pro
    530                 535                 540

His His Val Arg Cys His Ser Val Ala Leu Ser Ser Gly Trp Ile Lys
545                 550                 555                 560

Leu Asn Ile His Gly Thr Ser Arg Lys Glu Lys Gln Pro Gly Lys Phe
                565                 570                 575
```

```
Ser Gly Val Phe Arg Asp Ala Glu Gly Leu Cys Leu Gly Ser Tyr Ser
            580                 585                 590

Gly Val Ser Asp Val Gln Glu Asp Val Leu Val Glu Leu Glu Ala
        595                 600                 605

Leu Leu Arg Gly Leu Gly Lys Cys Ile Glu Gly Glu Pro Lys Ala Lys
    610                 615                 620

Arg Leu Ile Val Glu Ser Asp Lys Thr Met Leu Val Leu Cys Val Asn
625                 630                 635                 640

Gly Arg Leu Glu Pro Asn Ser Ser Asp Met Glu His Met Leu Asp Glu
                645                 650                 655

Ile Leu Glu Leu Gln Lys Val Ile Thr Cys Val Leu Tyr His Val Ser
            660                 665                 670

Glu Glu Val Ser Glu Ala Ala Gly Val Cys
        675                 680

<210> SEQ ID NO 69
<211> LENGTH: 306
<212> TYPE: DNA
<213> ORGANISM: Solanum lycopersicum, cv. Heinz1706
<220> FEATURE:
<221> NAME/KEY: CDS
<222> LOCATION: (1)..(306)

<400> SEQUENCE: 69 atg ata gtt ggg aac tta tca aga agc caa ttg agc aaa gag caa gtg      48
Met Ile Val Gly Asn Leu Ser Arg Ser Gln Leu Ser Lys Glu Gln Val
1               5                   10                  15 caa gtc tac atc aat gaa gag aat aat agg agg aag agt ctc ttg gtg      96
Gln Val Tyr Ile Asn Glu Glu Asn Asn Arg Arg Lys Ser Leu Leu Val
            20                  25                  30 aaa tac att cgc cta tgc aac gat gcc aaa gta cca gtt gat act atg     144
Lys Tyr Ile Arg Leu Cys Asn Asp Ala Lys Val Pro Val Asp Thr Met
        35                  40                  45 ctt gtg gaa agc aat tca cca gct aaa gca tta ctt gac ctt ata cct     192
Leu Val Glu Ser Asn Ser Pro Ala Lys Ala Leu Leu Asp Leu Ile Pro
    50                  55                  60 gtt gtc aac att aca agc ctt att att gga aac agg cca ccg cgt tcc     240
Val Val Asn Ile Thr Ser Leu Ile Ile Gly Asn Arg Pro Pro Arg Ser
65                  70                  75                  80 acg agg cta gta aag aat gga caa gat ata gga gaa tat gtt caa aaa     288
Thr Arg Leu Val Lys Asn Gly Gln Asp Ile Gly Glu Tyr Val Gln Lys
                85                  90                  95 aat gca cca gag ttc tga                                             306
Asn Ala Pro Glu Phe
            100

<210> SEQ ID NO 70
<211> LENGTH: 101
<212> TYPE: PRT
<213> ORGANISM: Solanum lycopersicum, cv. Heinz1706

<400> SEQUENCE: 70

Met Ile Val Gly Asn Leu Ser Arg Ser Gln Leu Ser Lys Glu Gln Val
1               5                   10                  15

Gln Val Tyr Ile Asn Glu Glu Asn Asn Arg Arg Lys Ser Leu Leu Val
            20                  25                  30

Lys Tyr Ile Arg Leu Cys Asn Asp Ala Lys Val Pro Val Asp Thr Met
        35                  40                  45
```

```
Leu Val Glu Ser Asn Ser Pro Ala Lys Ala Leu Leu Asp Leu Ile Pro
 50                  55                  60

Val Val Asn Ile Thr Ser Leu Ile Ile Gly Asn Arg Pro Pro Arg Ser
 65                  70                  75                  80

Thr Arg Leu Val Lys Asn Gly Gln Asp Ile Gly Glu Tyr Val Gln Lys
                 85                  90                  95

Asn Ala Pro Glu Phe
            100

<210> SEQ ID NO 71
<211> LENGTH: 176
<212> TYPE: DNA
<213> ORGANISM: Solanum lycopersicum, cv. Micro-Tom, mutant
<220> FEATURE:
<221> NAME/KEY: CDS
<222> LOCATION: (1)..(102)

<400> SEQUENCE: 71 acg gag gga gaa aga agg gaa gaa gag gga aag gga gag aag gga gga       48
Thr Glu Gly Glu Arg Arg Glu Glu Glu Gly Lys Gly Glu Lys Gly Gly
 1               5                  10                  15 gaa gag gag aga aag agg aag aag agg gcg gtg gct cca ggt tgt tgc       96
Glu Glu Glu Arg Lys Arg Lys Lys Arg Ala Val Ala Pro Gly Cys Cys
                20                  25                  30 cgg tga actcgccagg acggagagct tttggttgcc gtctcttccg gctagcttcg       152
Arg ccggctggag agaagggcga atag                                            176

<210> SEQ ID NO 72
<211> LENGTH: 33
<212> TYPE: PRT
<213> ORGANISM: Solanum lycopersicum, cv. Micro-Tom, mutant

<400> SEQUENCE: 72

Thr Glu Gly Glu Arg Arg Glu Glu Glu Gly Lys Gly Glu Lys Gly Gly
 1               5                  10                  15

Glu Glu Glu Arg Lys Arg Lys Lys Arg Ala Val Ala Pro Gly Cys Cys
                20                  25                  30

Arg

<210> SEQ ID NO 73
<211> LENGTH: 189
<212> TYPE: DNA
<213> ORGANISM: Solanum lycopersicum, cv. Micro-Tom, wild-type
<220> FEATURE:
<221> NAME/KEY: CDS
<222> LOCATION: (1)..(189)

<400> SEQUENCE: 73 atg gag gga gaa aga agg gaa gaa gag gga aag gga gag aag gga gga       48
Met Glu Gly Glu Arg Arg Glu Glu Glu Gly Lys Gly Glu Lys Gly Gly
 1               5                  10                  15 gag gaa ggc agg aga aga gga gag aaa gag gaa gaa ggg ggc ggt ggc       96
Glu Glu Gly Arg Arg Arg Gly Glu Lys Glu Glu Glu Gly Gly Gly Gly
                20                  25                  30 acc tgg ttg ttg ccg gtg tac ttg cca ggc cgg aga gct ttt ggt tgc      144
Thr Trp Leu Leu Pro Val Tyr Leu Pro Gly Arg Arg Ala Phe Gly Cys
                35                  40                  45 cgt ctc ttc cgg cta gct tcg ccg gct gga gag aag ggc gaa tag          189
Arg Leu Phe Arg Leu Ala Ser Pro Ala Gly Glu Lys Gly Glu
                50                  55                  60
```

-continued

<210> SEQ ID NO 74
<211> LENGTH: 62
<212> TYPE: PRT
<213> ORGANISM: Solanum lycopersicum, cv. Micro-Tom, wild-type

<400> SEQUENCE: 74

```
Met Glu Gly Glu Arg Arg Glu Glu Gly Lys Gly Glu Lys Gly Gly
1               5                   10                  15

Glu Glu Gly Arg Arg Arg Gly Glu Lys Glu Glu Glu Gly Gly Gly
            20                  25                  30

Thr Trp Leu Leu Pro Val Tyr Leu Pro Gly Arg Arg Ala Phe Gly Cys
        35                  40                  45

Arg Leu Phe Arg Leu Ala Ser Pro Ala Gly Glu Lys Gly Glu
    50                  55                  60
```

<210> SEQ ID NO 75
<211> LENGTH: 2060
<212> TYPE: DNA
<213> ORGANISM: Solanum lycopersicum, cv. Micro-Tom, mutant
<220> FEATURE:
<221> NAME/KEY: CDS
<222> LOCATION: (1)..(165)

<400> SEQUENCE: 75

```
atg cat ggg tat acc gga aac aac ctc tgg ttt gtt gtt gct gct ggt    48
Met His Gly Tyr Thr Gly Asn Asn Leu Trp Phe Val Val Ala Ala Gly
1               5                   10                  15 gtt gta ggt tgt aaa act gaa tct gag ctc atg ata ttt ggt gag act    96
Val Val Gly Cys Lys Thr Glu Ser Glu Leu Met Ile Phe Gly Glu Thr
            20                  25                  30 ttg gag aat gga gtt aaa gat gag tct caa aaa aat ttt gac gag att    144
Leu Glu Asn Gly Val Lys Asp Glu Ser Gln Lys Asn Phe Asp Glu Ile
        35                  40                  45 acc ttt ttg acg aga tta cct tgagttctaa tttctactac gtaatgaaag        195
Thr Phe Leu Thr Arg Leu Pro
        50                  55 acagcttcca aacataattg atcatcaagg agtatcttaa tcgcttttca cactctcctt    255
taaagtttca ggtggacata tatggttttgg atggtacaga atataatttt gattcacaat    315
tttatctagc tgtagttctc caactaagat agaattttcc ccaatgaatt ggtgacattg    375
aaatatgcga cagtctcatt tcttcagctg acattgcagc ttccgagaag ctaaatctca    435 aggttttttag catggatgac cacagtagga tgaaagccca agaccaacg atattctaca    495 taactgatct tgattatgat tttattggca atcttttgag agcaaactgg tcccctgctt    555
gtctaaatga agtatttgg atggcatact cattagaaaa acattcaat tatatgaaac    615 ttacaaatcg gaataaccctt gaaacaaaga tacggttaga gagaattctt aaattcacaa    675
cagaggttag aataaaaact tggtctgagc agactagtga ttcgtttaaa ggatattcct    735
ggcatttctt tgaggtggat accatcactg acatcgacgt tgagaagctg aacattgta    795 gtgatcttag gaaaaggtat gagcttgata ctccaaccga tgagattaat gagtcagcaa    855
atggaaatgt aggagcactg gttgacagga tcaaagagct gaagcggtat gtcaagatgt    915
ctcagtttta cattgaaatg ctatatgatc tcaatgagaa taagatcatg aaggaacgat    975
tcgaaaaagt tttaggctca gatacgcaag ttccagtggt aatatactgc ctgggaagtg    1035
ttgaatatga tttgagtcca aagattcaac tggctctaat tctgcatctg aaagaaaacg    1095
ttgagtggat tggcaatctg gaaatatatg atccagtcat gtctgagctt gataaatcgg    1155
cttgctatga actaggtctt acggttctag agtataacga agattgtaag aggaaagctc    1215
```

```
agagaccaac tatgttctac atgccgtatc cgtcccattt tcttattgga aatttattgg   1275
gagcaaactg gtcttcgctt tgtcttagcc atatcatact gttgacatgc tcacttcacg   1335
aagaattcaa acaagtgtcc cacgatctgt tgaataatca tgaagcaatg atccgattac   1395
agaagatttt aagtttcaca acagaattcg acataaaaat tactcaagag gaaatagatg   1455
agcaatttcc acaagttgcg tggcatttct ttggcgtgga tgcaaacttt gatacagaaa   1515
ttggccagcc ggggtattat tccttcgata tgcaaaggta tgttgaaacg agattgttga   1575
gctgcggtat ggagaatgat aagatcagtg attgggttaa agaagttgtg ggtcattacc   1635
gcatgcccca tcacgttagg tgtcattctg tcgctctatc ttctggttgg attaaactta   1695
acatacacgg cactagcaga aaggagaagc agccaggtaa gtttagcggt gtcttccgag   1755
atgcagaagg tctttgttta ggcagttact caggtgtttc tgatgtccaa gaagatgacg   1815
tgcttgttga acttgaggcg ttgttacgtg ggctgggaaa atgcatagaa ggagagccga   1875
aagcaaaaag attgattgtg gagtcggaca aaaccatgct tgtcctatgt gtcaatggtc   1935
gccttgagcc aaatagttca gatatggagc acatgttgga cgaaattttg gagttgcaga   1995
aagtgatcac atgcgtactc taccatgtct ccgaagaagt cagtgaagct gctggagtgt   2055
gttga                                                              2060
```

<210> SEQ ID NO 76
<211> LENGTH: 55
<212> TYPE: PRT
<213> ORGANISM: Solanum lycopersicum, cv. Micro-Tom, mutant

<400> SEQUENCE: 76

```
Met His Gly Tyr Thr Gly Asn Asn Leu Trp Phe Val Val Ala Ala Gly
1               5                   10                  15

Val Val Gly Cys Lys Thr Glu Ser Glu Leu Met Ile Phe Gly Glu Thr
            20                  25                  30

Leu Glu Asn Gly Val Lys Asp Glu Ser Gln Lys Asn Phe Asp Glu Ile
        35                  40                  45

Thr Phe Leu Thr Arg Leu Pro
    50                  55
```

<210> SEQ ID NO 77
<211> LENGTH: 2049
<212> TYPE: DNA
<213> ORGANISM: Solanum lycopersicum, cv. Micro-Tom, wild-type
<220> FEATURE:
<221> NAME/KEY: CDS
<222> LOCATION: (1)..(2049)

<400> SEQUENCE: 77

```
atg cat ggg tat acc gga aac aac ctc tgg ttt gtt gtt gct gct ggt    48
Met His Gly Tyr Thr Gly Asn Asn Leu Trp Phe Val Val Ala Ala Gly
1               5                   10                  15 gtt gta ggt tgt aaa act gaa tct gag ctc atg ata ttt ggt gag act    96
Val Val Gly Cys Lys Thr Glu Ser Glu Leu Met Ile Phe Gly Glu Thr
            20                  25                  30 ttg gag aat gga gtt aaa gat gag tct caa aaa aat ttt gac gag att   144
Leu Glu Asn Gly Val Lys Asp Glu Ser Gln Lys Asn Phe Asp Glu Ile
        35                  40                  45 acc tcg aca atg aat aat gtt gag agt tct aat ttc tac cac gta atg   192
Thr Ser Thr Met Asn Asn Val Glu Ser Ser Asn Phe Tyr His Val Met
    50                  55                  60
```

-continued

| | | |
|---|---|---|
| aaa aac agc ttc caa acg gag aag tat gtt aat cgc ttt tca cat tct<br>Lys Asn Ser Phe Gln Thr Glu Lys Tyr Val Asn Arg Phe Ser His Ser<br>65                           70                        75                    80 | | 240 |
| cct tta aag ttt cag gtg gac ata tat ggt ttg gac agt aca gaa tac<br>Pro Leu Lys Phe Gln Val Asp Ile Tyr Gly Leu Asp Ser Thr Glu Tyr<br>                       85                       90                    95 | | 288 |
| aat ttt gat tca caa ttt tat cta gct gta gtt ctc caa cta aga cag<br>Asn Phe Asp Ser Gln Phe Tyr Leu Ala Val Val Leu Gln Leu Arg Gln<br>                  100                  105                  110 | | 336 |
| gat ttt ccc caa tta att ggt gac att gaa ata tgc aac agt ctc att<br>Asp Phe Pro Gln Leu Ile Gly Asp Ile Glu Ile Cys Asn Ser Leu Ile<br>        115                  120                  125 | | 384 |
| tct tca gct gac att gca gct ttt gag aag cta aat ctc aag gtt ttt<br>Ser Ser Ala Asp Ile Ala Ala Phe Glu Lys Leu Asn Leu Lys Val Phe<br>130                         135                  140 | | 432 |
| agc atg aat gac cat agt agg atg aaa gcc caa aga cca acg ata ttc<br>Ser Met Asn Asp His Ser Arg Met Lys Ala Gln Arg Pro Thr Ile Phe<br>145                       150                  155                  160 | | 480 |
| tac ata act gat ctt gat tat gat ttt att ggc aat ctt ttg aga gca<br>Tyr Ile Thr Asp Leu Asp Tyr Asp Phe Ile Gly Asn Leu Leu Arg Ala<br>                  165                  170                  175 | | 528 |
| aac tgg tcc cct gct tgt cta aat gaa agt att tgg atg gca tac tca<br>Asn Trp Ser Pro Ala Cys Leu Asn Glu Ser Ile Trp Met Ala Tyr Ser<br>        180                  185                  190 | | 576 |
| tta gaa aaa aca ttc aat tat atg aaa ctt aca aat cgg aat aac ctt<br>Leu Glu Lys Thr Phe Asn Tyr Met Lys Leu Thr Asn Arg Asn Asn Leu<br>195                       200                  205 | | 624 |
| gaa aca aag ata cgg tta gag aga att ctt aaa ttc aca aca gag gtt<br>Glu Thr Lys Ile Arg Leu Glu Arg Ile Leu Lys Phe Thr Thr Glu Val<br>210                       215                  220 | | 672 |
| aga ata aaa act tgg tct gag cag act agt gat tcg ttt aaa gga tat<br>Arg Ile Lys Thr Trp Ser Glu Gln Thr Ser Asp Ser Phe Lys Gly Tyr<br>225                       230                  235                  240 | | 720 |
| tcc tgg cat ttc ttt gag gtg gat acc atc act gac atc gac gtt gag<br>Ser Trp His Phe Phe Glu Val Asp Thr Ile Thr Asp Ile Asp Val Glu<br>                  245                  250                  255 | | 768 |
| aag ctg gaa cat tgt agt gat ctt agg aaa agg tat gag ctt gat act<br>Lys Leu Glu His Cys Ser Asp Leu Arg Lys Arg Tyr Glu Leu Asp Thr<br>        260                  265                  270 | | 816 |
| cca acc gat gag att aat gag tca gca aat gga aat gta gga gca ctg<br>Pro Thr Asp Glu Ile Asn Glu Ser Ala Asn Gly Asn Val Gly Ala Leu<br>275                       280                  285 | | 864 |
| gtt gac agg atc aaa gag ctg aag cgg tat gtc aag atg tct cag ttt<br>Val Asp Arg Ile Lys Glu Leu Lys Arg Tyr Val Lys Met Ser Gln Phe<br>290                       295                  300 | | 912 |
| tac att aga atg cta tat gat ctc aat gag aat aag atc atg aag gaa<br>Tyr Ile Arg Met Leu Tyr Asp Leu Asn Glu Asn Lys Ile Met Lys Glu<br>305                       310                  315                  320 | | 960 |
| cga ttc gaa aaa gtt tta ggc tca gat acg caa gtt cca gtg gta ata<br>Arg Phe Glu Lys Val Leu Gly Ser Asp Thr Gln Val Pro Val Val Ile<br>                  325                  330                  335 | | 1008 |
| tac tgc ctg gga agt gtt gaa tat gat ttg agt cca aag att caa ctg<br>Tyr Cys Leu Gly Ser Val Glu Tyr Asp Leu Ser Pro Lys Ile Gln Leu<br>        340                  345                  350 | | 1056 |
| gct cta att ctg cat ctg aaa gaa aac gtt gag tgg att ggc aat ctg<br>Ala Leu Ile Leu His Leu Lys Glu Asn Val Glu Trp Ile Gly Asn Leu<br>355                       360                  365 | | 1104 |
| gaa ata tat gat cca gtc atg tct gag ctt gat aaa tcg gct tgc tat<br>Glu Ile Tyr Asp Pro Val Met Ser Glu Leu Asp Lys Ser Ala Cys Tyr<br>370                       375                  380 | | 1152 |

```
                                            -continued gaa cta ggt ctt acg gtt cta gag tat aac gaa gat tgt aag agg aaa   1200
Glu Leu Gly Leu Thr Val Leu Glu Tyr Asn Glu Asp Cys Lys Arg Lys
385                 390                 395                 400 gct cag aga cca act atg ttc tac atg ccg tat ccg tcc cat ttt ctt   1248
Ala Gln Arg Pro Thr Met Phe Tyr Met Pro Tyr Pro Ser His Phe Leu
                405                 410                 415 att gga aat tta ttg gga gca aac tgg tct tcg ctt tgt ctt agc cat   1296
Ile Gly Asn Leu Leu Gly Ala Asn Trp Ser Ser Leu Cys Leu Ser His
                420                 425                 430 atc ata ctg ttg aca tgc tca ctt cac gaa gaa ttc aaa caa gtg tcc   1344
Ile Ile Leu Leu Thr Cys Ser Leu His Glu Glu Phe Lys Gln Val Ser
                435                 440                 445 cac gat ctg ttg aat aat cat gaa gca atg atc cga tta cag aag att   1392
His Asp Leu Leu Asn Asn His Glu Ala Met Ile Arg Leu Gln Lys Ile
        450                 455                 460 tta agt ttc aca aca gaa ttc gac ata aaa att act caa gag gaa ata   1440
Leu Ser Phe Thr Thr Glu Phe Asp Ile Lys Ile Thr Gln Glu Glu Ile
465                 470                 475                 480 gat gag caa ttt cca caa gtt gcg tgg cat ttc ttt ggc gtg gat gca   1488
Asp Glu Gln Phe Pro Gln Val Ala Trp His Phe Phe Gly Val Asp Ala
                485                 490                 495 aac ttt gat aca gaa att ggc cag ccg ggg tat tat tcc ttc gat atg   1536
Asn Phe Asp Thr Glu Ile Gly Gln Pro Gly Tyr Tyr Ser Phe Asp Met
                500                 505                 510 caa agg tat gtt gaa acg aga ttg ttg agc tgc ggt atg gag aat gat   1584
Gln Arg Tyr Val Glu Thr Arg Leu Leu Ser Cys Gly Met Glu Asn Asp
                515                 520                 525 aag atc agt gat tgg gtt aaa gaa gtt gtg ggt cat tac cgc atg ccc   1632
Lys Ile Ser Asp Trp Val Lys Glu Val Val Gly His Tyr Arg Met Pro
        530                 535                 540 cat cac gtt agg tgt cat tct gtc gct cta tct tct ggt tgg att aaa   1680
His His Val Arg Cys His Ser Val Ala Leu Ser Ser Gly Trp Ile Lys
545                 550                 555                 560 ctt aac ata cac ggc act agc aga aag gag aag cag cca ggt aag ttt   1728
Leu Asn Ile His Gly Thr Ser Arg Lys Glu Lys Gln Pro Gly Lys Phe
                565                 570                 575 agc ggt gtc ttc cga gat gca gaa ggt ctt tgt tta ggc agt tac tca   1776
Ser Gly Val Phe Arg Asp Ala Glu Gly Leu Cys Leu Gly Ser Tyr Ser
                580                 585                 590 ggt gtt tct gat gtc caa gaa gat gac gtg ctt gtt gaa ctt gag gcg   1824
Gly Val Ser Asp Val Gln Glu Asp Asp Val Leu Val Glu Leu Glu Ala
                595                 600                 605 ttg tta cgt ggg ctg gga aaa tgc ata gaa gga gag ccg aaa gca aaa   1872
Leu Leu Arg Gly Leu Gly Lys Cys Ile Glu Gly Glu Pro Lys Ala Lys
        610                 615                 620 aga ttg att gtg gag tcg gac aaa acc atg ctt gtc cta tgt gtc aat   1920
Arg Leu Ile Val Glu Ser Asp Lys Thr Met Leu Val Leu Cys Val Asn
625                 630                 635                 640 ggt cgc ctt gag cca aat agt tca gat atg gag cac atg ttg gac gaa   1968
Gly Arg Leu Glu Pro Asn Ser Ser Asp Met Glu His Met Leu Asp Glu
                645                 650                 655 att ttg gag ttg cag aaa gtg atc aca tgc gta ctc tac cat gtc tcc   2016
Ile Leu Glu Leu Gln Lys Val Ile Thr Cys Val Leu Tyr His Val Ser
                660                 665                 670 gaa gaa gtc agt gaa gct gct gga gtg tgt tga                       2049
Glu Glu Val Ser Glu Ala Ala Gly Val Cys
                675                 680
```

<210> SEQ ID NO 78
<211> LENGTH: 682
<212> TYPE: PRT
<213> ORGANISM: Solanum lycopersicum, cv. Micro-Tom, wild-type

<400> SEQUENCE: 78

```
Met His Gly Tyr Thr Gly Asn Asn Leu Trp Phe Val Val Ala Ala Gly
1               5                   10                  15

Val Val Gly Cys Lys Thr Glu Ser Glu Leu Met Ile Phe Gly Glu Thr
            20                  25                  30

Leu Glu Asn Gly Val Lys Asp Glu Ser Gln Lys Asn Phe Asp Glu Ile
        35                  40                  45

Thr Ser Thr Met Asn Asn Val Glu Ser Ser Asn Phe Tyr His Val Met
50                  55                  60

Lys Asn Ser Phe Gln Thr Glu Lys Tyr Val Asn Arg Phe Ser His Ser
65                  70                  75                  80

Pro Leu Lys Phe Gln Val Asp Ile Tyr Gly Leu Asp Ser Thr Glu Tyr
                85                  90                  95

Asn Phe Asp Ser Gln Phe Tyr Leu Ala Val Val Leu Gln Leu Arg Gln
            100                 105                 110

Asp Phe Pro Gln Leu Ile Gly Asp Ile Glu Ile Cys Asn Ser Leu Ile
        115                 120                 125

Ser Ser Ala Asp Ile Ala Ala Phe Glu Lys Leu Asn Leu Lys Val Phe
130                 135                 140

Ser Met Asn Asp His Ser Arg Met Lys Ala Gln Arg Pro Thr Ile Phe
145                 150                 155                 160

Tyr Ile Thr Asp Leu Asp Tyr Asp Phe Ile Gly Asn Leu Leu Arg Ala
                165                 170                 175

Asn Trp Ser Pro Ala Cys Leu Asn Glu Ser Ile Trp Met Ala Tyr Ser
            180                 185                 190

Leu Glu Lys Thr Phe Asn Tyr Met Lys Leu Thr Asn Arg Asn Asn Leu
        195                 200                 205

Glu Thr Lys Ile Arg Leu Glu Arg Ile Leu Lys Phe Thr Thr Glu Val
210                 215                 220

Arg Ile Lys Thr Trp Ser Glu Gln Thr Ser Asp Ser Phe Lys Gly Tyr
225                 230                 235                 240

Ser Trp His Phe Phe Glu Val Asp Thr Ile Thr Asp Ile Asp Val Glu
                245                 250                 255

Lys Leu Glu His Cys Ser Asp Leu Arg Lys Arg Tyr Glu Leu Asp Thr
            260                 265                 270

Pro Thr Asp Glu Ile Asn Glu Ser Ala Asn Gly Asn Val Gly Ala Leu
        275                 280                 285

Val Asp Arg Ile Lys Glu Leu Lys Arg Tyr Val Lys Met Ser Gln Phe
290                 295                 300

Tyr Ile Arg Met Leu Tyr Asp Leu Asn Glu Asn Lys Ile Met Lys Glu
305                 310                 315                 320

Arg Phe Glu Lys Val Leu Gly Ser Asp Thr Gln Val Pro Val Val Ile
                325                 330                 335

Tyr Cys Leu Gly Ser Val Glu Tyr Asp Leu Ser Pro Lys Ile Gln Leu
            340                 345                 350

Ala Leu Ile Leu His Leu Lys Glu Asn Val Glu Trp Ile Gly Asn Leu
        355                 360                 365

Glu Ile Tyr Asp Pro Val Met Ser Glu Leu Asp Lys Ser Ala Cys Tyr
370                 375                 380
```

-continued

```
Glu Leu Gly Leu Thr Val Leu Glu Tyr Asn Glu Asp Cys Lys Arg Lys
385                 390                 395                 400

Ala Gln Arg Pro Thr Met Phe Tyr Met Pro Tyr Pro Ser His Phe Leu
            405                 410                 415

Ile Gly Asn Leu Leu Gly Ala Asn Trp Ser Ser Leu Cys Leu Ser His
            420                 425                 430

Ile Ile Leu Leu Thr Cys Ser Leu His Glu Glu Phe Lys Gln Val Ser
            435                 440                 445

His Asp Leu Leu Asn Asn His Glu Ala Met Ile Arg Leu Gln Lys Ile
450                 455                 460

Leu Ser Phe Thr Thr Glu Phe Asp Ile Lys Ile Thr Gln Glu Glu Ile
465                 470                 475                 480

Asp Glu Gln Phe Pro Gln Val Ala Trp His Phe Phe Gly Val Asp Ala
                485                 490                 495

Asn Phe Asp Thr Glu Ile Gly Gln Pro Gly Tyr Tyr Ser Phe Asp Met
            500                 505                 510

Gln Arg Tyr Val Glu Thr Arg Leu Leu Ser Cys Gly Met Glu Asn Asp
            515                 520                 525

Lys Ile Ser Asp Trp Val Lys Glu Val Val Gly His Tyr Arg Met Pro
530                 535                 540

His His Val Arg Cys His Ser Val Ala Leu Ser Ser Gly Trp Ile Lys
545                 550                 555                 560

Leu Asn Ile His Gly Thr Ser Arg Lys Glu Lys Gln Pro Gly Lys Phe
                565                 570                 575

Ser Gly Val Phe Arg Asp Ala Glu Gly Leu Cys Leu Gly Ser Tyr Ser
            580                 585                 590

Gly Val Ser Asp Val Gln Glu Asp Val Leu Val Glu Leu Glu Ala
            595                 600                 605

Leu Leu Arg Gly Leu Gly Lys Cys Ile Glu Gly Glu Pro Lys Ala Lys
610                 615                 620

Arg Leu Ile Val Glu Ser Asp Lys Thr Met Leu Val Leu Cys Val Asn
625                 630                 635                 640

Gly Arg Leu Glu Pro Asn Ser Ser Asp Met Glu His Met Leu Asp Glu
                645                 650                 655

Ile Leu Glu Leu Gln Lys Val Ile Thr Cys Val Leu Tyr His Val Ser
            660                 665                 670

Glu Glu Val Ser Glu Ala Ala Gly Val Cys
            675                 680
```

<210> SEQ ID NO 79
<211> LENGTH: 306
<212> TYPE: DNA
<213> ORGANISM: Solanum lycopersicum, cv. Micro-Tom, mutant
<220> FEATURE:
<221> NAME/KEY: CDS
<222> LOCATION: (1)..(306)

<400> SEQUENCE: 79

```
atg ata gtt ggg aac tta tca aga agc caa ttg agc aaa gag caa gtg      48
Met Ile Val Gly Asn Leu Ser Arg Ser Gln Leu Ser Lys Glu Gln Val
1               5                   10                  15 caa gtc tac atc aat gaa gag aat aat agg agg aag agt ctc ttg gtg      96
Gln Val Tyr Ile Asn Glu Glu Asn Asn Arg Arg Lys Ser Leu Leu Val
                20                  25                  30 aaa tac att cgc cta tgc aac gat gcc aaa gta cca gtt gat act atg     144
Lys Tyr Ile Arg Leu Cys Asn Asp Ala Lys Val Pro Val Asp Thr Met
            35                  40                  45
```

```
ctt gtg gaa agc aat tca cca gct aaa gca tta ctt gac ctt ata cct    192
Leu Val Glu Ser Asn Ser Pro Ala Lys Ala Leu Leu Asp Leu Ile Pro
     50                  55                  60 gtt gtc aac att aca agc ctt att att gga aac agg cca ccg cgt tcc    240
Val Val Asn Ile Thr Ser Leu Ile Ile Gly Asn Arg Pro Pro Arg Ser
 65                  70                  75                  80 acg agg cta gta aag aat gga caa gat ata gga gaa tat gtt caa aaa    288
Thr Arg Leu Val Lys Asn Gly Gln Asp Ile Gly Glu Tyr Val Gln Lys
                 85                  90                  95 aat gca cca gag ttc tgt                                            306
Asn Ala Pro Glu Phe Cys
            100
```

<210> SEQ ID NO 80
<211> LENGTH: 102
<212> TYPE: PRT
<213> ORGANISM: Solanum lycopersicum, cv. Micro-Tom, mutant

<400> SEQUENCE: 80

```
Met Ile Val Gly Asn Leu Ser Arg Ser Gln Leu Ser Lys Glu Gln Val
 1               5                   10                  15

Gln Val Tyr Ile Asn Glu Glu Asn Asn Arg Arg Lys Ser Leu Leu Val
                 20                  25                  30

Lys Tyr Ile Arg Leu Cys Asn Asp Ala Lys Val Pro Val Asp Thr Met
             35                  40                  45

Leu Val Glu Ser Asn Ser Pro Ala Lys Ala Leu Leu Asp Leu Ile Pro
         50                  55                  60

Val Val Asn Ile Thr Ser Leu Ile Ile Gly Asn Arg Pro Pro Arg Ser
 65                  70                  75                  80

Thr Arg Leu Val Lys Asn Gly Gln Asp Ile Gly Glu Tyr Val Gln Lys
                 85                  90                  95

Asn Ala Pro Glu Phe Cys
            100
```

<210> SEQ ID NO 81
<211> LENGTH: 306
<212> TYPE: DNA
<213> ORGANISM: Solanum lycopersicum, cv. Micro-Tom, wild-type
<220> FEATURE:
<221> NAME/KEY: CDS
<222> LOCATION: (1)..(306)

<400> SEQUENCE: 81

```
atg ata gtt ggg aac tta tca aga agc caa ttg agc aaa gag caa gtg     48
Met Ile Val Gly Asn Leu Ser Arg Ser Gln Leu Ser Lys Glu Gln Val
 1               5                   10                  15 caa gtc tac atc aat gaa gag aat aat agg agg aag agt ctc ttg gtg     96
Gln Val Tyr Ile Asn Glu Glu Asn Asn Arg Arg Lys Ser Leu Leu Val
                 20                  25                  30 aaa tac att cgc cta tgc aac gat gcc aaa gta cca gtt gat act atg    144
Lys Tyr Ile Arg Leu Cys Asn Asp Ala Lys Val Pro Val Asp Thr Met
             35                  40                  45 ctt gtg gaa agc aat tca cca gct aaa gca tta ctt gac ctt ata cct    192
Leu Val Glu Ser Asn Ser Pro Ala Lys Ala Leu Leu Asp Leu Ile Pro
         50                  55                  60 gtt gtc aac att aca agc ctt att att gga aac agg cca ccg cgt tcc    240
Val Val Asn Ile Thr Ser Leu Ile Ile Gly Asn Arg Pro Pro Arg Ser
 65                  70                  75                  80
```

```
acg agg cta gta aag aat gga caa gat ata gga gaa tat gtt caa aaa    288
Thr Arg Leu Val Lys Asn Gly Gln Asp Ile Gly Glu Tyr Val Gln Lys
             85                  90                  95 aat gca cca gag ttc tga                                             306
Asn Ala Pro Glu Phe
            100

<210> SEQ ID NO 82
<211> LENGTH: 101
<212> TYPE: PRT
<213> ORGANISM: Solanum lycopersicum, cv. Micro-Tom, wild-type

<400> SEQUENCE: 82

Met Ile Val Gly Asn Leu Ser Arg Ser Gln Leu Ser Lys Glu Gln Val
1               5                   10                  15

Gln Val Tyr Ile Asn Glu Glu Asn Asn Arg Arg Lys Ser Leu Leu Val
            20                  25                  30

Lys Tyr Ile Arg Leu Cys Asn Asp Ala Lys Val Pro Val Asp Thr Met
        35                  40                  45

Leu Val Glu Ser Asn Ser Pro Ala Lys Ala Leu Leu Asp Leu Ile Pro
    50                  55                  60

Val Val Asn Ile Thr Ser Leu Ile Ile Gly Asn Arg Pro Pro Arg Ser
65                  70                  75                  80

Thr Arg Leu Val Lys Asn Gly Gln Asp Ile Gly Glu Tyr Val Gln Lys
                85                  90                  95

Asn Ala Pro Glu Phe
            100

<210> SEQ ID NO 83
<211> LENGTH: 1068
<212> TYPE: DNA
<213> ORGANISM: Solanum lycopersicum, cv. Micro-Tom, mutant
<220> FEATURE:
<221> NAME/KEY: CDS
<222> LOCATION: (1)..(1068)

<400> SEQUENCE: 83 atg gca ccc agt atg gat tgt gca gtt tcc agc ctt ttg tgt gct gaa    48
Met Ala Pro Ser Met Asp Cys Ala Val Ser Ser Leu Leu Cys Ala Glu
1               5                   10                  15 gac aac agt agc att ttt tgc aat gag gac gat gat gtc gga ttt ggg    96
Asp Asn Ser Ser Ile Phe Cys Asn Glu Asp Asp Asp Val Gly Phe Gly
            20                  25                  30 ttt gta gag gaa gtt gtg ggg gaa gat ata tgg tat cct agg att cat    144
Phe Val Glu Glu Val Val Gly Glu Asp Ile Trp Tyr Pro Arg Ile His
        35                  40                  45 cga aat ggt caa gaa aac agg aag ttg ttt aat gga tat gag ttt tat    192
Arg Asn Gly Gln Glu Asn Arg Lys Leu Phe Asn Gly Tyr Glu Phe Tyr
    50                  55                  60 act ggt gta cca ttg cag agt gat gag tgt tta gtt ttg atg att gaa    240
Thr Gly Val Pro Leu Gln Ser Asp Glu Cys Leu Val Leu Met Ile Glu
65                  70                  75                  80 aaa gaa tgt gaa cat atg cct gct gtt gat tat ctt gaa aga ttg aga    288
Lys Glu Cys Glu His Met Pro Ala Val Asp Tyr Leu Glu Arg Leu Arg
                85                  90                  95 aat ggg gat ttg gat att ggg gct aga gat gag att ctt gat tgg att    336
Asn Gly Asp Leu Asp Ile Gly Ala Arg Asp Glu Ile Leu Asp Trp Ile
            100                 105                 110 gct aag gtt cat tcg cag ttc aat ttt ggt cca atg tgt gca tat ttg    384
Ala Lys Val His Ser Gln Phe Asn Phe Gly Pro Met Cys Ala Tyr Leu
        115                 120                 125
```

```
gct gtg aac tat ctt gat aga ttc ctt tct gct tat gac ttg cct aag      432
Ala Val Asn Tyr Leu Asp Arg Phe Leu Ser Ala Tyr Asp Leu Pro Lys
    130                 135                 140 gaa aag gct tgg atg atg cag tta ctc ggc gta gct tgt ctg tcg att      480
Glu Lys Ala Trp Met Met Gln Leu Leu Gly Val Ala Cys Leu Ser Ile
145                 150                 155                 160 gct gcc aaa atg gag gag act gat gtt cct ctg tct cta gat tta cag      528
Ala Ala Lys Met Glu Glu Thr Asp Val Pro Leu Ser Leu Asp Leu Gln
                165                 170                 175 gga ggg gat gca aag ttt gta ttt gaa gct aaa aca ata cag aga atg      576
Gly Gly Asp Ala Lys Phe Val Phe Glu Ala Lys Thr Ile Gln Arg Met
            180                 185                 190 gag cta ctt gtg tta acc aca ttg aaa tgg aga atg cag gct atc acc      624
Glu Leu Leu Val Leu Thr Thr Leu Lys Trp Arg Met Gln Ala Ile Thr
        195                 200                 205 cca ttc tct tac ata gat tat ttc atc aag aag ata aat aat agc gat      672
Pro Phe Ser Tyr Ile Asp Tyr Phe Ile Lys Lys Ile Asn Asn Ser Asp
    210                 215                 220 caa ata tct tcg atc aat aaa tca gtt gaa ctc ata cta agc aca cta      720
Gln Ile Ser Ser Ile Asn Lys Ser Val Glu Leu Ile Leu Ser Thr Leu
225                 230                 235                 240 aaa ggt att aac ttc ttg gaa ttc aag cct tct gtg att gca gca gca      768
Lys Gly Ile Asn Phe Leu Glu Phe Lys Pro Ser Val Ile Ala Ala Ala
                245                 250                 255 gta gca atc tca ttt gca gta aaa act gag aca tta gac agt gag aaa      816
Val Ala Ile Ser Phe Ala Val Lys Thr Glu Thr Leu Asp Ser Glu Lys
            260                 265                 270 gca cta tct gct cta gtt cag cat gta caa aag gat aaa gtg atg aag      864
Ala Leu Ser Ala Leu Val Gln His Val Gln Lys Asp Lys Val Met Lys
        275                 280                 285 tgt gtt gaa ctg att caa gca ttg tca tta gca agt gac ttt gtt aaa      912
Cys Val Glu Leu Ile Gln Ala Leu Ser Leu Ala Ser Asp Phe Val Lys
    290                 295                 300 gtt cca att gct tct tca atc cca tct gtt cct cag agt cca att ggt      960
Val Pro Ile Ala Ser Ser Ile Pro Ser Val Pro Gln Ser Pro Ile Gly
305                 310                 315                 320 gtg ttg gat gca gca tgt tta agt tac aca agt gat ggc tca gga gtt     1008
Val Leu Asp Ala Ala Cys Leu Ser Tyr Thr Ser Asp Gly Ser Gly Val
                325                 330                 335 gag tcg cgg tct aat tca tcg cat aat agt cca gtg aag agg aga aag     1056
Glu Ser Arg Ser Asn Ser Ser His Asn Ser Pro Val Lys Arg Arg Lys
            340                 345                 350 cta aat act taa                                                     1068
Leu Asn Thr
        355

<210> SEQ ID NO 84
<211> LENGTH: 355
<212> TYPE: PRT
<213> ORGANISM: Solanum lycopersicum, cv. Micro-Tom, mutant

<400> SEQUENCE: 84

Met Ala Pro Ser Met Asp Cys Ala Val Ser Ser Leu Leu Cys Ala Glu
1               5                   10                  15

Asp Asn Ser Ser Ile Phe Cys Asn Glu Asp Asp Val Gly Phe Gly
            20                  25                  30

Phe Val Glu Glu Val Val Gly Glu Asp Ile Trp Tyr Pro Arg Ile His
        35                  40                  45

Arg Asn Gly Gln Glu Asn Arg Lys Leu Phe Asn Gly Tyr Glu Phe Tyr
    50                  55                  60
```

```
Thr Gly Val Pro Leu Gln Ser Asp Glu Cys Leu Val Leu Met Ile Glu
 65                  70                  75                  80

Lys Glu Cys Glu His Met Pro Ala Val Asp Tyr Leu Glu Arg Leu Arg
                 85                  90                  95

Asn Gly Asp Leu Asp Ile Gly Ala Arg Asp Glu Ile Leu Asp Trp Ile
            100                 105                 110

Ala Lys Val His Ser Gln Phe Asn Phe Gly Pro Met Cys Ala Tyr Leu
        115                 120                 125

Ala Val Asn Tyr Leu Asp Arg Phe Leu Ser Ala Tyr Asp Leu Pro Lys
    130                 135                 140

Glu Lys Ala Trp Met Met Gln Leu Leu Gly Val Ala Cys Leu Ser Ile
145                 150                 155                 160

Ala Ala Lys Met Glu Glu Thr Asp Val Pro Leu Ser Leu Asp Leu Gln
                165                 170                 175

Gly Gly Asp Ala Lys Phe Val Phe Glu Ala Lys Thr Ile Gln Arg Met
            180                 185                 190

Glu Leu Leu Val Leu Thr Thr Leu Lys Trp Arg Met Gln Ala Ile Thr
        195                 200                 205

Pro Phe Ser Tyr Ile Asp Tyr Phe Ile Lys Lys Ile Asn Asn Ser Asp
    210                 215                 220

Gln Ile Ser Ser Ile Asn Lys Ser Val Glu Leu Ile Leu Ser Thr Leu
225                 230                 235                 240

Lys Gly Ile Asn Phe Leu Glu Phe Lys Pro Ser Val Ile Ala Ala Ala
                245                 250                 255

Val Ala Ile Ser Phe Ala Val Lys Thr Glu Thr Leu Asp Ser Glu Lys
            260                 265                 270

Ala Leu Ser Ala Leu Val Gln His Val Gln Lys Asp Lys Val Met Lys
        275                 280                 285

Cys Val Glu Leu Ile Gln Ala Leu Ser Leu Ala Ser Asp Phe Val Lys
    290                 295                 300

Val Pro Ile Ala Ser Ser Ile Pro Ser Val Pro Gln Ser Pro Ile Gly
305                 310                 315                 320

Val Leu Asp Ala Ala Cys Leu Ser Tyr Thr Ser Asp Gly Ser Gly Val
                325                 330                 335

Glu Ser Arg Ser Asn Ser Ser His Asn Ser Pro Val Lys Arg Arg Lys
            340                 345                 350

Leu Asn Thr
        355

<210> SEQ ID NO 85
<211> LENGTH: 1068
<212> TYPE: DNA
<213> ORGANISM: Solanum lycopersicum, cv. Micro-Tom, wild-type
<220> FEATURE:
<221> NAME/KEY: CDS
<222> LOCATION: (1)..(1068)

<400> SEQUENCE: 85 atg gca ccc agt atg gat tgt gca gtt tcc agc ctt ttg tgt gct gaa      48
Met Ala Pro Ser Met Asp Cys Ala Val Ser Ser Leu Leu Cys Ala Glu
1               5                   10                  15 gac aac agt agc att ttt tgc aat gag gac gat gat gtc gga ttt ggg      96
Asp Asn Ser Ser Ile Phe Cys Asn Glu Asp Asp Asp Val Gly Phe Gly
            20                  25                  30 ttt gta gag gaa gtt gtg ggg gaa gat ata tgg tat cct agg att cat     144
Phe Val Glu Glu Val Val Gly Glu Asp Ile Trp Tyr Pro Arg Ile His
        35                  40                  45
```

| | | |
|---|---|---|
| cga aat ggt caa gaa aac agg aag ttg ttt aat gga gat gag ttt tat<br>Arg Asn Gly Gln Glu Asn Arg Lys Leu Phe Asn Gly Asp Glu Phe Tyr<br>50                        55                   60 | | 192 |
| act ggt gta cca ttg cag agt gat gag tgt tta gtt ttg atg att gaa<br>Thr Gly Val Pro Leu Gln Ser Asp Glu Cys Leu Val Leu Met Ile Glu<br>65                        70                 75                80 | | 240 |
| aaa gaa tgt gaa cat atg cct gct gtt gat tat ctt gaa aga ttg aga<br>Lys Glu Cys Glu His Met Pro Ala Val Asp Tyr Leu Glu Arg Leu Arg<br>                        85                   90                95 | | 288 |
| aat ggg gat ttg gat att ggg gct aga gat gag att ctt gat tgg att<br>Asn Gly Asp Leu Asp Ile Gly Ala Arg Asp Glu Ile Leu Asp Trp Ile<br>                100                   105               110 | | 336 |
| gct aag gtt cat tcg cag ttc aat ttt ggt cca atg tgt gca tat ttg<br>Ala Lys Val His Ser Gln Phe Asn Phe Gly Pro Met Cys Ala Tyr Leu<br>               115                 120               125 | | 384 |
| gct gtg aac tat ctt gat aga ttc ctt tct gct tat gac ttg cct aag<br>Ala Val Asn Tyr Leu Asp Arg Phe Leu Ser Ala Tyr Asp Leu Pro Lys<br>130                       135                 140 | | 432 |
| gaa aag gct tgg atg atg cag tta ctc ggc gta gct tgt ctg tcg att<br>Glu Lys Ala Trp Met Met Gln Leu Leu Gly Val Ala Cys Leu Ser Ile<br>145                      150                155              160 | | 480 |
| gct gcc aaa atg gag gag act gat gtt cct ctg tct cta gat tta cag<br>Ala Ala Lys Met Glu Glu Thr Asp Val Pro Leu Ser Leu Asp Leu Gln<br>               165                 170               175 | | 528 |
| gga ggg gat gca aag ttt gta ttt gaa gct aaa aca ata cag aga atg<br>Gly Gly Asp Ala Lys Phe Val Phe Glu Ala Lys Thr Ile Gln Arg Met<br>                 180                185               190 | | 576 |
| gag cta ctt gtg tta acc aca ttg aaa tgg aga atg cag gct atc acc<br>Glu Leu Leu Val Leu Thr Thr Leu Lys Trp Arg Met Gln Ala Ile Thr<br>               195                200              205 | | 624 |
| cca ttc tct tac ata gat tat ttc atc aag aag ata aat aat agc gat<br>Pro Phe Ser Tyr Ile Asp Tyr Phe Ile Lys Lys Ile Asn Asn Ser Asp<br>210                       215               220 | | 672 |
| caa ata tct tcg atc aat aaa tca gtt gaa ctc ata cta agc aca cta<br>Gln Ile Ser Ser Ile Asn Lys Ser Val Glu Leu Ile Leu Ser Thr Leu<br>225                      230                235              240 | | 720 |
| aaa ggt att aac ttc ttg gaa ttc aag cct tct gtg att gca gca gca<br>Lys Gly Ile Asn Phe Leu Glu Phe Lys Pro Ser Val Ile Ala Ala Ala<br>                 245                250              255 | | 768 |
| gta gca atc tca ttt gca gta aaa act gag aca tta gac agt gag aaa<br>Val Ala Ile Ser Phe Ala Val Lys Thr Glu Thr Leu Asp Ser Glu Lys<br>                 260                265              270 | | 816 |
| gca cta tct gct cta gtt cag cat gta caa aag gat aaa gtg atg aag<br>Ala Leu Ser Ala Leu Val Gln His Val Gln Lys Asp Lys Val Met Lys<br>275                      280               285 | | 864 |
| tgt gtt gaa ctg att caa gca ttg tca tta gca agt gac ttt gtt aaa<br>Cys Val Glu Leu Ile Gln Ala Leu Ser Leu Ala Ser Asp Phe Val Lys<br>290                       295                300 | | 912 |
| gtt cca att gct tct tca atc cca tct gtt cct cag agt cca att ggt<br>Val Pro Ile Ala Ser Ser Ile Pro Ser Val Pro Gln Ser Pro Ile Gly<br>305                       310                315              320 | | 960 |
| gtg ttg gat gca gca tgt tta agt tac aca agt gat ggc tca gga gtt<br>Val Leu Asp Ala Ala Cys Leu Ser Tyr Thr Ser Asp Gly Ser Gly Val<br>                 325                330              335 | | 1008 |
| gag tcg cgg tct aat tca tcg cat aat agt cca gtg aag agg aga aag<br>Glu Ser Arg Ser Asn Ser Ser His Asn Ser Pro Val Lys Arg Arg Lys<br>               340                345               350 | | 1056 |
| cta aat act taa<br>Leu Asn Thr<br>355 | | 1068 |

```
<210> SEQ ID NO 86
<211> LENGTH: 355
<212> TYPE: PRT
<213> ORGANISM: Solanum lycopersicum, cv. Micro-Tom, wild-type

<400> SEQUENCE: 86

Met Ala Pro Ser Met Asp Cys Ala Val Ser Ser Leu Leu Cys Ala Glu
1               5                   10                  15

Asp Asn Ser Ser Ile Phe Cys Asn Glu Asp Asp Val Gly Phe Gly
            20                  25                  30

Phe Val Glu Val Val Gly Glu Asp Ile Trp Tyr Pro Arg Ile His
        35                  40                  45

Arg Asn Gly Gln Glu Asn Arg Lys Leu Phe Asn Gly Asp Glu Phe Tyr
    50                  55                  60

Thr Gly Val Pro Leu Gln Ser Asp Glu Cys Leu Val Leu Met Ile Glu
65                  70                  75                  80

Lys Glu Cys Glu His Met Pro Ala Val Asp Tyr Leu Glu Arg Leu Arg
                85                  90                  95

Asn Gly Asp Leu Asp Ile Gly Ala Arg Asp Glu Ile Leu Asp Trp Ile
            100                 105                 110

Ala Lys Val His Ser Gln Phe Asn Phe Gly Pro Met Cys Ala Tyr Leu
        115                 120                 125

Ala Val Asn Tyr Leu Asp Arg Phe Leu Ser Ala Tyr Asp Leu Pro Lys
    130                 135                 140

Glu Lys Ala Trp Met Met Gln Leu Leu Gly Val Ala Cys Leu Ser Ile
145                 150                 155                 160

Ala Ala Lys Met Glu Glu Thr Asp Val Pro Leu Ser Leu Asp Leu Gln
                165                 170                 175

Gly Gly Asp Ala Lys Phe Val Phe Glu Ala Lys Thr Ile Gln Arg Met
            180                 185                 190

Glu Leu Leu Val Leu Thr Thr Leu Lys Trp Arg Met Gln Ala Ile Thr
        195                 200                 205

Pro Phe Ser Tyr Ile Asp Tyr Phe Ile Lys Lys Ile Asn Asn Ser Asp
    210                 215                 220

Gln Ile Ser Ser Ile Asn Lys Ser Val Glu Leu Ile Leu Ser Thr Leu
225                 230                 235                 240

Lys Gly Ile Asn Phe Leu Glu Phe Lys Pro Ser Val Ile Ala Ala Ala
                245                 250                 255

Val Ala Ile Ser Phe Ala Val Lys Thr Glu Thr Leu Asp Ser Glu Lys
            260                 265                 270

Ala Leu Ser Ala Leu Val Gln His Val Gln Lys Asp Lys Val Met Lys
        275                 280                 285

Cys Val Glu Leu Ile Gln Ala Leu Ser Leu Ala Ser Asp Phe Val Lys
    290                 295                 300

Val Pro Ile Ala Ser Ser Ile Pro Ser Val Pro Gln Ser Pro Ile Gly
305                 310                 315                 320

Val Leu Asp Ala Ala Cys Leu Ser Tyr Thr Ser Asp Gly Ser Gly Val
                325                 330                 335

Glu Ser Arg Ser Asn Ser Ser His Asn Ser Pro Val Lys Arg Arg Lys
            340                 345                 350

Leu Asn Thr
        355
```